US008178699B2

(12) United States Patent
Anderson et al.

(10) Patent No.: US 8,178,699 B2
(45) Date of Patent: May 15, 2012

(54) MODULATORS OF CCR9 RECEPTOR AND METHODS OF USE THEREOF

(75) Inventors: Eric C Anderson, Irving, TX (US); Ronald J Biediger, Houston, TX (US); Jie Chen, Houston, TX (US); Brian Dupre, Houston, TX (US); Pedro Lory, Antwerp (BE); Robert V. Market, Pearland, TX (US); Keith A. Monk, League City, TX (US); Michael M. Savage, Pearland, TX (US); Reginald Tennyson, Missouri City, TX (US); Brandon M. Young, Germantown, TN (US)

(73) Assignee: Pfizer Inc., New York, NY (US)

( * ) Notice: Subject to any disclaimer, the term of this patent is extended or adjusted under 35 U.S.C. 154(b) by 754 days.

(21) Appl. No.: 12/183,032

(22) Filed: Jul. 30, 2008

(65) Prior Publication Data

US 2010/0029753 A1     Feb. 4, 2010

(51) Int. Cl.
    *C07D 333/56*    (2006.01)
(52) U.S. Cl. ......................................................... 549/57
(58) Field of Classification Search .................. 514/301; 546/114; 549/57
    See application file for complete search history.

(56) References Cited

U.S. PATENT DOCUMENTS

2004/0180892 A1    9/2004    Wu et al. .................... 514/237.5

FOREIGN PATENT DOCUMENTS

| JP | 2001002687 | 1/2001 |
| WO | WO 9816520 | 4/1998 |
| WO | WO 02/100851 A2 * | 12/2002 |

OTHER PUBLICATIONS

Schall, Cytokine, 3:165, p. 183, 1991.
Schall et al, Curr Opin Immunol, 6:865, 873, 1994.
Murphy, Rev. Immun, 12:593, 633, 1994.
Papadakis et al, Gastroenterology, 121:246-254, 2001.
Svensson et al., J. Clin. Invest., 110:1113-21, 2002.
Eksteen et al., J. Exp. Med. 200:1511-1517, 2004.
Liu et al., J. Allergy Clin Immunol, 112(3):556-62, Sep. 2003.
Singh et al., Clinical Cancer Research, 10:8743-8750, 2004.
Letsch et al., J. Invest Dermatol, 122:685-690, 2004.
Quiping et al,, Cancer Res. 63(19):6469-77, Oct. 2003.
Poles et al., J. Viral, 77(19)10456-67, Oct. 2003.

* cited by examiner

*Primary Examiner* — Taofiq A Solola
(74) *Attorney, Agent, or Firm* — A. Dean Olson

(57) ABSTRACT

Provided are compounds that are modulators of CCR9 receptor activity, compositions containing the compounds and methods of use of the compounds and compositions. In certain embodiments, provided are methods for treating or ameliorating diseases associated with modulation of CCR9 receptor activity.

2 Claims, No Drawings

MODULATORS OF CCR9 RECEPTOR AND METHODS OF USE THEREOF

FIELD

Provided herein are compounds, compositions and methods for treating, preventing or ameliorating conditions associated with CCR9 receptor activity.

BACKGROUND

Chemokines are chemotactic cytokines that are released by a wide variety of cells and attract various types of immune system cells, such as macrophages, T cells, eosinophils, basophils and neutrophils, to sites of inflammation (reviewed in Schall, Cytokine, 3:165-183 (1991), Schall, et al., Curr. Opin. Immunol., 6:865 873 (1994) and Murphy, Rev. Immun., 12:593-633 (1994)). In addition to stimulating chemotaxis, other changes can be selectively induced by chemokines in responsive cells, including changes in cell shape, transient rises in the concentration of intracellular free calcium ions ($[Ca^{2+}]$), granule exocytosis, integrin up-regulation, formation of bioactive lipids (e.g., leukotrienes) and respiratory burst, associated with leukocyte activation. Thus, the chemokines are early triggers of the inflammatory response, causing inflammatory mediator release, chemotaxis and extravasation to sites of infection or inflammation.

CCR9, a seven transmembrane, G-protein-coupled chemokine receptor was recently identified as the physiologic receptor for CCL25/thymus-expressed Chemokine (TECK). CCR9 is mainly expressed in thymocytes and T lymphocytes from the small intestine and colon. CCL25/TECK is predominantly expressed in the thymus and small intestine. Studies have shown that CCR9 mediates chemotaxis in response to CCL25/TECK and is likely to play an important role in regulating the trafficking of developing T cells within the thymus and be critical for the development, homeostasis, and/or function of mucosal T lymphocytes.

It has been shown that CCR9+ lymphocytes are markedly elevated in peripheral blood lymphocytes in patients with small bowel Crohn's or celiac disease. TECK expression is altered in an inflamed small bowel being intensely expressed in a patchy distribution in crypt epithelial cells in proximity to lymphocytic infiltrates (Papadakis et al. Gastroenterology, 2001, 121:246-254). In mouse models, neutralization of TECK inhibits homing of CD8+ T cells to the IEL (intraepithelial lymphocyte) compartment. This directly demonstrates that CCL25 and CCR9 function in recruiting effector lymphocytes to the small intestinal epithelium following their activation in gut-associated lymphoid tissue (GALT).

Targeting CCL25/TECK and/or CCR9 may provide a way to selectively modulate small-intestinal immune responses as suggested by the fact that activated CCR9(+) CD8alphabeta (+) lymphocytes selectively localized to the small-intestinal mucosa, and in vivo neutralization of CCL25/TECK reduced the ability of these cells to populate the small-intestinal epithelium. These results demonstrate an important role for chemokines in the localization of T lymphocytes to the small-intestinal mucosa. (Svensson et al., J. Clin. Invest., 2002, 110:1113-21). CCR9+ gut-homing lymphocytes have also been implicated in primary sclerosing cholangitis, a chronic liver disease that is a common complication of inflammatory bowel disease (Eksteen et al., J. Exp. Med., 2004, 200:1511-1517).

CCR9 receptor expression on human eosinophils from peripheral blood and bronchoalveolar lavage fluid after segmental antigen challenge was reported recently (Liu et al, J Allergy Clin Immunol 2003 September; 112(3):556-62). Studies by Singh et al. (Clinical Cancer Research, 2004, 10, 8743-8750) suggest that the expression and activation of CCR9 affect cancer cell migration, invasion, and MMP expression, which together may affect prostate cancer metastasis. In a similar fashion, functional CCR9 has been detected on the surface of small intestinal melanoma (Letsch et al., 2004 J. Invest. Dermatol. 122:685-690).

CCR9 was also found to be selectively expressed on T-ALL CD4+ T cells and moderately expressed on T-CLL CD4+ T cells. CCL25,TECK selectively induced T-ALL CD4+ T cell chemotaxis and adhesion (Qiuping et al., Cancer Res. 2003 Oct. 1; 63(19):6469-77. Annels et al., Blood 2003). A recent study also demonstrates an increase in the expression of CCR9 on peripheral blood gammadelta T cells in individuals having HIV-1 infection (Poles et al., J. Virol. 2003 October; 77(19):10456-67).

Because of the involvement of the CCR9 receptor in a variety of diseases, there is a continuing need for compounds that modulate the binding or function of various chemokines to the CCR9 receptor.

SUMMARY

Provided herein are compounds that are modulators of CCR9 receptor, pharmaceutical compositions containing the compounds and methods of use thereof In certain embodiments, the compounds for use in the compositions and methods provided herein are of formula I:

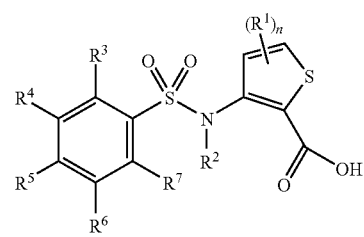

or a pharmaceutically acceptable derivative thereof, wherein the variables are chosen such that the resulting compound shows activity as a CCR9 modulator. In one embodiment, the compounds are CCR9 receptor antagonists.

Pharmaceutical compositions containing a compound of Formula I and a pharmaceutically acceptable carrier are provided herein. Also provided are methods for treating, preventing, or ameliorating one or more symptoms of CCR9 receptor mediated diseases by administering the compounds and compositions provided herein.

In certain embodiments, provided herein are methods for modulating an activity of CCR9 receptor by contacting the receptor with a compound or composition provided herein. In one embodiment, provided herein are methods for antagonizing an action of CCR9 receptor by contacting the receptor with a compound or composition provided herein. In other embodiments, provided herein are methods for treatment, prevention, or amelioration of one or more symptoms of diseases or conditions associated with CCR9 receptor activity, including, but not limited to inflammatory bowel disease, including Crohn's disease and ulcerative colitis, celiac disease and other forms of intestinal inflammation, including celiac sprue and gluten-sensitive enteropathy; primary sclerosing cholangitis; HIV; as well as various cancers, including, prostate cancer, leukemia, and small intestinal melanoma.

DETAILED DESCRIPTION

Definitions

Unless defined otherwise, all technical and scientific terms used herein have the same meaning as is commonly understood by one of ordinary skill in the art. All patents, applications, published applications and other publications re incorporated by reference in their entirety. In the event that there are a plurality of definitions for a term herein, those in this section prevail unless stated otherwise.

The singular forms "a," "an," and "the" include plural references, unless the context clearly dictates otherwise.

As used herein "subject" is an animal, such as a mammal, including human, such as a patient.

The terms "CCR9 receptor mediated disease, or "CCR9 receptor mediated condition", as used herein, mean any disease or other deleterious condition or state in which CCR9 receptor is known to play a role. Such diseases or conditions include, without limitation, congestive heart failure, stroke, ischemic heart disease (angina, myocardial ischemia), cardiac arrhythmia, hypertension (essential and pulmonary), renal disease (acute and chronic renal failure/end stage renal disease) along with peripheral vascular disease (male erectile dysfunction, diabetic retinopathy, intermittent claudication/ischemic limb disease) and ischemic/hemorrhage stroke, COPD, restenosis, asthma, neurogenic inflammation, migraine, metabolic vasculopathies, bone/cartilage/joint disease, arthritis and other inflammatory diseases, fibrosis (e.g. pulmonary fibrosis), sepsis atherosclerosis, dyslipidemia, addiction, schizophrenia, cognitive disorders/Alzheimers disease, impulsivity, anxiety, stress, depression, parkinsons, movement disorders, sleepwake cycle, incentive motivation, pain, neuromuscular function, diabetes, gastric reflux, gastric motility disorders, ulcers and genitourinary diseases. Also included are inflammatory bowel disease, including Crohn's disease and ulcerative colitis; celiac disease and other forms of intestinal inflammation, including celiac sprue, gluten-sensitive enteropathy; primary sclerosing cholangitis; HIV; as well as various cancers, including, prostate cancer, leukemia, small intestinal and melanoma.

As used herein, biological activity refers to the in vivo activities of a compound or physiological responses that result upon in vivo administration of a compound, composition or other mixture. Biological activity, thus, encompasses therapeutic effects and pharmacokinetic behaviour of such compounds, compositions and mixtures. Biological activities can be observed in in vitro systems designed to test for such activities.

As used herein, pharmaceutically acceptable derivatives of a compound include, but are not limited to, salts, esters, enol ethers, enol esters, acetals, ketals, orthoesters, hemiacetals, hemiketals, acids bases, solvates or hydrates thereof. Such derivatives may be readily prepared by those of skill in this art using known methods for such derivatization. The compounds produced may be administered to animals or humans without substantial toxic effects and either are pharmaceutically active or are prodrugs. Pharmaceutically acceptable salts include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethylbenzimidazole, diethylamine and other alkylamines, piperazine and tris(hydroxymethyl)aminomethane; alkali metal salts, such as but not limited to lithium, potassium and sodium, alkali earth metal salts, such as but not limited to barium, calcium and magnesium; transition metal salts, such as but not limited to zinc; and inorganic salts, such as but not limited to, sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates, mesylates, and fumarates. Pharmaceutically acceptable esters include, but are not limited to, alkyl, alkenyl, alkynyl, aryl, aralkyl, and cycloalkyl esters of acidic groups, including, but not limited to, carboxylic acids, phosphoric acids, phosphinic acids, sulfonic acids, sulfinic acids and boronic acids. Pharmaceutically acceptable enol ethers include, but are not limited to, derivatives of formula C=C(OR) where R is alkyl, alkenyl, alkynyl, aryl, aralkyl and cycloalkyl. Pharmaceutically acceptable enol esters include, but are not limited to, derivatives of formula C=C(OC(O)R) where R is hydrogen, alkyl alkenyl, alkynyl, aryl, aralkyl and cycloalkyl. Pharmaceutically acceptable solvates and hydrates are complexes of a compound with one or more solvent or water molecules, or 1 to about 100, or 1 to about 10, or one to about 2, 3 or 4, solvent or water molecules.

As used herein, treatment means any manner in which one or more of the symptoms of a disease or disorder are ameliorated or otherwise beneficially altered. Treatment also encompasses any pharmaceutical use of the compositions herein, such as use for treating inflammation.

As used herein, amelioration of the symptoms of a particular disorder by administration of a particular compound or pharmaceutical composition refers to any lessening, whether permanent or temporary, lasting or transient that can be attributed to or associated with administration of the composition.

As used herein, and unless otherwise indicated, the terms "manage," "managing" and "management" encompass preventing the recurrence of the specified disease or disorder in a patient who has already suffered from the disease or disorder, and/or lengthening the time that a patient who has suffered from the disease or disorder remains in remission. The terms encompass modulating the threshold, development and/or duration of the disease or disorder, or changing the way that a patient responds to the disease or disorder.

As used herein, the $IC_{50}$ refers to an amount, concentration or dosage of a particular test compound that achieves a 50% inhibition of a maximal response in an assay that measures such response.

It is to be understood that the compounds provided herein may contain chiral centers. Such chiral centers may be of either the (R) or (S) configuration, or may be a mixture thereof. Thus, the compounds provided herein may be enantiomerically pure, or be stereoisomeric or diastereomeric mixtures. As such, one of skill in the art will recognize that administration of a compound in its (R) form is equivalent, for compounds that undergo epimerization in vivo, to administration of the compound in its (S) form.

As used herein, substantially pure means sufficiently homogeneous to appear free of readily detectable impurities as determined by standard methods of analysis, such as thin layer chromatography (TLC), gel electrophoresis, high performance liquid chromatography (HPLC) and mass spectrometry (MS), used by those of skill in the art to assess such purity, or sufficiently pure such that further purification would not detectably alter enzymatic and biological activities of the substance. Methods for purification of the compounds to produce substantially chemically pure compounds are known to those of skill in the art. A substantially chemically pure compound may, however, be a mixture of stereoisomers. In such instances, further purification might increase the specific activity of the compound. The instant disclosure is meant to include all such possible isomers, as well as, their racemic and optically pure forms. Optically active (+) and (−), (R)- and (S)-, or (D)- and (L)-isomers may be prepared using chiral synthons or chiral reagents, or resolved using conventional techniques, such as reverse phase HPLC. When the compounds described herein contain olefinic double bonds or other centers of geometric asymmetry, and unless specified otherwise, it is intended that the compounds include both E and Z geometric isomers. Likewise, all tautomeric forms are also intended to be included.

As used herein, the nomenclature alkyl, alkoxy, carbonyl, etc. is used as is generally understood by those of skill in this art.

As used herein, alkyl, alkenyl and alkynyl carbon chains, if not specified, contain from 1 to 20 carbons, or 1 to 16 carbons, and are straight or branched. Alkenyl carbon chains of from 2 to 20 carbons, in certain embodiments, contain 1 to 8 double bonds, and the alkenyl carbon chains of 2 to 16 carbons, in certain embodiments, contain 1 to 5 double bonds. Alkynyl carbon chains of from 2 to 20 carbons, in certain embodiments, contain 1 to 8 triple bonds, and the alkynyl carbon chains of 2 to 16 carbons, in certain embodiments, contain 1 to 5 triple bonds. Exemplary alkyl, alkenyl and alkynyl groups herein include, but are not limited to, methyl, ethyl, propyl, isopropyl, isobutyl, n-butyl, sec-butyl, tert-butyl, isopentyl, neopentyl, tert-pentyl, isohexyl, ethenyl, propenyl, butenyl, pentenyl, acetylenyl and hexynyl. As used herein, lower alkyl, lower alkenyl, and lower alkynyl refer to carbon chains having from about 1 or about 2 carbons up to about 6 carbons. As used herein, "alk(en)(yn)yl" refers to an alkyl group containing at least one double bond and at least one triple bond.

As used herein, "heteroalkyl" refers to a straight or branched aliphatic hydrocarbon group having, inserted in the hydrocarbon chain one or more oxygen, sulfur, including $S(=O)$ and $S(=O)_2$ groups, or substituted or unsubstituted nitrogen atoms, including —NR— and —N$^+$RR— groups, where the nitrogen substituent(s) is(are) alkyl, aryl, aralkyl, heteroaryl, heteroaralkyl, $S(=O)_2R'$ or COR', where R' is alkyl, aryl, aralkyl, heteroaryl, heteroaralkyl, OY or —NYY', where Y and Y' are each independently hydrogen, alkyl, aryl, heteroaryl, cycloalkyl or heterocyclyl, in one embodiment having from 1 to about 20 atoms, in another embodiment having from 1 to 12 atoms in the chain.

As used herein, "cycloalkyl" refers to a saturated mono- or multicyclic ring system, in certain embodiments of 3 to 10 carbon atoms, in other embodiments of 3 to 6 carbon atoms; cycloalkenyl and cycloalkynyl refer to mono- or multicyclic ring systems that respectively include at least one double bond and at least one triple bond. Cycloalkenyl and cycloalkynyl groups may, in certain embodiments, contain 3 to 10 carbon atoms, with cycloalkenyl groups, in further embodiments, containing 4 to 7 carbon atoms and cycloalkynyl groups, in further embodiments, containing 8 to 10 carbon atoms. The ring systems of the cycloalkyl, cycloalkenyl and cycloalkynyl groups may be composed of one ring or two or more rings which may be joined together in a fused, bridged or spiro-connected fashion. "Cycloalk(en)(yn)yl" refers to a cycloalkyl group containing at least one double bond and at least one triple bond.

As used herein, "substituted alkyl," "substituted alkenyl," "substituted alkynyl," "substituted cycloalkyl," "substituted cycloalkenyl," and "substituted cycloalkynyl" refer to alkyl, alkenyl, alkynyl, cycloalkyl, cycloalkenyl and cycloalkynyl groups, respectively, that are substituted with one or more substituents, in certain embodiments one to three or four substituents, where the substituents are as defined herein generally selected from $Q^1$.

As used herein, "aryl" refers to aromatic monocyclic or multicyclic groups containing from 6 to 19 carbon atoms. Aryl groups include, but are not limited to groups such as fluorenyl, substituted fluorenyl, phenyl, substituted phenyl, naphthyl and substituted naphthyl.

As used herein, "heteroaryl" refers to a monocyclic or multicyclic aromatic ring system, in certain embodiments, of about 5 to about 15 members where one or more, in one embodiment 1 to 3, of the atoms in the ring system is a heteroatom, that is, an element other than carbon, including but not limited to, nitrogen, oxygen or sulfur. The heteroaryl group may be optionally fused to a benzene ring. Heteroaryl groups include, but are not limited to, furyl, imidazolyl, pyrimidinyl, tetrazolyl, thienyl, pyridyl, pyrrolyl, N-methylpyrrolyl, quinolinyl and isoquinolinyl.

As used herein, "heterocyclyl" refers to a monocyclic or multicyclic non-aromatic ring system, in one embodiment of 3 to 10 members, in another embodiment of 4 to 7 members, in a further embodiment of 5 to 6 members, where one or more, in certain embodiments, 1 to 3, of the atoms in the ring system is a heteroatom, that is, an element other than carbon, including but not limited to, nitrogen, oxygen or sulfur. In embodiments where the heteroatom(s) is(are) nitrogen, the nitrogen is optionally substituted with alkyl, alkenyl, alkynyl, aryl, heteroaryl, aralkyl, heteroaralkyl, cycloalkyl, heterocyclyl, cycloalkylalkyl, heterocyclylalkyl, acyl, guanidino, amidino or the nitrogen may be quaternized to form an ammonium group where the substituents are selected as above.

As used herein, "substituted aryl," "substituted heteroaryl" and "substituted heterocyclyl" refer to aryl, heteroaryl and heterocyclyl groups, respectively, that are substituted with one or more substituents, in certain embodiments one to three or four substituents, where the substituents are as defined herein, generally selected from $Q^1$.

As used herein, "aralkyl" refers to an alkyl group in which one of the hydrogen atoms of the alkyl is replaced by an aryl group.

As used herein, "heteroaralkyl" refers to an alkyl group in which one of the hydrogen atoms of the alkyl is replaced by a heteroaryl group.

As used herein, "halo", "halogen" or "halide" refers to F, Cl, Br or I.

As used herein, pseudohalides or pseudohalo groups are groups that behave substantially similar to halides. Such compounds can be used in the same manner and treated in the same manner as halides. Pseudohalides include, but are not limited to, cyano, thiocyanate, selenocyanate, trifluoromethoxy, and azide.

As used herein, "haloalkyl" refers to an alkyl group in which one or more of the hydrogen atoms are replaced by halogen. Such groups include, but are not limited to, chloromethyl, trifluoromethyl and 1 chloro 2 fluoroethyl.

As used herein, "haloalkoxy" refers to RO in which R is a haloalkyl group.

As used herein, "carboxy" refers to a divalent radical, —C(O)O—.

As used herein, "aminocarbonyl" refers to —C(O)NH$_2$.

As used herein, "alkylaminocarbonyl" refers to —C(O) NHR in which R is alkyl, including lower alkyl. As used herein, "dialkylaminocarbonyl" refers to —C(O)NR'R in which R' and R are independently alkyl, including lower alkyl; "carboxamide" refers to groups of formula —NR'COR in which R' and R are independently alkyl, including lower alkyl.

As used herein, "arylalkylaminocarbonyl" refers to —C(O)NRR' in which one of R and R' is aryl, including lower aryl, such as phenyl, and the other of R and R' is alkyl, including lower alkyl.

As used herein, "arylaminocarbonyl" refers to —C(O)NHR in which R is aryl, including lower aryl, such as phenyl.

As used herein, "hydroxycarbonyl" refers to —COOH.

As used herein, "alkoxycarbonyl" refers to —C(O)OR in which R is alkyl, including lower alkyl.

As used herein, "aryloxycarbonyl" refers to —C(O)OR in which R is aryl, including lower aryl, such as phenyl.

As used herein, "alkoxy" and "alkylthio" refer to RO— and RS—, in which R is alkyl, including lower alkyl.

As used herein, "aryloxy" and "arylthio" refer to RO— and RS—, in which R is aryl, including lower aryl, such as phenyl.

Where the number of any given substituent is not specified (e.g., "haloalkyl"), there may be one or more substituents present. For example, "haloalkyl" may include one or more of the same or different halogens.

As used herein, the abbreviations for any protective groups, amino acids and other compounds, are, unless indicated otherwise, in accord with their common usage, recognized abbreviations, or the IUPAC-IUB Commission on Biochemical Nomenclature (see. (1972) Biochem. 11:942-944).

5.2 Compounds

In certain embodiments, the compounds for use in the compositions and methods provided herein are of Formula I:

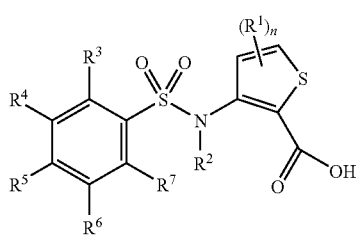

I or pharmaceutically acceptable derivatives thereof,
wherein $R^1$ is selected as follows:
i) each $R^1$ is independently selected from H, alkyl, alkenyl, alkynyl, aryl, cycloalkyl, heterocyclyl, heteroaryl, halo, pseudohalo, $OR^8$, $C(O)R^9$ and $S(O)_p R^9$; or
ii) two $R^1$ groups together with the carbon atoms on which they are substituted form a cycloalkyl, aryl, heteroaryl or heterocyclyl ring;
$R^2$ is selected from H, alkyl, alkenyl, alkynyl, aryl and cycloalkyl;
$R^3$, $R^4$, $R^5$, $R^6$ and $R^7$ are each independently selected as follows:
a) $R^3$, $R^4$, $R^5$, $R^6$ and $R^7$ are each independently selected from H, alkyl, alkenyl, alkynyl, aryl, cycloalkyl, heterocyclyl, heteroaryl, halo, pseudohalo, $OR^8$, $C(O)R^9$ and $S(O)_p R^9$, or
b) at least two of $R^3$, $R^4$, $R^5$, $R^6$ and $R^7$, which substitute adjacent carbons on the ring, together with the carbon atoms on which they are substituted form a fused aryl or cycloalkyl ring;
$R^8$ is hydrogen, alkyl, alkenyl, alkynyl, aryl, heteroaryl, heterocyclyl, cycloalkyl, alkylcarbonyl, cycloalkylcarbonyl or arylcarbonyl;

$R^9$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy or —C(O)$R^8$; and
n is 0-2; and
p is 0-2.

In one embodiment, the compounds have formula I, with a proviso that:
i) when $R^1$ is optionally substituted phenyl, pyridinyl or thienyl, then $R^3$-$R^7$ are other than methyl or chloro:
ii when $R^1$ and $R^2$ are each hydrogen, then $R^5$ is other than H or chloro, and
iii) when $R^2$ is benzyl, then $R^5$ is other than methoxy.

In certain embodiments, $R^1$-$R^9$ are optionally substituted with one or more, in certain embodiments, 1, 2, 3 or 4 substituents, each independently selected from $Q^1$, where $Q^1$ is halo, pseudohalo, hydroxy, oxo, thioxo, nitrile, nitro, formyl, mercapto, hydroxycarbonyl, hydroxycarbonylalkyl, alkyl, haloalkyl, polyhaloalkyl, aminoalkyl, diaminoalkyl, alkenyl containing 1 to 2 double bonds, alkynyl containing 1 to 2 triple bonds, cycloalkyl, cycloalkylalkyl, heterocyclyl, heterocyclylalkyl, aryl, heteroaryl, aralkyl, aralkenyl, aralkynyl, heteroarylalkyl, trialkylsilyl, dialkylarylsilyl, alkyldiarylsilyl, triarylsilyl, alkylidene, arylalkylidene, alkylcarbonyl, arylcarbonyl, heteroarylcarbonyl, alkoxycarbonyl, alkoxycarbonylalkyl, aryloxycarbonyl, aryloxycarbonylalkyl, aralkoxycarbonyl, aralkoxycarbonylalkyl, arylcarbonylalkyl, aminocarbonyl, alkylaminocarbonyl, dialkylaminocarbonyl, arylaminocarbonyl, diarylaminocarbonyl, arylalkylaminocarbonyl, alkoxy, aryloxy, heteroaryloxy, heteroaralkoxy, heterocyclyloxy, cycloalkoxy, perfluoroalkoxy, alkenyloxy, alkynyloxy, aralkoxy, alkylcarbonyloxy, arylcarbonyloxy, aralkylcarbonyloxy, alkoxycarbonyloxy, aryloxycarbonyloxy, aralkoxycarbonyloxy, aminocarbonyloxy, alkylaminocarbonyloxy, dialkylaminocarbonyloxy, alkylarylaminocarbonyloxy, diarylaminocarbonyloxy, guanidino, isothioureido, ureido, N-alkylureido, N-arylureido, N'-alkylureido, N',N'-dialkylureido, N'-alkyl-N'-arylureido, N',N'-diarylureido, N'-arylureido, N,N'-dialkylureido, N-alkyl-N'-arylureido, N-aryl-N'-alkylureido, N,N'-diarylureido, N,N',N'-trialkylureido, N,N'-dialkyl-N'-arylureido, N-alkyl-N',N'-diarylureido, N-aryl-N',N'-dialkylureido, N,N'-diaryl-N'-alkylureido, N,N',N'-triarylureido, amidino, alkylamidino, arylamidino, aminothiocarbonyl, alkylaminothiocarbonyl, arylaminothiocarbonyl, amino, aminoalkyl, alkylaminoalkyl, dialkylaminoalkyl, arylaminoalkyl, diarylaminoalkyl, alkylarylaminoalkyl, alkylamino, dialkylamino, haloalkylamino, arylamino, diarylamino, alkylarylamino, alkylcarbonylamino, alkoxycarbonylamino, aralkoxycarbonylamino, arylcarbonylamino, arylcarbonylaminoalkyl, aryloxycarbonylaminoalkyl, aryloxyarylcarbonylamino, aryloxycarbonylamino, alkylsulfonylamino, arylsulfonylamino, heteroarylsulfonylamino, heterocyclylsulfonylamino, heteroarylthio, azido, —N$^+$R$^{51}$R$^{52}$R$^{53}$, P(R$^{50}$)$_2$, P(=O)(R$^{50}$)$_2$, OP(=O)(R$^{50}$)$_2$, —NR$^{60}$C(=O)R$^{63}$, dialkylphosphonyl, alkylarylphosphonyl, diarylphosphonyl, hydroxyphosphonyl, alkylthio, arylthio, perfluoroalkylthio, hydroxycarbonylalkylthio, thiocyano isothiocyano, alkylsulfinyloxy, alkylsulfonyloxy, arylsulfinyloxy, arylsulfonyloxy, hydroxysulfonyloxy, alkoxysulfonyloxy, aminosulfonyloxy, alkyvlaminosulfonyloxy, dialkylaminosulfonyloxy, arylaminosulfonyloxy, diarylaminosulfonyloxy, alkylarylaminosulfonyloxy, alkylsulfinyl, alkyisulfonyl, arylsulfinyl, arylsulfonyl, hydroxysulfonyl, alkoxysulfonyl, aminosulfonyl, alkylaminosulfonyl, dialkylaminosulfonyl, arylaminosulfonyl, diarylaminosulfonyl or alkylarylaminosulfonyl; or two $Q^1$ groups, which substitute atoms in a 1,2 or 1,3 arrangement, together form alkylene, alkylenoxy (i.e., —O—(CH$_2$)$_y$—), alkylenthioxy (i.e., —S—(CH$_2$)$_y$—), alkylenedioxy (i.e., —O—(CH$_2$)$_y$—O—), thioalkylenoxy (i.e., —S—(CH$_2$)$_y$—O—) or alkylenedithioxy (i.e., —S—(CH$_2$)$_y$—S—) where y is 1 or 2; or two Q$^1$ groups, which substitute the same atom, together form alkylene; and each Q$^1$ is independently unsubstituted or substituted with one, two or three substituents, each independently selected from Q$^2$;

each Q$^2$ is independently halo, pseudohalo, hydroxy, oxo, thioxo, nitrile, nitro, formyl, mercapto, hydroxycarbonyl, hydroxycarbonylalkyl, alkyl, haloalkyl, polyhaloalkyl, aminoalkyl, diaminoalkyl, alkenyl containing 1 to 2 double bonds, alkynyl containing 1 to 2 triple bonds, cycloalkyl, cycloalkylalkyl, heterocyclyl, heterocyclylalkyl, aryl, heteroaryl, aralkyl, aralkenyl, aralkynyl, heteroarylalkyl, trialkylsilyl, dialkylarylsilyl, alkyldiarylsilyl, triarylsilyl, alkylidene, arylalkylidene, alkylcarbonyl, arylcarbonyl, heteroarylcarbonyl, alkoxycarbonyl, alkoxycarbonylalkyl, aryloxycarbonyl, aryloxycarbonylalkyl, aralkoxycarbonyl, aralkoxycarbonylalkyl, arylcarbonylalkyl, aminocarbonyl, alkylaminocarbonyl, dialkylaminocarbonyl, arylaminocarbonyl, diarylaminocarbonyl, arylalkylaminocarbonyl, alkoxy, aryloxy, heteroaryloxy, heteroaralkoxy, heterocyclyloxy, cycloalkoxy, perfluoroalkoxy, alkenyloxy, alkynyloxy, aralkoxy, alkylcarbonyloxy, arylcarbonyloxy, aralkylcarbonyloxy, alkoxycarbonyloxy, aryloxycarbonyloxy, aralkoxycarbonyloxy, aminocarbonyloxy, alkylaminocarbonyloxy, dialkylaminocarbonyloxy, alkylarylaminocarbonyloxy, diarylaminocarbonyloxy, guanidino, isothioureido, ureido, N-alkylureido, N-arylureido, N'-alkylureido, N',N'-dialkylureido, N'-alkyl-N'-arylureido, N',N'-diarylureido, N'-arylureido, N,N'-dialkylureido, N-alkyl-N'-arylureido, N-aryl-N'-alkylureido, N,N'-diarylureido, N,N',N'-trialkylureido, N,N'-dialkyl-N'-arylureido, N-alkyl-N',N'-diarylureido, N-aryl-N',N'-dialkyl ureido, N,N'-diaryl-N'-alkylureido. N,N',N'-triarylureido, amidino, alkylamidino, arylamidino, aminothiocarbonyl, alkylaminothiocarbonyl, arylaminothiocarbonyl, amino, aminoalkyl, alkylaminoalkyl, dialkylaminoalkyl, arylaminoalkyl, diarylaminoalkyl, alkylarylaminoalkyl, alkylamino, dialkylamino, haloalkylamino, arylamino, diarylamino, alkylarylamino, alkylcarbonylamino, alkoxycarbonylamino, aralkoxycarbonylamino, arylcarbonylamino, arylcarbonylaminoalkyl, aryloxycarbonylaminoalkyl, aryloxyarylcarbonylamino, aryloxycarbonylamino, alkylsulfonylamino, arylsulfonylamino, heteroarylsulfonylamino, heterocyclylsulfonylamino, heteroarylthio, azido, —N$^+$R$^{51}$R$^{52}$R$^{53}$, P(R$^{50}$)$_2$, P(=O)(R$^{50}$)$_2$, OP(=O)(R$^{50}$)$_2$, —NR$^{60}$C(=O)R$^{63}$, dialkylphosphonyl, alkylarylphosphonyl, diarylphosphonyl, hydroxyphosphonyl, alkylthio, arylthio, perfluoroalkylthio, hydroxycarbonylalkylthio, thiocyano, isothiocyano, alkylsulfinyloxy, alkylsulfonyloxy, arylsulfinyloxy, arylsulfonyloxy, hydroxysulfonyloxy, alkoxysulfonyloxy, aminosulfonyloxy, alkylaminosulfonyloxy, dialkylaminosulfonyloxy, arylaminosulfonyloxy, diarylaminosulfonyloxy, alkylarylaminosulfonyloxy, alkylsulfinyl, alkylsulfonyl, arylsulfinyl, arylsulfonyl, hydroxysulfonyl, alkoxysulfonyl, aminosulfonyl, alkylaminosulfonyl, dialkylaminosulfonyl, arylaminosulfonyl, diarylaminosulfonyl or alkylarylaminosulfonyl; or two Q$^2$ groups, which substitute atoms in a 1,2 or 1,3 arrangement, together form alkylene, alkylenoxy (i.e., —O—(CH$_2$)$_y$—), alkylenthioxy (i.e., —S—(CH$_2$)$_y$—), alkylenedioxy (i.e., —O—(CH$_2$)$_y$—O—), thioalkylenoxy (i.e., —S—(CH$_2$)$_y$—O—) or alkylenedithioxy (i.e., —S—(CH$_2$)$_y$—S—) where y is 1 or 2; or two Q$^2$ groups, which substitute the same atom, together form alkylene;

R$^{50}$ is hydroxy, alkoxy, aralkoxy, alkyl, heteroaryl, heterocyclyl, aryl or —NR$^{70}$R$^{71}$, where R$^{70}$ and R$^{71}$ are each independently hydrogen, alkyl, aralkyl, aryl, heteroaryl, heteroaralkyl or heterocyclyl, or R$^{70}$ and R$^{71}$ together form alkylene, azaalkylene, oxaalkylene or thiaalkylene;

R$^{51}$, R$^{52}$ and R$^{53}$ are each independently hydrogen, alkyl, aryl, aralkyl, heteroaryl, heteroaralkyl, heterocyclyl or heterocyclylalkyl;

R$^{60}$ is hydrogen, alkyl, aryl, aralkyl, heteroaryl, heteroaralkyl, heterocyclyl or heterocyclylalkyl; and R$^{63}$ is alkoxy, aralkoxy, alkyl, heteroaryl, heterocyclyl, aryl or —NR$^{70}$R$^{71}$.

In one embodiment, the compound provided herein is selected with a proviso that when R$^1$ is optionally substituted phenyl, pyridinyl or thienyl, then R$^3$-R$^7$ are other than methyl or chloro. In another embodiment, the compound provided herein is selected with a proviso that when R$^1$ is optionally substituted aryl or heteroaryl, then R$^3$-R$^7$ are other than methyl or chloro. In another embodiment, the compound provided herein is selected with a proviso that when R$^1$ is optionally substituted aryl or heteroaryl, then R$^3$-R$^7$ are other than alkyl or halo. In one embodiment, the compound provided herein is selected with a proviso that when R$^1$ is optionally substituted phenyl, pyridinyl or thienyl, then R$^3$-R$^7$ are other than alkyl or halo.

In one embodiment, the compound provided herein is selected with a proviso that when R$^1$ and R$^2$ are each hydrogen, then R$^5$ is other than H or chloro. In another embodiment, the compound provided herein is selected with a proviso that when R$^1$ and R$^2$ are each hydrogen, then R$^5$ is other than H or halo.

In one embodiment, the compound provided herein is selected with a proviso that when R$^2$ is benzyl, then R$^5$ is other than methoxy. In another embodiment, the compound provided herein is selected with a proviso that when R$^2$ is benzyl, then R$^5$ is other than alkoxy. In another embodiment, the compound provided herein is selected with a proviso that when R$^2$ is aralkyl, then R$^5$ is other than alkoxy. In one embodiment, the compound provided herein is selected with a proviso that when R$^2$ is aralkyl, then R$^5$ is other than methoxy.

In one embodiment, Q$^1$ is selected from one, two or three groups selected from alkyl, halo, alkoxy, hydroxy, haloalkoxy, haloalkyl, aryl, dialkylamino, or cycloalkyl. In one embodiment, Q$^1$ is selected from one, two or three groups selected from methyl, ethyl, isopropyl, propoxy, dimethylamino, chloro and fluoro.

In one embodiment, R$^1$ is selected from H, alkyl, alkenyl, alkynyl, aryl, cycloalkyl, heterocyclyl, heteroaryl, halo, pseudohalo, OR$^8$, C(O)R$^9$ and S(O)$_p$R$^9$. In another embodiment, R$^1$ is selected from H, alkyl, alkenyl, alkynyl, aryl and cycloalkyl. In another embodiment, R$^1$ is H or alkyl. In another embodiment, R$^1$ is H or lower alkyl. In another embodiment, R$^1$ is H.

In one embodiment, two R$^1$ groups together with the carbon atoms on which they are substituted form an optionally substituted aryl or heteroaryl ring. In one embodiment, two $R^1$ groups together with the carbon atoms on which they are substituted form an optionally substituted aryl ring. In one embodiment, two $R^1$ groups together with the carbon atoms on which they are substituted form an optionally substituted heteroaryl ring. In one embodiment, two $R^1$ groups together with the carbon atoms on which they are substituted form an optionally substituted benzene ring. In one embodiment, two $R^1$ groups together with the carbon atoms on which they are substituted form an optionally substituted pyridine ring.

In one embodiment, $R^2$ is selected from H, alkyl, alkenyl, alkynyl, aryl and cycloalkyl. In another embodiment, $R^2$ is H or alkyl. In another embodiment, $R^2$ is H or lower alkyl. In another embodiment, $R^2$ is H.

In one embodiment, $R^3$ and $R^7$ are each independently selected from H, alkyl alkenyl, alkynyl, aryl, cycloalkyl, heterocyclyl, heteroaryl, halo, pseudohalo, $OR^8$, $C(O)R^9$ and $S(O)_pR^9$. In another embodiment, $R^3$ and $R^7$ are each independently selected from H, hydroxy, alkyl, alkenyl, halo, aryl, haloaryl, dialkylaminoaryl, arylalkenyl, heterocyclyl, heteroaryl, alkoxy, cyano, aralkyl, $C(O)R^9$, aryloxy, cycloalkyl, cycloalkylalkyl, cycloalkylalkenyl, alkyloxyalkenyl, alkoxyalkyl, carboxyalkenyl and alkylcarbonyloxy.

In another embodiment, $R^3$ and $R^7$ are each independently selected from H, hydroxy, alkyl, halo, aryl, dialkylaminoaryl, heteroaryl, haloaryl, heterocyclyl, cycloalkyl, alkoxy, cyano, arylalkyl, alkylcarbonyl, aryloxy, cycloalkylalkenyl, alkoxyalkenyl, alkoxyalkyl and carboxyalkenyl.

In another embodiment, $R^3$ is selected from H, hydroxy, alkyl, halo, aryl, dialkylaminoaryl, heteroaryl, haloaryl and haloheteroaryl.

In another embodiment, $R^3$ is selected from H, methyl, phenyl, chloro, 4-dimethylaminophenyl, 2-chloropyridin-4-yl, piperidin-1-yl, pyrimidin-5-yl, hydroxy, 3-chlorophenyl, 3-fluorophenyl and t-butyl.

In another embodiment, $R^7$ is selected from H, hydroxy, cyano, alkyl, halo, aryl, haloaryl, heterocyclyl, heteroaryl, cycloalkyl, alkoxy, cyano, arylalkyl, arylalkenyl, alkylcarbonyl, aryloxy, cycloalkylalkenyl, alkoxyalkenyl, alkoxyalkyl and carboxyalkenyl.

In another embodiment, $R^7$ is selected from morpholinyl, bromo, chloro, fluoro, cyclopentyl, 4-chlorophenyl, 2-styryl, methoxy, hydroxy, cyano, phenethyl, acetoxy, methyl, ethyl, phenoxy, cyclopropylvinyl, 3-methoxyprop-1-enyl, propyl, cyclopropylethyl, pentyl, 3-methoxypropyl, furan-3-yl, vinyl and 2-carboxyvinyl.

In one embodiment, $R^4$ and $R^5$ are selected as follows:
a) $R^4$ and $R^5$ are each independently selected from H, alkyl, alkenyl, alkynyl, aryl, cycloalkyl, heterocyclyl, heteroaryl, halo, pseudohalo, $OR^8$, $C(O)R^9$ and $S(O)_pR^9$, or
b) $R^4$ and $R^5$ together with the carbon atoms on which they are substituted form an optionally substituted fused cycloalkyl or aryl ring, where the substituents, when present are selected from one or more, in one embodiment, one, two, three or four alkyl, haloalkyl and halo groups.

In one embodiment, $R^4$ is hydrogen or alkyl. In one embodiment. $R^4$ is hydrogen. In one embodiment. $R^5$ is selected from H, alkyl, halo, haloalkyl, heterocyclyl, alkenyl, alkynyl, aryl, cycloalkyl, heterocyclyl, heteroaryl, halo, pseudohalo. $OR^8$, $C(O)R^9$ and $S(O)_pR^9$. In one embodiment. $R^5$ is selected from H, alkyl, halo, haloalkyl, heterocyclyl, cycloalkyl, heteroaryl, and haloalkoxy. In one embodiment, $R^5$ is selected from H, fluoro, tert-butyl, tert-pentyl, trifluoromethyl, 4-morpholinyl, sec-butyl, isopropyl, butyl, 1-pyrrolidinyl, cyclohexyl, pyrazol-1-yl, cyclopentyl and trifluoromethoxy.

In one embodiment, $R^4$ and $R^5$ together with the carbon atoms on which they are substituted form a fused cycloalkyl or aryl ring optionally substituted with one, two, three or four alkyl groups. In one embodiment, $R^4$ and $R^5$ together with the carbon atoms on which they are substituted form a fused 5 or 6 membered cycloalkyl ring, optionally substituted with 1-4 methyl groups. In one embodiment, $R^4$ and $R^5$ together with the carbon atoms on which they are substituted form a fused 6 membered aryl ring, optionally substituted with 1-4 methyl groups. In one embodiment, $R^4$ and $R^5$ together with the carbon atoms on which they are substituted form a fused 6 membered aryl ring.

In one embodiment, $R^6$ is selected from H, aryl, alkylaryl, alkoxyaryl and alkyl. In one embodiment, $R^6$ is selected from H, methyl, phenyl, 2,6-dimethylphenyl, 3,5-dimethylphenyl, 2-isopropylphenyl, 2-propoxyphenyl and 2-ethylphenyl.

In one embodiment, $R^8$ is hydrogen or alkyl. In one embodiment, $R^8$ is hydrogen. In one embodiment, $R^9$ is hydrogen or alkyl. In one embodiment, $R^9$ is hydrogen.

In one embodiment, n is 0, 1 or 2. In one embodiment, n is 0. In one embodiment, n is 1. In one embodiment, n is 2. In one embodiment, p is 0, 1 or 2. In one embodiment, p is 0. In one embodiment, p is 1. In one embodiment, p is 2.

In one embodiment, the compound is of formula II:

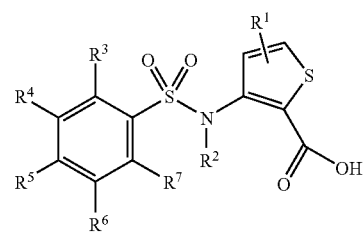

II or a pharmaceutically acceptable derivative thereof, wherein the variables are as described herein.

In one embodiment, the compound is of formula III:

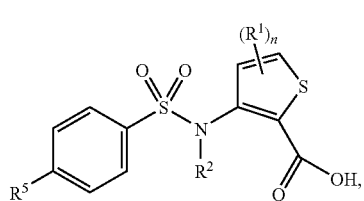

III or a pharmaceutically acceptable derivative thereof, wherein n is 0 or 1 and other variables are as described elsewhere herein. In one embodiment, $R^5$ is alkyl. In one embodiment $R^5$ is tert-butyl.

In one embodiment, the compounds provided herein have formula IV:

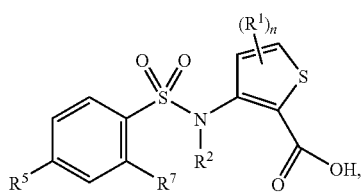

IV or pharmaceutically acceptable derivatives thereof, wherein the variables are as described elsewhere herein.

In one embodiment, the compound is of formula V:

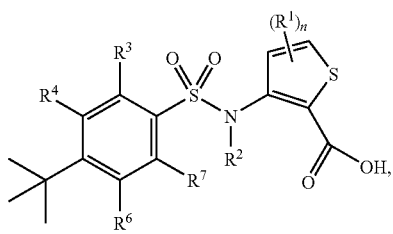

V or a pharmaceutically acceptable derivative thereof, wherein the variables are as described elsewhere herein.

In one embodiment, the compound is of formula VA:

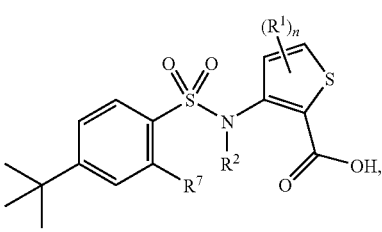

VA or a pharmaceutically acceptable derivative thereof, wherein the variables are as described elsewhere herein.

In one embodiment, the compound is of formula VI or VII:

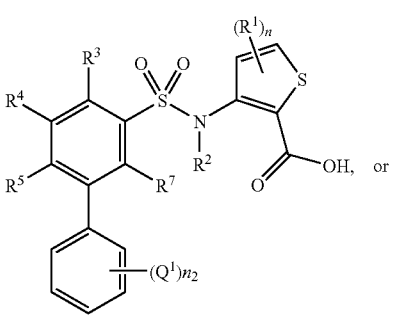

VI

VII

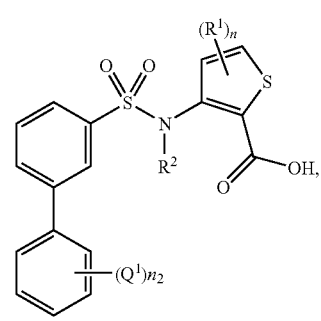

or a pharmaceutically acceptable derivative thereof, wherein the variables are as described elsewhere herein. In one embodiment. $Q^1$ is selected from hydrogen, alkyl or alkoxy.

In one embodiment, $Q^1$ is selected from hydrogen, methyl, ethyl, isopropyl or propoxy. In one embodiment, $n_2$ is 1 or 2. In one embodiment, $n_2$ is 1.

In one embodiment, the compound is of formula VIII:

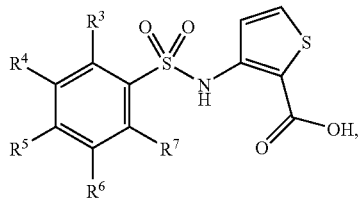

VIII or a pharmaceutically acceptable derivative thereof, wherein the variables are as described elsewhere herein.

In one embodiment, the compound is of formula IXA or IXB:

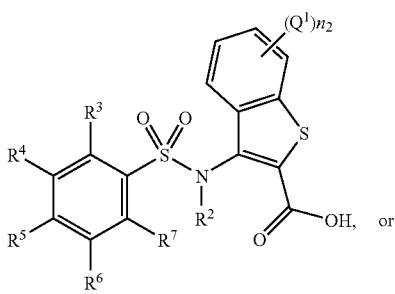

IXA

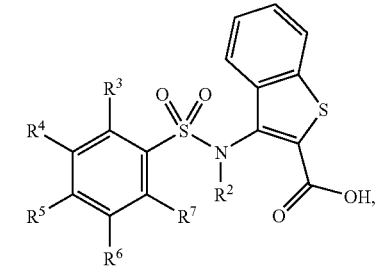

IXB or a pharmaceutically acceptable derivative thereof, wherein the variables are as described elsewhere herein. In one embodiment, $Q^1$ is halo. In one embodiment, $Q^1$ is fluoro.

In one embodiment, the compound is of formula XA or XB:

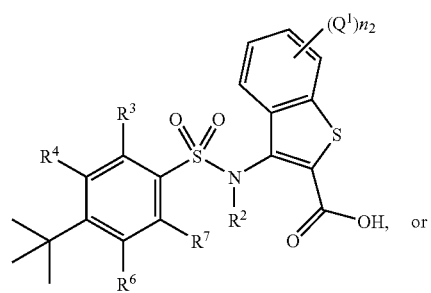

XA

-continued

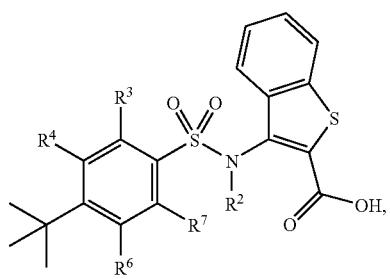
XB or a pharmaceutically acceptable derivative thereof, wherein the variables are as described elsewhere herein.

In one embodiment, the compound is of formula XIA or XIB:

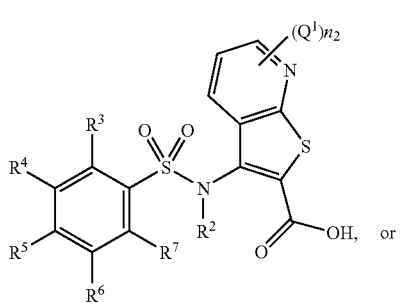
XIA

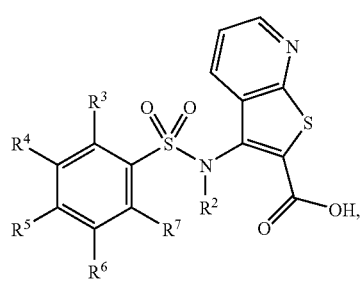
XIB or a pharmaceutically acceptable derivative thereof, wherein the variables are as described elsewhere herein. In one embodiment, $Q^1$ is halo. In one embodiment $Q^1$ is fluoro.

In one embodiment, the compound is of formula XIIA or XIIB:

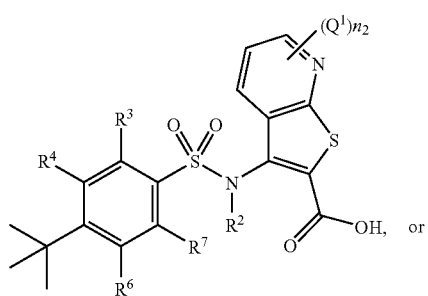
XIIA

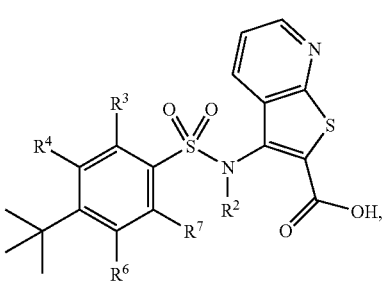
VIIB or a pharmaceutically acceptable derivative thereof the variables are as described elsewhere herein.

5.2.1 Preparation of the Compounds

The compounds provided herein can be prepared by routine chemical reactions known to one of skill in the art. General schemes for preparation of exemplary compounds are illustrated below:

SCHEME 1

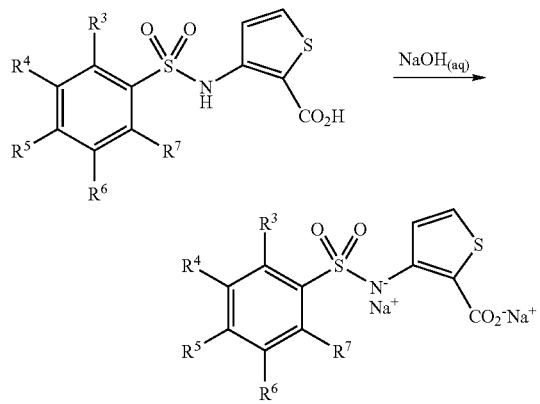

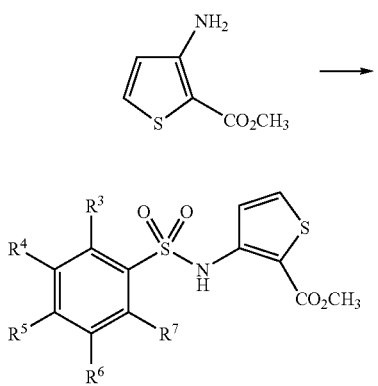

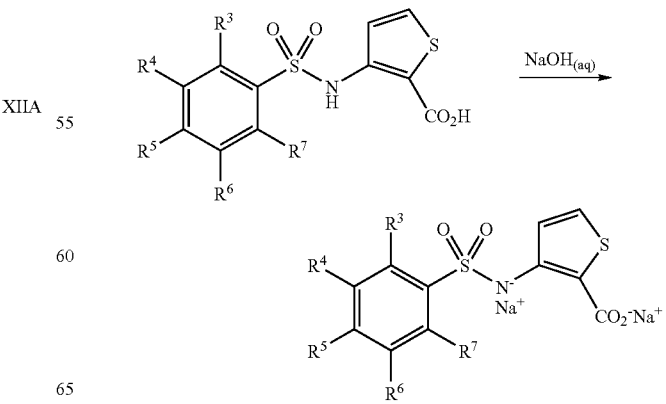

SCHEME 2

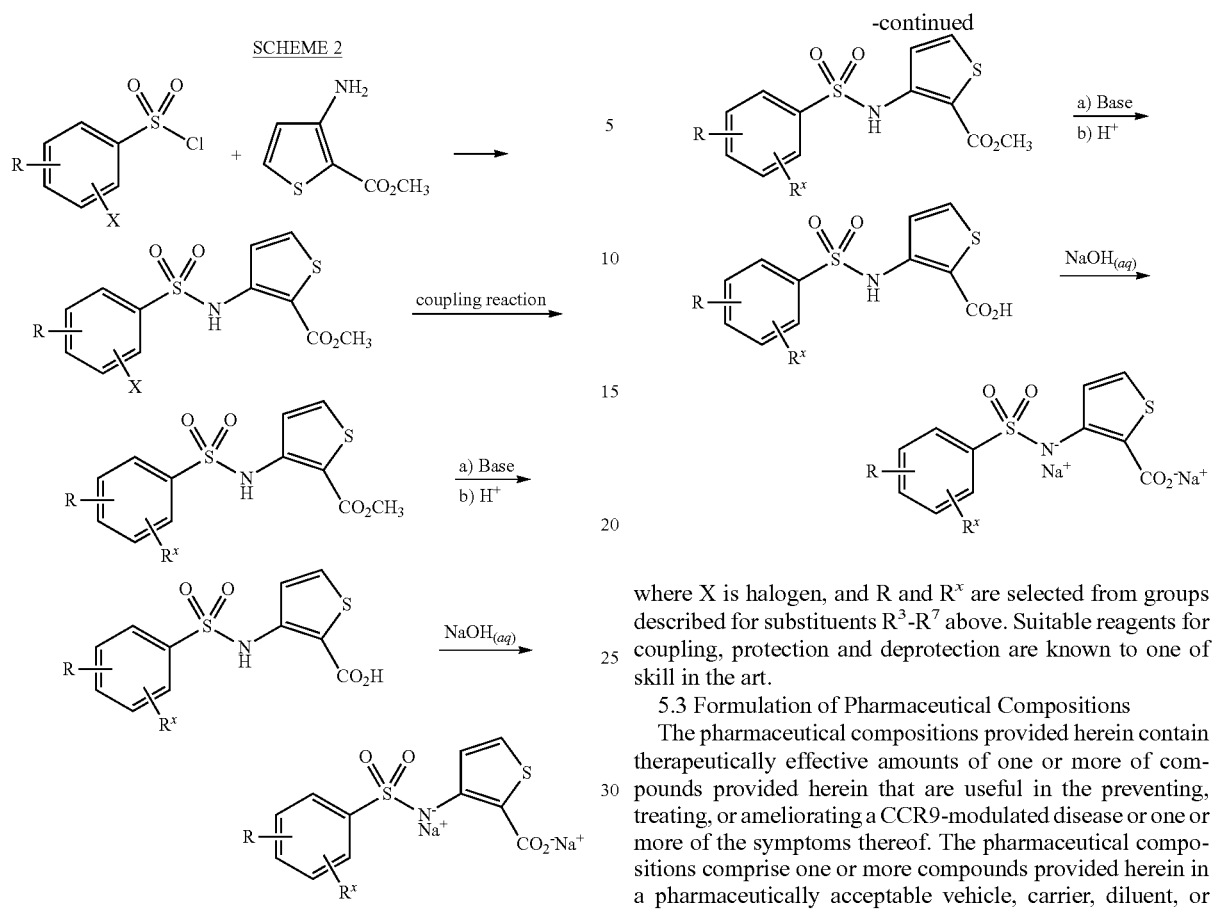

-continued where X is halogen, and R and $R^x$ are selected from groups described for substituents $R^3$-$R^7$ above. Suitable reagents for coupling, protection and deprotection are known to one of skill in the art.

5.3 Formulation of Pharmaceutical Compositions

The pharmaceutical compositions provided herein contain therapeutically effective amounts of one or more of compounds provided herein that are useful in the preventing, treating, or ameliorating a CCR9-modulated disease or one or more of the symptoms thereof. The pharmaceutical compositions comprise one or more compounds provided herein in a pharmaceutically acceptable vehicle, carrier, diluent, or excipient, or a mixture thereof.

In one embodiment, provided herein are pharmaceutical compositions in modified release dosage forms, which comprise a compound of Formula I or a pharmaceutically acceptable derivative thereof, and one or more release controlling excipients as described herein. Suitable modified release dosage vehicles include, but are not limited to, hydrophilic or hydrophobic matrix devices, water-soluble separating layer coatings, enteric coatings, osmotic devices, multiparticulate devices, and combinations thereof. The pharmaceutical compositions may also comprise non-release controlling excipients.

Further provided herein are pharmaceutical compositions in enteric coated do sage forms, which comprise a compound of Formula I or a pharmaceutically acceptable derivative thereof, and one or more release controlling excipients for use in an enteric coated dosage form. The pharmaceutical compositions may also comprise non-release controlling excipients.

Additionally provided are pharmaceutical compositions in a dosage form that has an instant releasing component and at least one delayed releasing component, and is capable of giving a discontinuous release of the compound in the form of at least two consecutive pulses separated in time from 0.1 up to 24 hours. The pharmaceutical compositions comprise a compound of Formula I or a pharmaceutically acceptable derivative thereof, and one or more release controlling and non-release controlling excipients, such as those excipients suitable for a disruptable semi-permeable membrane and as swellable substances.

In certain embodiments, provided herein are pharmaceutical compositions in a dosage form for oral administration to a subject, which comprise a compound of Formula I or a pharwhere X is halogen, and R and $R^x$ selected from groups described for substituents $R^3$-$R^7$ above.

SCHEME 3

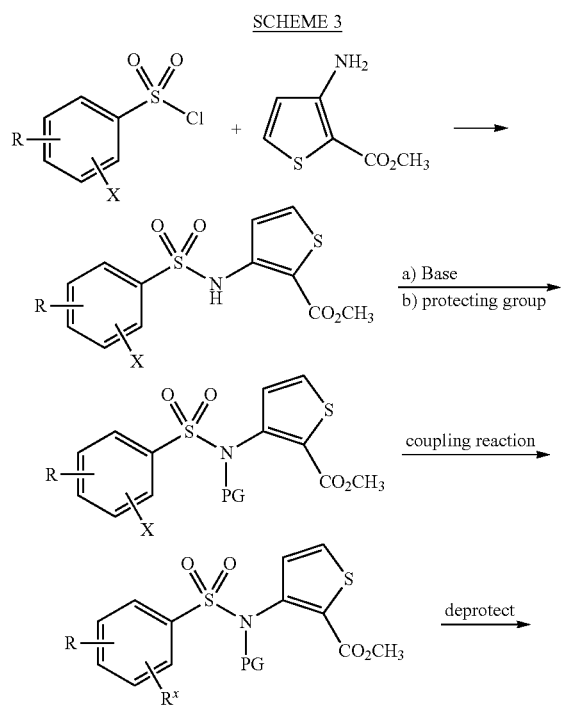

maceutically acceptable derivative thereof, and one or more pharmaceutically acceptable excipients or carriers, enclosed in an intermediate reactive layer comprising a gastric juice-resistant polymeric layered material partially neutralized with alkali and having cation exchange capacity and a gastric juice-resistant outer layer.

In one embodiment, the pharmaceutical compositions herein may be provided in unit-dosage forms or multiple-dosage forms. Unit-dosage forms, as used herein, refer to physically discrete units suitable for administration to human and animal subjects and packaged individually as is known in the art. Each unit-dose contains a predetermined quantity of the active ingredient(s) sufficient to produce the desired therapeutic effect, in association with the required pharmaceutical carriers or excipients. Examples of unit-dosage forms include ampouls, syringes, and individually packaged tablets and capsules. Unit-dosage forms may be administered in fractions or multiples thereof. A multiple-dosage form is a plurality of identical unit-dosage forms packaged in a single container to be administered in segregated unit-dosage form. Examples of multiple-dosage forms include vials, bottles of tablets or capsules, or bottles of pints or gallons.

The compound of Formula I provided herein may be administered alone, or in combination with one or more other compounds provided herein, one or more other active ingredients. The pharmaceutical compositions that comprise a compound provided herein may be formulated in various dosage forms for oral, parenteral, and topical administration. The pharmaceutical compositions may also be formulated as modified release dosage forms, including delayed-, extended-, prolonged-, sustained-, pulsatile-, controlled-, accelerated- and fast-, targeted-, programmed-release, and gastric retention dosage forms. These dosage forms can be prepared according to conventional methods and techniques known to those skilled in the art (see, *Remington: The Science and Practice of Pharmacy*, supra; *Modified-Release Drug Deliver Technology*, Rathbone et al., Eds., Drugs and the Pharmaceutical Science, Marcel Dekker, Inc.: New York, N.Y., 2002; Vol. 126).

The pharmaceutical compositions provided herein may be administered at once, or multiple times at intervals of time. It is understood that the precise dosage and duration of treatment may vary with the age, weight, and condition of the patient being treated, and may be determined empirically using known testing protocols or by extrapolation from in vivo or in vitro test or diagnostic data. It is further understood that for any particular individual, specific dosage regimens should be adjusted over time according to the individual need and the professional judgment of the person administering or supervising the administration of the formulations.

A. Oral Administration

The pharmaceutical compositions provided herein may be provided in solid, semisolid, or liquid dosage forms for oral administration. As used herein, oral administration also includes buccal, lingual, and sublingual administration. Suitable oral dosage forms include, but are not limited to, tablets, capsules, pills, troches, lozenges, pastilles, cachets, pellets, medicated chewing gum, granules, bulk powders, effervescent or non-effervescent powders or granules, solutions, emulsions, suspensions, solutions, wafers, sprinkles, elixirs, and syrups. In addition to the active ingredient(s), the pharmaceutical compositions may contain one or more pharmaceutically acceptable carriers or excipients, including, but not limited to, binders, fillers, diluents, disintegrants, wetting agents, lubricants, glidants, coloring agents, dye-migration inhibitors, sweetening agents, and flavoring agents.

Binders or granulators impart cohesiveness to a tablet to ensure that the tablet remains intact after compression. Suitable binders or granulators include, but are not limited to, starches, such as corn starch, potato starch, and pre-gelatinized starch (e.g., STARCH 1500); gelatin; sugars, such as sucrose, glucose, dextrose, molasses, and lactose; natural and synthetic gums, such as acacia, alginic acid, alginates, extract of Irish moss, Panwar gum, ghatti gum, mucilage of isabgol husks, carboxymethylcellulose, methylcellulose, polyvinylpyrrolidone (PVP), Veegum, larch arabogalactan, powdered tragacanth and guar gum; celluloses, such as ethyl cellulose, cellulose acetate, carboxymethyl cellulose calcium, sodium carboxymethyl cellulose, methyl cellulose, hydroxyethylcellulose (HEC), hydroxypropylcellulose (HPC), hydroxypropyl methyl cellulose (HPMC); microcrystalline celluloses, such as AVICEL-PH-101, AVICEL-PH-103, AVICEL RC-581, AVICEL-PH-105 (FMC Corp., Marcus Hook, Pa.); and mixtures thereof. Suitable fillers include, but are not limited to, talc, calcium carbonate, microcrystalline cellulose, powdered cellulose, dextrates, kaolin, mannitol, silicic acid, sorbitol, starch, pre-gelatinized starch, and mixtures thereof. The binder or filler may be present from about 50 to about 99% by weight in the pharmaceutical compositions provided herein.

Suitable diluents include, but are not limited to, dicalcium phosphate, calcium sulfate, lactose, sorbitol, sucrose, inositol, cellulose, kaolin, mannitol, sodium chloride, dry starch, and powdered sugar. Certain diluents, such as mannitol, lactose, sorbitol, sucrose, and inositol, when present in sufficient quantity, can impart properties to some compressed tablets that permit disintegration in the mouth by chewing. Such compressed tablets can be used as chewable tablets.

Suitable disintegrants include, but are not limited to, agar; bentonite; celluloses, such as methylcellulose and carboxymethylcellulose; wood products; natural sponge; cation-exchange resins; alginic acid; gums, such as guar gum and Veegum HV; citrus pulp; cross-linked celluloses, such as croscarmellose; cross-linked polymers, such as crospovidone; cross-linked starches; calcium carbonate; microcrystalline cellulose, such as sodium starch glycolate; polacrilin potassium; starches, such as corn starch, potato starch, tapioca starch, and pre-gelatinized starch; clays; aligns; and mixtures thereof. The amount of disintegrant in the pharmaceutical compositions provided herein varies upon the type of formulation, and is readily discernible to those of ordinary skill in the art. The pharmaceutical compositions provided herein may contain from about 0.5 to about 15% or from about 1 to about 5% by weight of a disintegrant.

Suitable lubricants include, but are not limited to, calcium stearate; magnesium stearate; mineral oil; light mineral oil; glycerin; sorbitol; mannitol; glycols, such as glycerol behenate and polyethylene glycol (PEG); stearic acid; sodium lauryl sulfate; talc; hydrogenated vegetable oil, including peanut oil, cottonseed oil, sunflower oil, sesame oil, olive oil, corn oil, and soybean oil; zinc stearate; ethyl oleate; ethyl laureate; agar; starch, lycopodium; silica or silica gels, such as AEROSIL® 200 (W. R. Grace Co., Baltimore. Md.) and CAB-O-SIL® (Cabot Co. of Boston, Mass.); and mixtures thereof. The pharmaceutical compositions provided herein may contain about 0.1 to about 5 by weight of a lubricant.

Suitable glidants include colloidal silicon dioxide, CAB-O-SIL® (Cabot Co. of Boston, Mass.), and asbestos-free talc. Coloring agents include any of the approved, certified, water soluble FD&C dyes, and water insoluble FD&C dyes suspended on alumina hydrate, and color lakes and mixtures thereof. A color lake is the combination by adsorption of a water-soluble dye to a hydrous oxide of a heavy metal, resulting in an insoluble form of the dye. Flavoring agents include natural flavors extracted from plants, such as fruits, and synthetic blends of compounds which produce a pleasant taste sensation, such as peppermint and methyl salicylate. Sweetening agents include sucrose, lactose, mannitol, syrups, glycerin, and artificial sweeteners, such as saccharin and aspartame. Suitable emulsifying agents include gelatin, acacia, tragacanth, bentonite, and surfactants, such as polyoxyethylene sorbitan monooleate (TWEEN® 20), polyoxyethylene sorbitan monooleate 80 (TWEEN® 80), and triethanolamine oleate. Suspending and dispersing agents include sodium carboxymethylcellulose, pectin, tragacanth, Veegum, acacia, sodium carbomethylcellulose, hydroxypropyl methylcellulose, and polyvinylpyrolidone. Preservatives include glycerin, methyl and propylparaben, benzoic add, sodium benzoate and alcohol. Wetting agents include propylene glycol monostearate, sorbitan monooleate, diethylene glycol monolaurate, and polyoxyethylene lauryl ether. Solvents include glycerin, sorbitol, ethyl alcohol, and syrup. Examples of non-aqueous liquids utilized in emulsions include mineral oil and cottonseed oil. Organic acids include citric and tartaric acid. Sources of carbon dioxide include sodium bicarbonate and sodium carbonate.

It should be understood that many carriers and excipients may serve several functions, even within the same formulation.

The pharmaceutical compositions provided herein may be provided as compressed tablets, tablet triturates, chewable lozenges, rapidly dissolving tablets, multiple compressed tablets, or enteric-coating tablets, sugar-coated, or film-coated tablets. Enteric-coated tablets are compressed tablets coated with substances that resist the action of stomach acid but dissolve or disintegrate in the intestine, thus protecting the active ingredients from the acidic environment of the stomach. Enteric-coatings include, but are not limited to fatty acids, fats, phenylsalicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets.

The tablet dosage forms may be prepared from the active ingredient in powdered, crystalline, or granular forms, alone or in combination with one or more carriers or excipients described herein, including binders, disintegrants, controlled-release polymers, lubricants, diluents, and/or colorants. Flavoring and sweetening agents are especially useful in the formation of chewable tablets and lozenges.

The pharmaceutical compositions provided herein may be provided as soft or hard capsules, which can be made from gelatin, methylcellulose, starch, or calcium alginate. The hard gelatin capsule, also known as the dry-filled capsule (DFC), consists of two sections, one slipping over the other, thus completely enclosing the active ingredient. The soft elastic capsule (SEC) is a soft, globular shell, such as a gelatin shell, which is plasticized by the addition of glycerin, sorbitol, or a similar polyol. The soft gelatin shells may contain a preservative to prevent the growth of microorganisms. Suitable preservatives are those as described herein, including methyl- and propyl-parabens, and sorbic acid. The liquid, semisolid, and solid dosage forms provided herein may be encapsulated in a capsule. Suitable liquid and semisolid dosage forms include solutions and suspensions in propylene carbonate, vegetable oils, or triglycerides. Capsules containing such solutions can be prepared as described in U.S. Pat. Nos. 4,328,245; 4,409,239; and 4,410,545. The capsules may also be coated as known by those of skill in the art in order to modify or sustain dissolution of the active ingredient.

The pharmaceutical compositions provided herein may be provided in liquid and semisolid dosage forms, including emulsions, solutions, suspensions, elixirs, and syrups. An emulsion is a two-phase system, in which one liquid is dispersed in the form of small globules throughout another liquid, which can be oil-in-water or water-in-oil. Emulsions may include a pharmaceutically acceptable non-aqueous liquids or solvent, emulsifying agent, and preservative. Suspensions may include a pharmaceutically acceptable suspending agent and preservative. Aqueous alcoholic solutions may include a pharmaceutically acceptable acetal, such as a di(lower alkyl) acetal of a lower alkyl aldehyde. e.g., acetaldehyde diethyl acetal; and a water-miscible solvent having one or more hydroxyl groups, such as propylene glycol and ethanol. Elixirs are clear, sweetened, and hydroalcoholic solutions. Syrups are concentrated aqueous solutions of a sugar for example, sucrose, and may also contain a preservative. For a liquid dosage form, for example, a solution in a polyethylene glycol may be diluted with a sufficient quantity of a pharmaceutically acceptable liquid carrier, e.g., water, to be measured conveniently for administration.

Other useful liquid and semisolid dosage forms include, but are not limited to, those containing the active ingredient(s) provided herein, and a dialkylated mono- or poly-alkylene glycol, including, 1,2-dimethoxymethane, diglyme, triglyme, tetraglyme, polyethylene glycol-350-dimethyl ether, polyethylene glycol-550-dimethyl ether, polyethylene glycol-750-dimethyl ether, wherein 350, 550, and 750 refer to the approximate average molecular weight of the polyethylene glycol. These formulations may further comprise one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, bisulfite, sodium metabisulfite, thiodipropionic acid and its esters, and dithiocarbamates.

The pharmaceutical compositions provided herein for oral administration may be also provided in the forms of liposomes, micelles, microspheres, or nanosystems. Micellar dosage forms can be prepared as described in U.S. Pat. No. 6,350,458.

The pharmaceutical compositions provided herein may be provided as non-effervescent or effervescent, granules and powders, to be reconstituted into a liquid dosage form. Pharmaceutically acceptable carriers and excipients used in the non-effervescent granules or powders may include diluents, sweeteners, and wetting agents. Pharmaceutically acceptable carriers and excipients used in the effervescent granules or powders may include organic acids and a source of carbon dioxide.

Coloring and flavoring agents can be used in all of the above dosage forms.

The pharmaceutical compositions provided herein may be formulated as immediate or modified release dosage forms, including delayed-, sustained, pulsed-, controlled, targeted-, and programmed-release forms.

The pharmaceutical compositions provided herein may be co-formulated with other active ingredients which do not impair the desired therapeutic action, or with substances that supplement the desired action, such as antacids, proton pump inhibitors, and H₂-receptor antagonists.

B. Parenteral Administration

The pharmaceutical compositions provided herein may be administered parenterally by injection, infusion or implantation, for local or systemic administration. Parenteral administration, as used herein, include intravenous, intraarterial, intraperitoneal, intrathecal, intraventricular, intraurethral, intrasternal, intracranial, intramuscular, intrasynovial, and subcutaneous administration.

The pharmaceutical compositions provided herein may be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science (see, *Remington, The Science and Practice of Pharmacy*, supra).

The pharmaceutical compositions intended for parenteral administration may include one or more pharmaceutically acceptable carriers and excipients, including, but not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

Suitable aqueous vehicles include, but are not limited to, water, saline, physiological saline or phosphate buffered saline (PBS), sodium chloride injection, Ringers injection, isotonic dextrose injection, sterile water injection, dextrose and lactated Ringers injection. Non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, and palm seed oil. Water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, dimethylacetamide, and dimethylsulfoxide.

Suitable antimicrobial agents or preservatives include, but are not limited to, phenols, cresols, mercurials, benzyl alcohol, chlorobutanol, methyl and propyl p-hydroxybenzates, thimerosal, benzalkonium chloride, benzethonium chloride, methyl- and propyl-parabens, and sorbic acid. Suitable isotonic agents include, but are not limited to, sodium chloride, glycerin, and dextrose. Suitable buffering agents include, but are not limited to, phosphate and citrate. Suitable antioxidants are those as described herein, including bisulfite and sodium mnetabisulfite. Suitable local anesthetics include, but are not limited to, procaine hydrochloride. Suitable suspending and dispersing agents are those as described herein, including sodium carboxymethylceluose, hydroxypropyl methylcellulose, and polyvinylpyrrolidone. Suitable emulsifying agents include those described herein, including polyoxyethylene sorbitan monolaurate, polyoxyethylene sorbitan monooleate 80, and triethanolamine oleate. Suitable sequestering or chelating agents include, but are not limited to EDTA. Suitable pH adjusting agents include, but are not limited to, sodium hydroxide, hydrochloric acid, citric acid, and lactic acid. Suitable complexing agents include, but are not limited to, cyclodextrins, including alpha-cyclodextrin, beta-cyclodextrin, hydroxypropyl-beta-cyclodextrin, sulfobutylether-beta-cyclodextrin, and sulfobutylether 7-beta-cyclodextrin (CAPTISOL®, CyDex, Lenexa, Kans.).

The pharmaceutical compositions provided herein may be formulated for single or multiple dosage administration. The single dosage formulations are packaged in an ampule, a vial, or a syringe. The multiple dosage parenteral formulations must contain an antimicrobial agent at bacteriostatic or fungistatic concentrations. All parenteral formulations must be sterile, as known and practiced in the art.

In one embodiment, the pharmaceutical compositions are provided as ready-to-use sterile solutions. In another embodiment, the pharmaceutical compositions are provided as sterile dry soluble products, including lyophilized powders and hypodermic tablets, to be reconstituted with a vehicle prior to use. In yet another embodiment, the pharmaceutical compositions are provided as ready-to-use sterile suspensions. In yet another embodiment, the pharmaceutical compositions are provided as sterile dry insoluble products to be reconstituted with a vehicle prior to use. In still another embodiment, the pharmaceutical compositions are provided as ready-to-use sterile emulsions.

The pharmaceutical compositions provided herein may be formulated as immediate or modified release dosage forms, including delayed-, sustained, pulsed-, controlled, targeted-, and programmed-release forms.

The pharmaceutical compositions may be formulated as a suspension, solid, semi-solid, or thixotropic liquid, for administration as an implanted depot. In one embodiment, the pharmaceutical compositions provided herein are dispersed in a solid inner matrix, which is surrounded by an outer polymeric membrane that is insoluble in body fluids but allows the active ingredient in the pharmaceutical compositions diffuse through.

Suitable inner matrixes include polymethylmethacrylate, polybutylmethacrylate, plasticized or unplasticized polyvinylchloride, plasticized nylon, plasticized polyethyveneterephthalate, natural rubber, polyisoprene, polyisobutylene polybutadiene, polyethylene, ethylene-vinylacetate copolymers, silicone rubbers, polydimethylsiloxanes, silicone carbonate copolymers, hydrophilic polymers, such as hydrogels of esters of acrylic and methacrylic acid, collagen, cross-linked polyvinylalcohol, and cross-linked partially hydrolyzed polyvinyl acetate.

Suitable outer polymeric membranes include polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinyl-chloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer.

C. Topical Administration

The pharmaceutical compositions provided herein may be administered topically to the skin, orifices, or mucosa. The topical administration, as used herein, include (intra)dermal, conjuctival, intracorneal, intraocular, ophthalmic, auricular, transdermal, nasal, vaginal, uretheral, respiratory, and rectal administration.

The pharmaceutical compositions provided herein may be formulated in any dosage forms that are suitable for topical administration for local or systemic effect, including emulsions, solutions, suspensions, creams, gels, hydrogels, ointments, dusting powders, dressings, elixirs, lotions, suspensions, tinctures, pastes, foams, films, aerosols, irrigations, sprays, suppositories, bandages, dermal patches. The topical formulation of the pharmaceutical compositions provided herein may also comprise liposomes, micelles, microspheres, nanosystems, and mixtures thereof.

Pharmaceutically acceptable carriers and excipients suitable for use in the topical formulations provided herein include, but are not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, penetration enhancers, cryoprotectants, lyoprotectants, thickening agents, and inert gases.

The pharmaceutical compositions may also be administered topically by electroporation, iontophoresis, phonophoresis, sonophoresis and microneedle or needle-free injection, such as POWDEREJECT™ (Chiron Corp., Emeryville, Calif.), and BIOJECT™ (Bioject Medical Technologies Inc., Tualatin, Oreg.).

The pharmaceutical compositions provided herein may be provided in the forms of ointments, creams, and gels. Suitable ointment vehicles include oleaginous or hydrocarbon bases, including such as lard, benzoinated lard, olive oil, cottonseed oil, and other oils, white petrolatum; emulsifiable or absorption bases, such as hydrophilic petrolatum, hydroxystearin sulfate, and anhydrous lanolin; water-removable bases, such as hydrophilic ointment; water-soluble ointment bases, including polyethylene glycols of varying molecular weight; emulsion bases, either water-in-oil (W/O) emulsions or oil-in-water (O/W) emulsions, including cetyl alcohol, glyceryl monostearate, lanolin, and stearic acid (see, *Remington: The Science and Practice of Pharmacy*, supra). These vehicles are emollient but generally require addition of antioxidants and preservatives.

Suitable cream base can be oil-in-water or water-in-oil. Cream vehicles may be water-washable, and contain an oil phase, an emulsifier, and an aqueous phase. The oil phase is also called the "internal" phase, which is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation may be a nonionic, anionic, cationic, or amphoteric surfactant.

Gels are semisolid, suspension-type systems. Single-phase gels contain organic macromolecules distributed substantially uniformly throughout the liquid carrier. Suitable gelling agents include crosslinked acrylic acid polymers, such as carbomers, carboxypolyalkylenes, Carbopol®; hydrophilic polymers, such as polyethylene oxides, polyoxyethylene-polyoxypropylene copolymers, and polyvinylalcohol; cellulosic polymers, such as hydroxypropyl cellulose, hydroxyethyl cellulose, hydroxypropyl methylcellulose, hydroxypropyl methylcellulose phthalate, and methylcellulose; gums, such as tragacanth and xanthan gum; sodium alginate; and gelatin. In order to prepare a uniform gel dispersing agents such as alcohol or glycerin can be added, or the gelling agent can be dispersed by trituration, mechanical mixing, and/or stirring.

The pharmaceutical compositions provided herein may be administered rectally, urethrally, vaginally, or perivaginally in the forms of suppositories, pessaries, bougies, poultices or cataplasm, pastes, powders, dressings, creams, plasters, contraceptives, ointments, solutions, emulsions, suspensions, tampons, gels, foams, sprays, or enemas. These dosage forms can be manufactured using conventional processes as described in *Remington: The Science and Practice of Pharmacy*, supra.

Rectal, urethral and vaginal suppositories are solid bodies for insertion into body orifices, which are solid at ordinary temperatures but melt or soften at body temperature to release the active ingredient(s) inside the orifices. Pharmaceutically acceptable carriers utilized in rectal and vaginal suppositories include vehicles, such as stiffening agents, which produce a melting point in the proximity of body temperature, when formulated with the pharmaceutical compositions provided herein; and antioxidants as described herein, including bisulfite and sodium metabisulfite. Suitable vehicles include, but are not limited to, cocoa butter (theobroma oil), glycerin-gelatin, carbowax (polyoxyethylene glycol), spermaceti, paraffin, white and yellow wax, and appropriate mixtures of mono-, di- and triglycerides of fatty acids, hydrogels, such as polyvinyl alcohol, hydroxyethyl methacrylate, polyacrylic acid; glycerinated gelatin. Combinations of the various vehicles may be used. Rectal and vaginal suppositories may be prepared by the compressed method or molding. The typical weight of a rectal and vaginal suppository is about 2 to 3 g.

The pharmaceutical compositions provided herein may be administered ophthalmically in the forms of solutions, suspensions, ointments, emulsions, gel-forming solutions, powders for solutions, gels, ocular inserts, and implants.

The pharmaceutical compositions provided herein may be administered intranasally or by inhalation to the respiratory tract. The pharmaceutical compositions may be provided in the form of an aerosol or solution for delivery using a pressurized container, pump, spray, atomizer, such as an atomizer using electrohydrodynamics to produce a fine mist, or nebulizer, alone or in combination with a suitable propellant, such as 1,1,1,2-tetrafluoroethane or 1,1,1,2,3,3,3-heptafluoropropane. The pharmaceutical compositions may also be provided as a dry powder for insufflation, alone or in combination with an inert carrier such as lactose or phospholipids; and nasal drops. For intranasal use, the powder may comprise a bioadhesive agent, including chitosan or cyclodextrin.

Solutions or suspensions for use in a pressurized container, pump, spray, atomizer, or nebulizer may be formulated to contain ethanol, aqueous ethanol, or a suitable alternative agent for dispersing, solubilizing, or extending release of the active ingredient provided herein, a propellant as solvent; and/or a surfactant, such as sorbitan trioleate, oleic acid, or an oligolactic acid.

The pharmaceutical compositions provided herein may be micronized to a size suitable for delivery by inhalation, such as 50 micrometers or less, or 10 micrometers or less. Particles of such sizes may be prepared using a comminuting method known to those skilled in the art, such as spiral jet milling fluid bed jet milling, supercritical fluid processing to form nanoparticles, high pressure homogenization, or spray drying.

Capsules, blisters and cartridges for use in an inhaler or insufflator may be formulated to contain a powder mix of the pharmaceutical compositions provided herein; a suitable powder base, such as lactose or starch; and a performance modifier, such as l-leucine, mannitol, or magnesium stearate. The lactose may be anhydrous or in the form of the monohydrate. Other suitable excipients include dextran, glucose, maltose, sorbitol, xylitol, fructose, sucrose, and trehalose. The pharmaceutical compositions provided herein for inhaled/intranasal administration may further comprise a suitable flavor, such as menthol and levomenthol, or sweeteners, such as saccharin or saccharin sodium.

The pharmaceutical compositions provided herein for topical administration may be formulated to be immediate release or modified release, including delayed-, sustained-, pulsed-, controlled-, targeted, and programmed release.

D. Modified Release

The pharmaceutical compositions provided herein may be formulated as a modified release dosage form. As used herein, the term "modified release" refers to a dosage form in which the rate or place of release of the active ingredient(s) is different from that of an immediate dosage form when administered by the same route. Modified release dosage forms include delayed-, extended-, prolonged-, sustained-, pulsatile- or pulsed-, controlled-, accelerated- and fast-, targeted-, programmed-release, and gastric retention dosage forms. The pharmaceutical compositions in modified release dosage forms can be prepared using a variety of modified release devices and methods known to those skilled in the art, including, but not limited to, matrix controlled release devices, osmotic controlled release devices, multiparticulate controlled release devices, ion-exchange resins, enteric coatings, multilayered coatings, microspheres, liposomes, and combinations thereof. The release rate of the active ingredient(s) can also be modified by varying the particle sizes and polymorphism of the active ingredient(s).

Examples of modified release include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,972,891; 5,980,945; 5,993,855; 6,045,830; 6,087,324; 6,113,943; 6,197,350; 6,248,363; 6,264,970; 6,267,981; 6,376,461; 6,419,961; 6,589,548; 6,613,358; and 6,699,500.

1. Matrix Controlled Release Devices

The pharmaceutical compositions provided herein in a modified release dosage form may be fabricated using a matrix controlled release device known to those skilled in the art (see, Takada et al in "Encyclopedia of Controlled Drug Delivery," Vol. 2, Mathiowitz ed., Wiley, 1999).

In one embodiment, the pharmaceutical compositions provided herein in a modified release dosage form is formulated using an erodible matrix device, which is water-swellable, erodible, or soluble polymers, including synthetic polymers, and naturally occurring polymers and derivatives, such as polysaccharides and proteins.

Materials useful in forming an erodible matrix include, but are not limited to, chitin, chitosan, dextran, and pullulan; gum agar, gum arabic, gum karaya, locust bean gum, gum tragacanth, carrageenans, gum ghatti, guar gum, xanthan gum, and scleroglucan; starches, such as dextrin and maltodextrin; hydrophilic colloids, such as pectin; phosphatides, such as lecithin; alginates; propylene glycol alginate; gelatin; collagen; and cellulosics, such as ethyl cellulose (EC), methylethyl cellulose (MEC), carboxymethyl cellulose (CMC), CMEC, hydroxyethyl cellulose (HEC), hydroxypropyl cellulose (HPC), cellulose acetate (CA), cellulose propionate (CP), cellulose butyrate (CB), cellulose acetate butyrate (CAB), CAP, CAT, hydroxypropyl methyl cellulose (HPMC), HPMCP, HPMCAS, hydroxypropyl methyl cellulose acetate trimellitate (HPMCAT), and ethylhydroxy ethylcellulose (EHEC); polyvinyl pyrrolidone; polyvinyl alcohol; polyvinyl acetate; glycerol fatty acid esters; polyacrylamide; polyacrylic acid; copolymers of ethacrylic acid or methacrylic acid (EUDRAGIT®, Rohm America, Inc., Piscataway, N.J.); poly(2-hydroxyethyl-methacrylate); polylactides; copolymers of L-glutamic acid and ethyl-L-glutamate; degradable lactic acid-glycolic acid copolymers; poly-D-(−)-3-hydroxybutyric acid; and other acrylic acid derivatives, such as homopolymers and copolymers of butylmethacrylate, methylmethacrylate, ethylmethacrylate, ethylacrylate, (2-dimethylaminoethyl)methacrylate, and (trimethylaminoethyl)methacrylate chloride.

In another embodiment, the pharmaceutical compositions are formulated with a non-erodible matrix device. The active ingredient(s) is dissolved or dispersed in an inert matrix and is released primarily by diffusion through the inert matrix once administered. Materials suitable for use as a non-erodible matrix device include, but are not limited to, insoluble plastics, such as polyethylene, polypropylene, polyisoprene, polyisobutylene, polybutadiene, polymethylmethacrylate, polybutylmethacrylate, chlorinated polyethylene, polyvinylchloride, methyl acrylate-methyl methacrylate copolymers, ethylene-vinylacetate copolymers, ethylene/propylene copolymers, ethylene/ethyl acrylate copolymers, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, polyvinyl chloride, plasticized nylon, plasticized polyethyleneterephthalate, natural rubber, silicone rubbers, polydimethylsiloxanes, silicone carbonate copolymers, hydrophilic polymers, such as ethyl cellulose, cellulose acetate, crospovidone, and crosslinked partially hydrolyzed polyvinyl acetate, and fatty compounds, such as carnauba wax, microcrystalline wax, and triglycerides.

In a matrix controlled release system, the desired release kinetics can be controlled, for example, via the polymer type employed, the polymer viscosity, the particle sizes of the polymer and/or the active ingredient(s), the ratio of the active ingredient(s) versus the polymer, and other excipients in the compositions.

The pharmaceutical compositions provided herein in a modified release dosage form may be prepared by methods known to those skilled in the art, including direct compression, dry or wet granulation followed by compression, melt-granulation followed by compression.

2. Osmotic Controlled Release Devices

The pharmaceutical compositions provided herein in a modified release dosage form may be fabricated using an osmotic controlled release device, including one-chamber system, two-chamber system, asymmetric membrane technology (AMT), and extruding core system (ECS). In general, such devices have at least two components: (a) the core which contains the active ingredient(s); and (b) a semipermeable membrane with at least one delivery port, which encapsulates the core. The semipermeable membrane controls the influx of water to the core from an aqueous environment of use so as to cause drug release by extrusion through the delivery port(s).

In addition to the active ingredient(s), the core of the osmotic device optionally includes an osmotic agent, which creates a driving force for transport of water from the environment of use into the core of the device. One class of osmotic agents water-swellable hydrophilic polymers, which are also referred to as "osmopolymers" and "hydrogels," include, but not limited to, hydrophilic vinyl and acrylic polymers, polysaccharides such as calcium alginate, polyethylene oxide (PEO), polyethylene glycol (PEG), polypropylene glycol (PPG), poly(2-hydroxyethyl methacrylate), poly(acrylic) acid, poly(methacrylic) acid, polyvinylpyrrolidone (PVP), crosslinked PVP, polyvinyl alcohol (PVA), PVA/PVP copolymers, PVA/PVP copolymers with hydrophobic monomers such as methyl methacrylate and vinyl acetate, hydrophilic polyurethanes containing large PEO blocks, sodium croscarmellose, carrageenan, hydroxyethyl cellulose (HEC), hydroxypropyl cellulose (HPC), hydroxypropyl methyl cellulose (HPMC), carboxymethyl cellulose (CMC) and carboxyethyl, cellulose (CEC), sodium alginate, polycarbophil, gelatin, xanthan gum, and sodium starch glycolate.

The other class of osmotic agents is osmogens, which are capable of imbibing water to affect an osmotic pressure gradient across the barrier of the surrounding coating. Suitable osmogens include, but are not limited to, inorganic salts, such as magnesium sulfate, magnesium chloride, calcium chloride, sodium chloride, lithium chloride, potassium sulfate, potassium phosphate, sodium carbonate, sodium sulfite, lithium sulfate, potassium chloride, and sodium sulfate; sugars, such as dextrose, fructose, glucose, inositol, lactose, maltose, mannitol, raffinose, sorbitol, sucrose, trehalose, and xylitol; organic acids, such as ascorbic acid, benzoic acid, fumaric acid, citric acid, maleic acid, sebacic acid, sorbic acid, adipic acid, edetic acid, glutamic acid, p-tolunesulfonic acid, succinic acid, and tartaric acid; urea; and mixtures thereof.

Osmotic agents of different dissolution rates may be employed to influence how rapidly the active ingredient(s) is initially delivered from the dosage form. For example, amorphous sugars, such as Mannogeme EZ (SPI Pharma, Lewes, Del.) can be used to provide faster delivery during the first couple of hours to promptly produce the desired therapeutic effect, and gradually and continually release of the remaining amount to maintain the desired level of therapeutic or prophylactic effect over an extended period of time. In this case, the active ingredient(s) is released at such a rate to replace the amount of the active ingredient metabolized and excreted.

The core may also include a wide variety of other excipients and carriers as described herein to enhance the performance of the dosage form or to promote stability or processing.

Materials useful in forming the semipermeable membrane include various grades of acrylics, vinyls, ethers, polyamides, polyesters, and cellulosic derivatives that are water-permeable and water-insoluble at physiologically relevant pHs, or are susceptible to being rendered water-insoluble by chemical alteration, such as crosslinking. Examples of suitable polymers useful in forming the coating, include plasticized, unplasticized, and reinforced cellulose acetate (CA), cellulose diacetate, cellulose triacetate. CA propionate, cellulose nitrate, cellulose acetate butyrate (CAB). CA ethyl carbamate, CAP, CA methyl carbamate, CA succinate, cellulose acetate trimellitate (CAT) CA dimethylaminoacetate, CA ethyl carbonate, CA chloroacetate, CA ethyl oxalate, CA methyl sulfonate, CA butyl sulfonate, CA p-toluene sulfonate, agar acetate, amylose triacetate, beta glucan acetate, beta glucan triacetate, acetaldehyde dimethyl acetate, triacetate of locust bean gum, hydroxlated ethylene-vinylacetate, EC, PEG, PPG, PEG PPG copolymers, PVP, HEC, HPC, CMC, CMEC, HPMC, HPMCP, HPMCAS, HPMCAT, poly(acrylic) acids and esters and poly-(methacrylic) acids and esters and copolymers thereof, starch, dextran, dextrin, chitosan, collagen, gelatin, polyalkenes, polyethers, polysulfones, polyethersulfones, polystyrenes, polyvinyl halides, polyvinyl esters and ethers, natural waxes, and synthetic waxes.

Semipermeable membrane may also be a hydrophobic microporous membrane, wherein the pores are substantially filled with a gas and are not wetted by the aqueous medium but are permeable to water vapor, as disclosed in U.S. Pat. No. 5,798,119. Such hydrophobic but water-vapor permeable membrane are typically composed of hydrophobic polymers such as polyalkenes, polyethylene, polypropylene, polytetrafluoroethylene, polyacrylic acid derivatives, polyethers, polysulfones, polyethersulfones, polystyrenes, polyvinyl halides, polyvinylidene fluoride, polyvinyl esters and ethers, natural waxes, and synthetic waxes.

The delivery port(s) on the semipermeable membrane may be formed post-coating by mechanical or laser drilling. Delivery port(s) may also be formed in situ by erosion of a plug of water-soluble material or by rupture of a thinner portion of the membrane over an indentation in the core. In addition, delivery ports may be formed during coating process, as in the case of asymmetric membrane coatings of the type disclosed in U.S. Pat. Nos. 5,612,059 and 5,698,220.

The total amount of the active ingredient(s) released and the release rate can substantially by modulated via the thickness and porosity of the semipermeable membrane, the composition of the core, and the number, size, and position of the delivery ports.

The pharmaceutical compositions in an osmotic controlled-release dosage form may further comprise additional conventional excipients as described herein to promote performance or processing of the formulation.

The osmotic controlled-release dosage forms can be prepared according to conventional methods and techniques known to those skilled in the art (see, *Remington: The Science and Practice of Pharmacy*, supra; Santus and Baker, *J. Controlled Release* 1995, 35, 1-21; Verma et al., *Drug Development and Industrial Pharmacy* 2000, 26, 695-708; Verma et al., *J. Controlled Release* 2002, 79, 7-27).

In certain embodiments, the pharmaceutical compositions provided herein are formulated as AMT controlled-release dosage form, which comprises an asymmetric osmotic membrane that coats a core comprising the active ingredient(s) and other pharmaceutically acceptable excipients. See, U.S. Pat. No. 5,612,059 and WO 2002/17918. The AMT controlled-release dosage forms can be prepared according to conventional methods and techniques known to those skilled in the art, including direct compression, dry granulation, wet granulation, and a dip-coating method.

In certain embodiment, the pharmaceutical compositions provided herein are formulated as ESC controlled-release dosage form, which comprises an osmotic membrane that coats a core comprising the active ingredient(s), hydroxylethyl cellulose, and other pharmaceutically acceptable excipients.

3. Multiparticulate Controlled Release Devices

The pharmaceutical compositions provided herein in a modified release dosage form may be fabricated as a multiparticulate controlled release device, which comprises a multiplicity of particles, granules, or pellets, ranging from about 10 µm to about 3 mm, about 50 µm to about 2.5 mm, or from about 100 µm to 1 mm in diameter. Such multiparticulates may be made by the processes know to those skilled in the art, including wet- and dry-granulation, extrusion/spheronization, roller-compaction, melt-congealing, and by spray-coating seed cores. See, for example, *Multiparticulate Oral Drug Delivery*; Marcel Dekker: 1994; and *Pharmaceutical Pelletization Technology*; Marcel Dekker: 1989.

Other excipients as described herein may be blended with the pharmaceutical compositions to aid in processing and forming the multiparticulates. The resulting particles may themselves constitute the multiparticulate device or may be coated by various film-forming materials, such as enteric polymers, water-swellable, and water-soluble polymers. The multiparticulates can be further processed as a capsule or a tablet.

4. Targeted Delivery

The pharmaceutical compositions provided herein may also be formulated to be targeted to a particular tissue, receptor, or other area of the body of the subject to be treated, including liposome-, resealed erythrocyte-, and antibody-based delivery systems. Examples include, but are not limited to, U.S. Pat. Nos. 6,316,652; 6,274,552; 6,271,359; 6,253,872; 6,139,865; 6,131,570; 6,120,751; 6,071,495; 6,060,082; 6,048,736; 6,039,975; 6,004,534; 5,985,307; 5,972,366; 5,900,252; 5,840,674; 5,759,542; and 5,709,874.

5.3.1 Articles of Manufacture

The compounds or pharmaceutically acceptable derivatives can be packaged as articles of manufacture containing packaging material, a compound or pharmaceutically acceptable derivative thereof provided herein, which is used for treatment, prevention or amelioration of one or more symptoms associated with CCR9 activity, and a label that indicates that the compound or pharmaceutically acceptable derivative thereof is used for treatment, prevention or amelioration of one or more symptoms of CCR9 receptor mediated diseases.

The articles of manufacture provided herein contain packaging materials. Packaging materials for use in packaging pharmaceutical products are well known to those of skill in the art. See, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. A wide array of formulations of the compounds and compositions provided herein are contemplated.

5.4 Evaluation of the Activity of the Compounds

The CCR9 antagonist activity of the compounds provided herein can be demonstrated by methods known to one of skill in the art. Exemplary methods are described in US Publication Nos. US2004/0180892 and US2005/0049286, which are incorporated herein by reference. An exemplary assay for determining CCR9 antagonist activity of the compounds provided herein is CCR9 FLIPR/FlexStation Assay. In certain embodiments, the following protocol is used for the assay:

CCR9 FLIPR/FlexStation Assay Protocol

Calcium assay in FLIPR/FlexStation determines inhibitors of TECK induced calcium mobilization in CCR9-Flp-CHO cells that stably over express human CCR9 receptor. CCR9-Flp-CHO cells are seeded at 25,000 cells/well in a clear bottom, black wall 96-well plate (Greiner #655090) one day prior to assay. Cells are grown in a tissue culture incubator at 37° C. with 5% $CO_2$ for 18 to 24 hours.

Wash buffer and dye loading buffer are prepared fresh each time the assay is performed. Wash buffer is prepared according to the following protocol: 20 ml 10×HBSS (Invitrogen Gibco #14065-056), 4 ml 1M HEPES (Sigma H3784), 174 ml sterile deionized water; then add 140 mg probenecid (Sigma P8761) dissolved in 2 ml 1M NaOH (Fisher S318) to solution and pH to 7.4. This wash buffer contains 1×HBSS, 20 mM HEPES and 2.5 mM probenecid. For one 96-well plate, dye loading buffer is prepared as following: 11 ml wash buffer, 44 µl Fluo-4/pluoronic acid mix (prepared from 22 µL aliquot of 2 mM Fluo-4 (Molecular Probes F14202, 1 mg/tube)+22 µl 20% pluronic F-127 (Molecular Probes P3000MP).

Cells are loaded with dye according to the protocol below:
1. Prepare wash buffer with 1×HBSS/HEPES at room temperature
2. Prepare loading buffer (keep in dark)
3. Aspirate culture media and wash with 100 µl wash buffer per well×1
4. Add 100 µl dye loading buffer to each well
5. Incubate at 37° C. for 30 minutes
6. Aspirate loading buffer
7. Wash with 100 µl wash buffer per well×3
8. Add 100 µl wash buffer per well
9. Incubate at 37° C. for 30 minutes
10. Assay plate with FLIPR or FlexStation 10 mM stock compounds in DMSO are prepared and diluted in DMSO to 1 mM. Compounds are diluted in wash buffer to make 8 point series dilutions containing same final concentration of DMSO (1%). Compounds are tested in duplicate wells for each point. Ligand rhTECK (R&D Systems 334-TK) was diluted to 6× of its EC70 with wash buffer. Appropriate amount of 6× ligand is added to each well. Data is analyzed using XLfit3 software to calculate $IC_{50}$ value of antagonist activity for each compound. $IC_{50}$ values for antagonist activity of exemplary compounds are provided in Table 1, Example 64.

5.5 Methods of Treatment and Prevention

In certain embodiments, provided herein are methods for modulating an activity of CCR9 receptor by contacting the receptor with a compound or composition provided herein. In one embodiment, provided herein are methods for antagonizing an action of CCR9 receptor by contacting the receptor with a compound or composition provided herein.

In other embodiments, provided herein are methods for treatment, prevention, or amelioration of one or more diseases or conditions associated with CCR9 receptor activity, including, but not limited to inflammatory bowel disease, including Crohn's disease and ulcerative colitis, celiac disease and other forms of intestinal inflammation, including celiac sprue and gluten-sensitive enteropathy, primary sclerosing cholangitis; HIV; as well as various cancers, including, prostate cancer, leukemia, and small intestinal melanoma.

5.5.1 Combination Therapy with a Second Active Agent

The compounds provided herein may be administered as the sole active ingredient or in combination with other active ingredients. Other active ingredients that may be used in combination with the compounds provided herein include but are not limited to, compounds known to treat diseases associated with CCR9 receptor modulation or compounds known to modulate CCR9 receptor activity. Examples of such compounds include, but are not limited to antihistamines, corticosteroids, β2-agonists, steroid receptor modulators, anticholinergic compounds, immunomodulators, bronchdilators, leukotriene modifiers, COX-2 inhibitors and anti-inflammatory compounds.

Administration of the active ingredient combination may take place either by separate administration of the active ingredients to the patient or in the form of combination products in which a plurality of active ingredients are present in one pharmaceutical preparation.

It will be appreciated that every suitable combination of the compounds provided herein with one or more of the aforementioned compounds and optionally one or more further pharmacologically active substances is contemplated herein.

It is understood that the foregoing detailed description and accompanying examples are merely illustrative, and are not to be taken as limitations upon the scope of the subject matter. Various changes and modifications to the disclosed embodiments will be apparent to those skilled in the art. Such changes and modifications, including without limitation those relating to the chemical structures, substituents, derivatives, intermediates, syntheses, formulations and/or methods of use provided herein, may be made without departing from the spirit and scope thereof. U.S. patents and publications referenced herein are incorporated by reference.

EXAMPLES

Certain embodiments of the claimed subject matter are illustrated by the following non-limiting examples.

Example 1

Preparation of 3-(2-bromo-4-tert-butylphenylsulfonamido)thiophene-2-carboxylic acid, sodium salt (5)

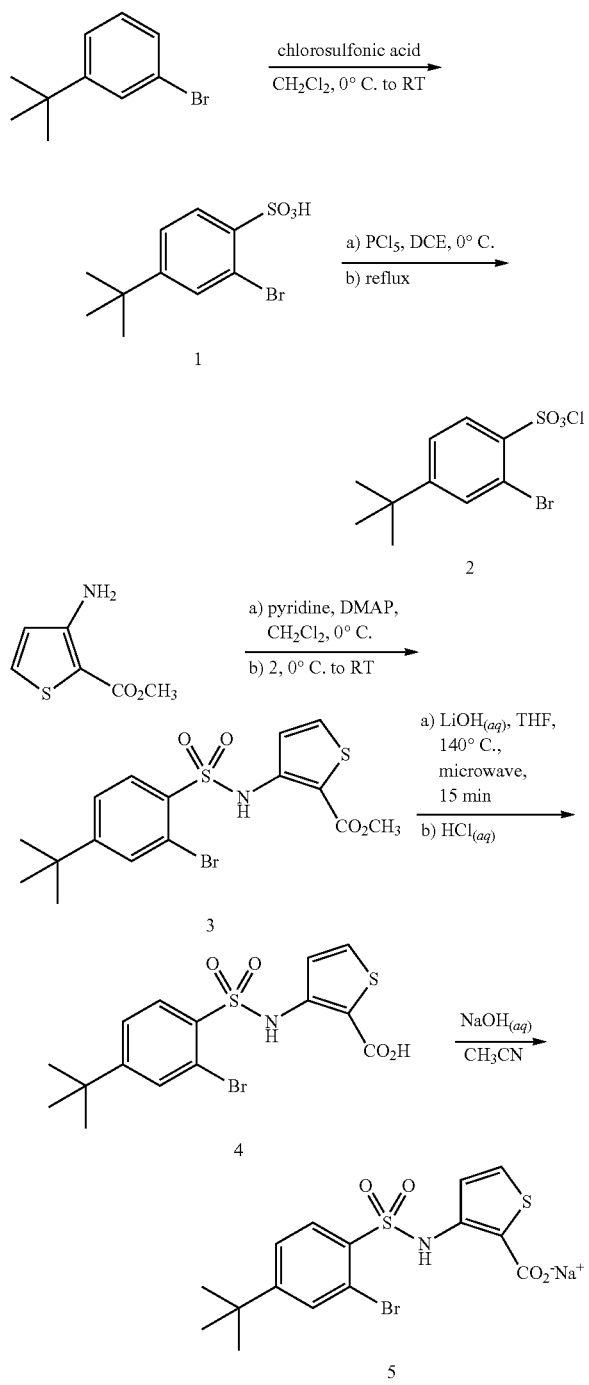

I. 2-Bromo-4-tert-butylbenzenesulfonic acid (1)

To a cooled (0° C.) solution of commercially available 1-bromo-3-tert-butylbenzene (42.6 g; 199 mmol) in anhydrous dichloromethane (800 mL) was added chlorosulfonic acid (15.9 mL; 239.0 mmol) dropwise. After addition was complete, the reaction was stirred at 0° C. for an additional 30 minutes, allowed to gradually warm to room temperature and further stirred overnight. The reaction mixture was concentrated under reduced pressure to about 500 mL and washed with aqueous hydrochloric acid (20 mL; 20N). The organic layer was separated and dried over magnesium sulfate which resulted in formation of a white precipitate. Methanol (200 mL) was added to dissolve the precipitate. The organic solution was filtered and concentrated under reduced pressure to yield the title product as a white solid (53.0 g).

II. 2-Bromo-4-tert-butylbenzene-1-sulfonyl chloride (2)

To cooled (0° C.) solution of 1 (10.11 g; 34.48 mmol) in dichloroethane (200 mL) was added phosphorus pentachloride (10.77 g; 51.70 mmol) slowly and portion-wise. The reaction was heated at reflux overnight, cooled to room temperature, and then concentrated under reduced pressure. The resulting crude brown oil residue was purified by automated silica gel column chromatography (Biotage®) eluting with ethyl acetate/hexanes (0 to 15% v/v over 400 mL gradient elution) to give the title product as an off-white solid (7.60 g)

III. Methyl 3-(2-bromo-4-tert-butylphenylsulfonamido)thiophene-2-carboxylate (3)

To a cooled (0° C.) solution of methyl 3-aminothiophene-2-carboxylate (1.84 g; 10.60 mmol), 4-dimethylaminopyridine (323.0 mg; 2.65 mmol) and pyridine (2.57 mL; 31.0 mmol) in anhydrous dichloromethane (60 mL) was added 2 (3.33 g; 10.6 mmol) portion-wise. After addition was complete the reaction mixture was stirred at 0° C. for 20 minutes, gradually allowed to warm to room temperature, and further stirred for 16 hours. The reaction mixture was allowed to cool to room temperature and washed with aqueous hydrochloric acid (50 mL; 2N). The combined organic phases were dried over magnesium sulfate, filtered, and concentrated under reduced pressure to yield a yellow solid. Trituration from diisopropyl ether yielded the title product as a yellow solid (3.97 g).

Note: Alternatively, the crude residue may be purified by automated silica gel chromatography (Biotage®) using ethyl acetate/hexanes as the eluant system (0 to 25% v/v over 400 mL gradient elution).

IV. 3-(2-Bromo-4-tert-butylphenylsulfonamido)thiophene-2-carboxylic acid (4)

To a solution of 3 (200.0 mg; 0.46 mmol) in tetrahydrofuran (5 mL) in a 2.5-5.0 mL microwave reactor tube was added aqueous lithium hydroxide (5 mL; excess; 2M). The reaction vessel was subjected to the following microwave conditions: Temperature=140° C.; Time=15 minutes; Power=250 W; Cooling on; Absorption=Very High. The crude reaction mixture was allowed to cool to room temperature and then acidified by the addition of aqueous hydrochloric acid (15 mL; 2N) and extracted with ethyl acetate (3×10 mL). The combined organic phases were dried over magnesium sulfate, filtered and concentrated under reduced pressure to afford a beige solid. The latter was triturated from diisopropyl ether to yield the title compound as a beige solid (96.0 mg).

V. 3-(2-Bromo-4-tert-butylphenylsulfonamido)thiophene-2-carboxylic acid, sodium salt (5)

To a solution of 4 (93.4 mg; 0.22 mmol) in acetonitrile (2 mL) was added aqueous sodium hydroxide (2.23 mL; 0.22 mmol; 0.1M). The reaction mixture was frozen in a dry ice/acetone bath and lyophilized to yield the title compound as a white solid (54.0 mg).

Example 2

Preparation of 3-(5-tert-butyl-4'-chlorobiphenyl-2-ylsulfonamido)thiophene-2-carboxylic acid, disodium salt (10)

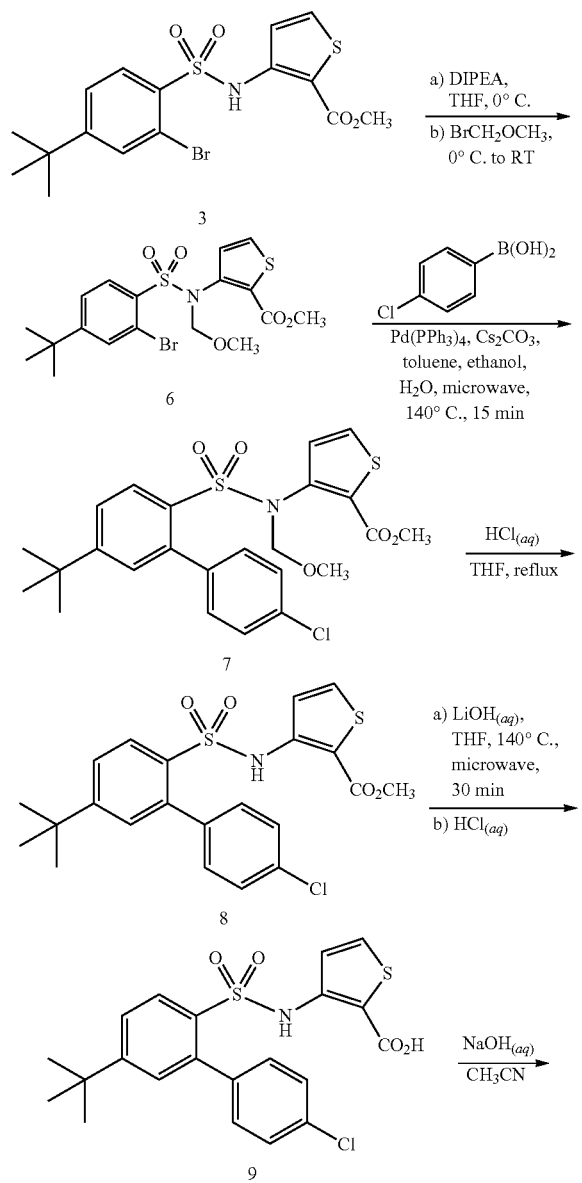

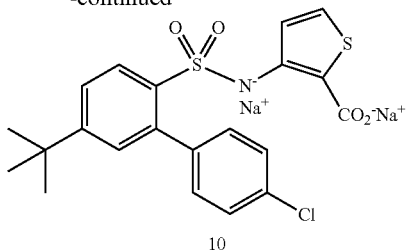

I. Methyl 3-[2-bromo-4-tert-butyl-N-(methoxymethyl)phenylsulfonamido]thiophene-2-carboxylate (6)

To a cooled (0° C.) solution of 3 (8.23 g; 19.0 mol) in N,N-diisopropylethylamine (5.29 mL; 30.4 mmol) and anhydrous tetrahydrofuran (200 mL) was added 1-bromo-2-methoxyethane (2.33 mL; 28.5 mmol) dropwise. After the addition was complete the reaction mixture was stirred at 0° C. for 10 minutes, allowed to gradually warm to room temperature and then stirred for 3 hours. The reaction mixture was diluted with dichloromethane (200 mL) and washed with water (100 mL). The organic layer was separated, dried over magnesium sulfate, filtered, and concentrated under reduced pressure. The resulting orange oil residue was further purified by automated silica gel chromatography (Biotage®) eluting with ethyl acetate/hexanes (0 to 25% v/v over 400 mL gradient elution) to afford a clear oil. Trituration from hexanes afforded the title product as a white solid (6.51 g).

II. Methyl 3-[5-tert-butyl-4'-chloro-N-(methoxymethyl)biphenyl-2-ylsulfonamido]thiophene-2-carboxylate (7)

A 2.5-5.0 mL microwave reaction tube was successively charged with 6 (250 mg; 0.54 mmol), 4-chlorophenylboronic acid (126 mg; 0.81 mmol), cesium carbonate (527 mg; 1.62 mmol), tetrakis(triphenylphosphine)palladium(0) 31.2 mg; 0.03 mmol), toluene (1.3 mL), ethanol (1.3 mL) and water (1.3 mL). The reaction tube was purged with nitrogen and subjected to the following microwave conditions: Temperature=140° C.; Power=250 W; Time=15 minutes; Cooling On; Absorption Very High. The reaction mixture was allowed to cool to room temperature and then diluted with ethyl acetate (15 mL) and washed with aqueous hydrochloric acid (3×10 mL; 2N). The organic layer was dried over magnesium sulfate, filtered, and concentrated under reduced pressure. The resulting dark oil residue was purified by automated silica gel chromatography (Biotage®) eluting with ethyl acetate/hexanes (0 to 30% v/v over 400 mL gradient elution) to yield the title product as a clear oil (200 mg).

III. Methyl 3-(5-tert-butyl-4'-chlorobiphenyl-2-ylsulfonamido)thiophene-2-carboxylate (8)

To a solution of 7 (120.0 mg; 0.24 mmol) in tetrahydrofuran (5 mL) was added aqueous hydrochloric acid (1.2 mL; 2.4 mmol; 2N). The reaction mixture was heated at 75° C. for 4 hours, and then additional aqueous hydrochloric acid (3.0 mL; 6N) was added and the reaction mixture further heated at reflux for 4-5 hours. The reaction mixture was allowed to cool to room temperature and then extracted with ethyl acetate (15 mL). The organic layer was separated, dried over magnesium sulfate, filtered and concentrated under reduced pressure to yield a white solid residue which was purified by automated silica gel chromatography (Biotage®) eluting with ethyl acetate/hexanes (0 to 20% v/v over 400 mL gradient elution) to yield the title product as a white solid (80.0 mg).

IV. 3-(5-tert-butyl-4'-chlorobiphenyl-2-ylsulfonamido)thiophene-2-carboxylic acid (9)

To a solution of 8 (200.0 mg; 0.46 mmol) in tetrahydrofuran (5 mL) in a 2.5-5.0 mL microwave reactor tube was added aqueous lithium hydroxide (5.0 mL; excess; 2M). The reaction vessel was subjected to the following microwave conditions: Temperature=140° C.; Time=30 minutes; Power=250 W; Cooling on; Absorption=Very High. The crude reaction mixture was allowed to cool to room temperature, acidified by the addition of aqueous hydrochloric acid (15 mL; 2N), and extracted with ethyl acetate (3×10 mL). The organic layers were combined and concentrated under reduced pressure to afford a beige solid. The latter was triturated from diisopropyl ether to yield the title compound as a white solid (37.0 mg).

V. 3-(5-tert-Butyl-4'-chlorobiphenyl-2-ylsulfonamido)thiophene-2-carboxylic acid, disodium salt (10)

To a solution of 9 (37.0 mg; 0.08 mmol) in acetonitrile (2 mL) was added aqueous sodium hydroxide (1.64 mL; 0.16 mmol; 0.1M). The reaction mixture was frozen in a dry ice/acetone bath and lyophilized to yield the title compound as a white solid (23.2 mg).

Example 3

Preparation of 3-[4-tert-butyl-2-(morpholin-4-yl)phenylsulfonamido]thiophene-2-carboxylic acid (12)

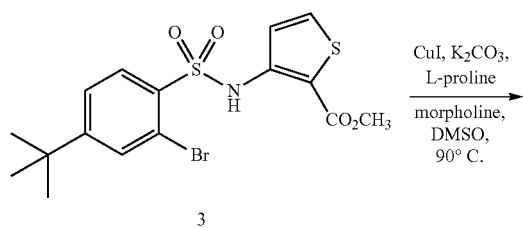

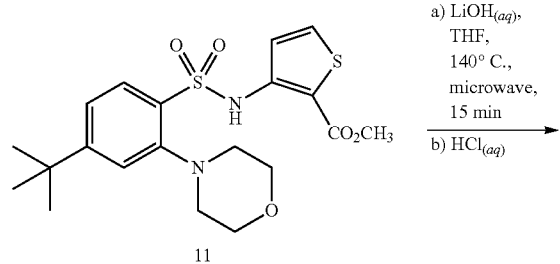

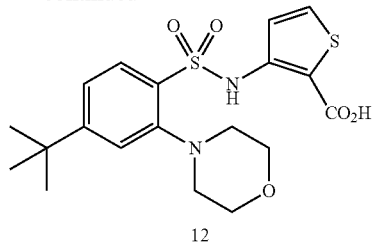

I. Methyl 3-(4-tert-butyl-2-morpholinophenylsulfonamido)thiophene-2-carboxylate (11)

To an evacuated and nitrogen purged mixture of 3 (50.0 mg; 0.11 mmol), copper iodide (2.0 mg; 0.011 mmol), potassium carbonate (29.0 mg; 0.30 mmol) and L-Proline (2.4 mg; 0.20 mmol), dimethyl sulfoxide (0.4 mL) and morpholine (13.7 mg; 0.157 mmol) were added. The reaction mixture was heated at 90° C. under nitrogen for 24 hours and then cooled to room temperature, diluted with water and extracted with ethyl acetate (2×). The combined organic extracts were washed with aqueous saturated sodium chloride, dried over magnesium sulfate, and concentrated under reduced pressure. The resulting crude dark oil was purified by automated silica gel chromatography (Biotage®) eluting with ethyl acetate/hexanes (10 to 20% gradient elution) to give a white solid which was further purified by preparative HPLC to afford the title compound as an off-white solid (21.8 mg).

II. 3-[4-tert-Butyl-2-(morpholin-4-yl)phenylsulfonamido]thiophene-2-carboxylic acid (12)

To a solution of 11 (24.7 mL; 0.06 mmol) in tetrahydrofuran (5 mL) in a 2.5-5.0 mL microwave reactor tube was added aqueous lithium hydroxide (1 mL; 2M). The reaction vessel was subjected to the following microwave conditions: Temperature=140° C.; Time=15 minutes; Power=250 W; Cooling on; Absorption=Very High. The crude reaction mixture was allowed to cool to room temperature, acidified by the addition of aqueous hydrochloric acid (15 mL; 2N), and extracted with ethyl acetate (3×10 mL). The organic phases were combined and dried over magnesium sulfate, filtered, and concentrated under reduced pressure to afford a beige solid. The latter was triturated from diisopropyl ether to yield the title compound as a beige solid (24.1 mg).

Example 4

Preparation of 3-[5-tert-butyl-4'-(dimethylamino)biphenyl-2-ylsulfonamido]thiophene-2-carboxylic acid, disodium salt (16)

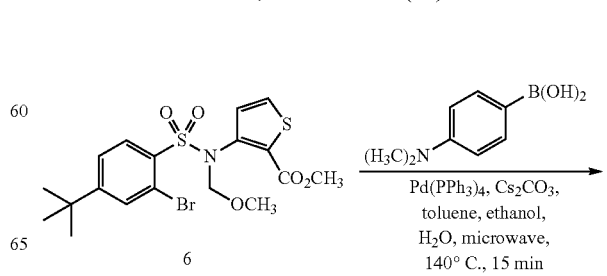

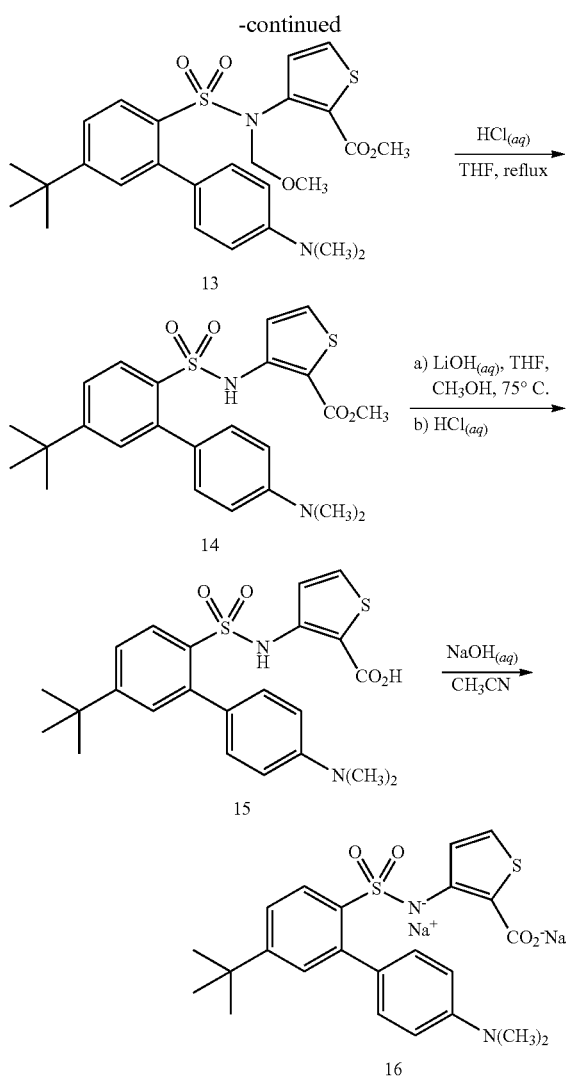

I. Methyl 3-[5-tert-butyl-4'-(dimethylamino)-N-(methoxymethyl)biphenyl-2-ylsulfonamido]thiophene-2-carboxylate (13)

A 2.5-5.0 mL microwave reaction tube was successively charged with 6 (200.0 mg; 0.43 mmol), 4-(dimethylamino) phenylboronic acid (107.0 mg; 0.65 mmol), cesium carbonate (420.0 mg; 1.29 mmol), tetrakis(triphenylphosphine)palladium(0) (25.0 mg; 0.022 mmol), toluene (1.3 mL), ethanol (1.3 mL) and water (1.3 mL). The reaction tube was purged with nitrogen and subjected to the following microwave conditions: Temperature=140° C.; Power=250 W; Time=15 minutes; Cooling On; Absorption Very High. The reaction mixture was allowed to cool to room temperature and then was diluted with ethyl acetate (15 mL) and washed with aqueous hydrochloric acid (3×10 mL; 2N). The organic layers were combined and dried over magnesium sulfate, filtered, and concentrated under reduced pressure. The crude dark oil residue was purified by automated silica gel column chromatography (Biotage®) eluting with ethyl acetate/hexanes (0 to 25% v/v over 400 mL gradient elution) to give the title product as an off-white foam (157 mg).

II. Methyl 3-[5-tert-butyl-4'-(dimethylamino)biphenyl-2-ylsulfonamido]thiophene-2-carboxylate (14)

To a solution of 13 (150.0 mg; 0.30 mmol) in tetrahydrofuran (6 mL) was added aqueous hydrochloric acid (1.0 mL; 2.0 mmol; 2N). The reaction mixture was heated at 75° C. for 4 hours, and then additional aqueous hydrochloric acid (3.0 mL; 6N) was added and the reaction mixture further heated at reflux for 4-5 hours. The reaction mixture was allowed to cool to room temperature and then extracted with ethyl acetate (15 mL). The organic phase was dried over magnesium sulfate and filtered. The filtrate was concentrated under reduced pressure and the resulting white solid residue was purified by automated silica gel column chromatography (Biotage®) eluting with ethyl acetate/hexanes (0 to 30% v/v over 400 mL gradient elution) to give the title product as a clear oil (50.9 mg).

III. 3-[5-tert-Butyl-4'-(dimethylamino)biphenyl-2-ylsulfonamido]thiophene-2-carboxylic acid (15)

To a solution of 14 (50.0 mg; 0.11 mmol) in tetrahydrofuran (1 mL) and methanol (1 mL) was added aqueous lithium hydroxide (2 mL; 2M). The reaction mixture was heated at 75-80° C. for 6 hours, allowed to cool to room temperature and then concentrated under reduced pressure. The resulting residue was dissolved in chloroform (15 mL) and washed with aqueous hydrochloric acid (2×10 mL; 2N). The combined organic phases were dried over magnesium sulfate, filtered, and concentrated under reduced pressure to yield the title compound as a brown solid (47.2 mg).

IV. 3-[5-tert-Butyl-4'-(dimethylamino)biphenyl-2-ylsulfonamido]thiophene-2-carboxylic acid, disodium salt (16)

To a solution of 15 (43.4 mg; 0.10 mmol) in acetonitrile (2 mL) was added aqueous sodium hydroxide (1.9 mL; 0.38 mmol; 0.1M). The reaction mixture was frozen in a dry ice/acetone bath and lyophilized to yield the title compound as a light brown solid (40.8 mg).

Example 5

Preparation of 3-[4-tert-butyl-2-(pyrimidin-5-yl) phenylsulfonamido]thiophene-2-carboxylic acid, disodium salt (20)

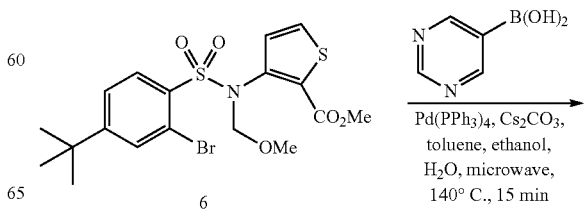

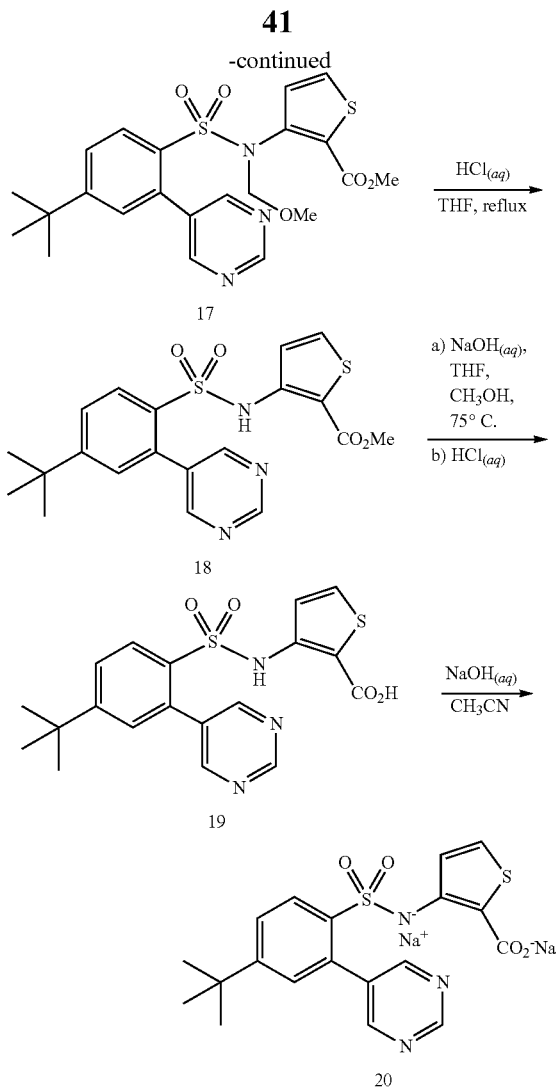

I. Methyl 3-[4-tert-butyl-N-(methoxymethyl)-2-(pyrimidin-5-yl)phenylsulfonamido]thiophene-2-carboxylate (17)

A 2.5-5.0 mL microwave reaction tube was successively charged with 6 (200.0 mg; 0.43 mmol), pyrimidine-5-boronic acid 80.0 mg; 0.645 mmol) cesium carbonate (420.0 mg; 1.297 mmol), tetrakis(triphenylphosphine)palladium(0) (25.0 mg; 0.022 mmol), toluene (1.3 mL), ethanol (1.3 mL) and water (1.3 mL). The reaction tube was purged with nitrogen and subjected to the following microwave conditions: Temperature=140° C.; Power=250 W; Time=15 minutes; Cooling On; Absorption Very High. The reaction mixture was allowed to cool to room temperature and then was diluted with ethyl acetate (15 mL) and washed with aqueous hydrochloric acid (3×10 mL; 2N). The organic layer was dried over magnesium sulfate, filtered, and concentrated under reduced pressure. The crude orange oil residue was purified by automated silica gel column chromatography (Biotage®) eluting with ethyl acetate/hexanes (0 to 30% v/v over 400 mL gradient elution) to give the title product as a clear oil (80.0 mg).

II. Methyl 3-[4-tert-butyl-2-(pyrimidin-5-yl)phenylsulfonamido]thiophene-2-carboxylate (18)

To a solution of 17 (80.0 mg; 0.17 mmol) in tetrahydrofuran (5 mL) was added aqueous hydrochloric acid (5.0 mL; 10.0 mmol; 2N). The reaction mixture was heated at 75° C. for 4 hours, and then additional aqueous hydrochloric acid (3.0 mL; 6N) was added and the reaction mixture further heated at reflux for 4-5 hours. The reaction mixture was allowed to cool to room temperature and then extracted with ethyl acetate (15 mL). The organic layer was separated, dried over magnesium sulfate, filtered, and concentrated under reduced pressure. The resulting crude clear oil was purified by automated silica gel column chromatography (Biotage®) eluting with ethyl acetate/hexanes (0 to 30% v/v over 400 mL gradient elution) to give the title product as a clear oil (64.0 mg).

III. 3-[4-tert-Butyl-2-(pyrimidin-5-yl)phenylsulfonamido]thiophene-2-carboxylic acid (19)

To a solution of 18 (62.0 mg; 0.14 mmol) in tetrahydrofuran (1 mL) and methanol (1 mL) was added aqueous sodium hydroxide (2 mL; 2M). The reaction mixture was heated at 75-80° C. for 6 hours, allowed to cool to room temperature and then concentrated under reduced pressure. The resulting residue was dissolved in chloroform (15 mL) and washed with aqueous hydrochloric acid (2×10 mL; 2N). The organic phase was dried over magnesium sulfate, filtered, and concentrated under reduced pressure to yield the title compound as a white oil (68.0 mg).

IV. 3-[4-tert-Butyl-2-(pyrimidin-5-yl)phenylsulfonamido]thiophene-2-carboxylic acid, disodium salt (20)

To a solution of 19 (50.8 mg; 0.12 mmol) in acetonitrile (2 mL) was added aqueous sodium hydroxide (2.4 mL; 0.24 mmol; 0.1M). The reaction mixture was frozen in a dry ice/acetone bath and lyophilized to yield the title compound as a white solid (48.0 mg).

Example 6

Preparation of 3-(4-tert-Butyl-2-chlorophenylsulfonamido)thiophene-2-carboxylic acid, disodium salt (24)

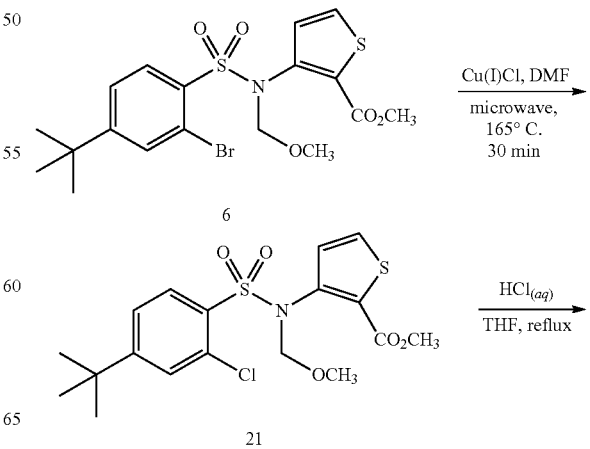

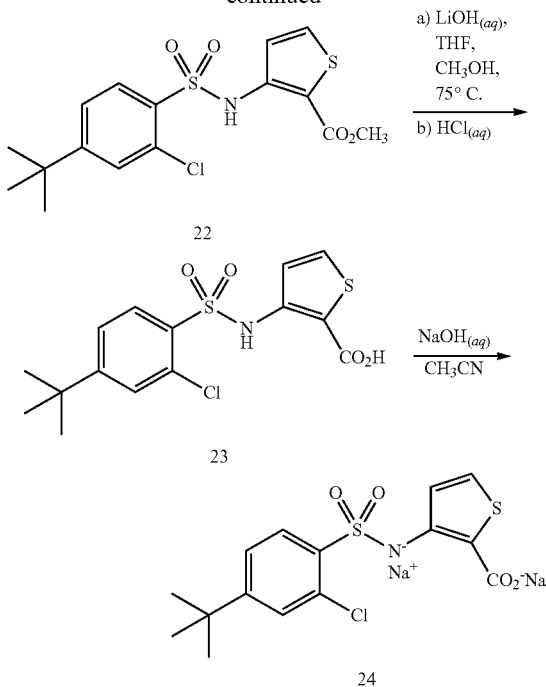

III. 3-(4-tert-Butyl-2-chlorophenylsulfonamido) thiophene-2-carboxylic acid (23)

To a solution of 22 (272.0 mg; 0.73 mmol) in tetrahydrofuran (8 mL) and methanol (2 mL) was added aqueous lithium hydroxide (4 mL; 2M). The reaction mixture was heated at 75-80° C. for 6 hours, allowed to cool to room temperature and then concentrated under reduced pressure. The resulting residue was dissolved in chloroform (15 mL) and washed with aqueous hydrochloric acid (2×10 mL; 2N). The organic phase was dried over magnesium sulfate, filtered, and concentrated under reduced pressure to yield the title compound as a white solid (237 mg).

IV. 3-(4-tert-Butyl-2-chlorophenylsulfonamido) thiophene-2-carboxylic acid, disodium salt (24)

To a solution of 23 (237.0 mg; 0.63 mmol) in acetonitrile (12 mL) was added aqueous sodium hydroxide (12.67 mL; 1.26 mmol; 0.1M). The reaction mixture was frozen in a dry ice/acetone bath and lyophilized to yield the title compound as an off-white solid (245 mg).

Example 7

Preparation of 3-(4-tert-butyl-2-styrylphenylsulfonamido)thiophene-2-carboxylic acid, disodium salt (28)

I. Methyl 3-[2-chloro-4-tert-butyl-N-(methoxymethyl)phenylsulfonamido]thiophene-2-carboxylate (21)

To a solution of 6 (350.0 mg; 0.76 mmol) in N,N-dimethylformamide (4.0 mL) in a 2.5-5.0 mL microwave reactor tube was added copper(I) chloride (89.9 mg; 0.91 mmol). The reaction mixture was subjected to the following microwave conditions: Temperature=165° C.; Power=200 W; Time=30 minutes; Absorption=High. The reaction mixture was allowed to cool to room temperature and then was diluted with ethyl acetate (15 mL) and washed with aqueous hydrochloric acid (2×10 mL; 2N). The organic layer was dried over magnesium sulfate, filtered, and concentrated under reduced pressure. The resulting yellow oil residue was purified by automated silica gel column chromatography (Biotage®) eluting with ethyl acetate/hexanes (0 to 25% v/v over 550 mL gradient elution) to give a clear oil. Overnight vacuum drying of this clear oil gave the title product as a white solid (247 mg).

II. Methyl 3-(2-chloro-4-tert-butylphenylsulfonamido)thiophene-2-carboxylate (22)

To a solution of 21 (292.0 mg; 0.68 mmol) in tetrahydrofuran (5 mL) was added aqueous hydrochloric acid (3.38 mL; 6.76 mol; 2N). The reaction mixture was heated at 75° C. for 4 hours, and then additional aqueous hydrochloric acid (3.0 mL; 6N) was added and the reaction mixture further heated at reflux for 4-5 hours. The reaction mixture was allowed to cool to room temperature and then extracted with ethyl acetate (15 mL). The organic layer was separated, dried over magnesium sulfate, filtered and concentrated under reduced pressure to yield a white solid which was purified by automated silica gel chromatography (Biotage®) eluting with ethyl acetate/hexanes (0 to 25% v/v over 400 mL gradient elution) to yield the title as an off-white solid (180 mg).

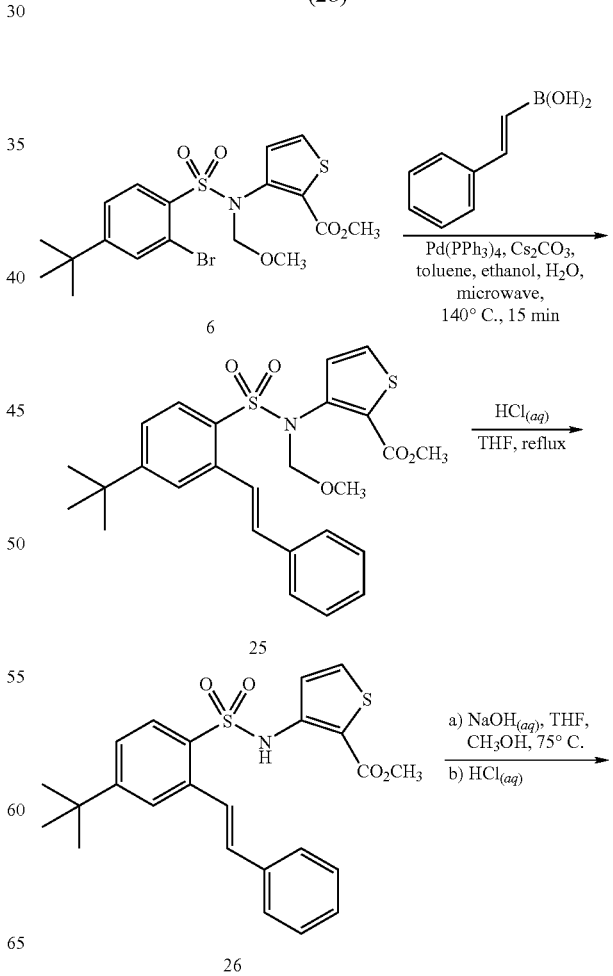

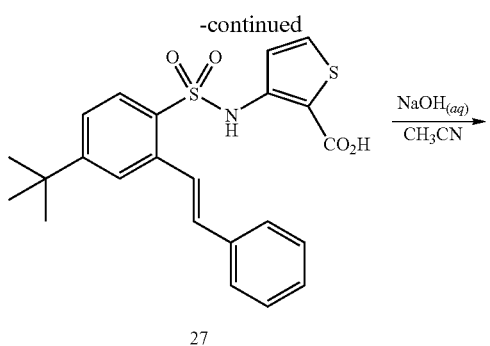

27

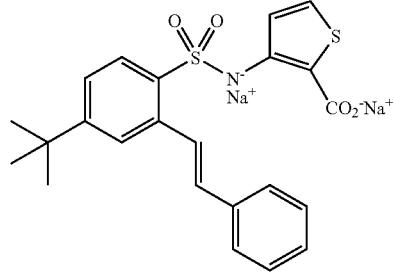

28

I. Methyl 3-[4-tert-butyl-N-(methoxymethyl)-2-styrylphenylsulfonamido]thiophene-2-carboxylate (25)

A 2.5-5.0 mL microwave reaction tube was successively charged with 6 (200.0 mg, 0.43 mmol), trans-2-phenylvinylboronic acid (96.0 mg; 0.65 mmol), cesium carbonate (420.0 mg; 1.30 mmol), tetrakis(triphenylphosphine)palladium(0) (25.0 mg; 0.022 mmol), toluene (1.3 mL), ethanol (1.3 mL) and water (1.3 mL). The reaction tube was purged with nitrogen and subjected to the following microwave conditions: Temperature=140° C.; Power=250 W; Time=15 minutes; Cooling On; Absorption Very High. The reaction mixture was allowed to cool to room temperature and then was diluted with ethyl acetate (15 mL) and washed with aqueous hydrochloric acid (3×10 mL; 2N). The organic layer was dried over magnesium sulfate, filtered, and concentrated under reduced pressure. The crude dark oil residue was purified by automated silica gel column chromatography (Biotage®) eluting with ethyl acetate/hexanes (0 to 30% v/v over 400 mL gradient elution) to give the title product as a white solid (134 mg).

II. Methyl 3-(4-tert-butyl-2-styrylphenylsulfonamido)thiophene-2-carboxylate (26)

To a solution of 25 (134.0 mg; 0.27 mmol) in tetrahydrofuran (8 mL) was added aqueous hydrochloric acid (8.0 mL; 16.0 mmol; 2N). The reaction mixture was heated at 75° C. for 4 hours, and then additional aqueous hydrochloric acid (3.0 mL; 6N) was added and the reaction mixture further heated at reflux for 4-5 hours. The reaction mixture was allowed to cool to room temperature and then extracted with ethyl acetate (15 mL). The organic layer was separated, dried over magnesium sulfate, filtered and concentrated under reduced pressure to yield an orange oil residue which was purified by automated silica gel chromatography (Biotage®) eluting with ethyl acetate/hexanes (0 to 30% v/v over 400 mL gradient elution) to yield the title product as a white solid (60.9 mg).

III. 3-(4-tert-Butyl-2-styrylphenylsulfonamido)thiophene-2-carboxylic acid (27)

To a solution of 26 (60.0 mg; 0.13 mmol) in tetrahydrofuran (1 mL) and methanol (1 mL) was added aqueous sodium hydroxide (2 mL; 2M). The reaction mixture was heated at 75-80° C. for 6 hours, allowed to cool to room temperature and then concentrated under reduced pressure. The resulting residue was dissolved in chloroform (15 mL) and washed with aqueous hydrochloric acid (2×10 mL; 2N). The organic phase was dried over magnesium sulfate, filtered, and concentrated under reduced pressure to yield the title compound as a white solid (59.2 mg).

IV. 3-(4-tert-Butyl-2-styrylphenylsulfonamido)thiophene-2-carboxylic acid, disodium salt (28)

To a solution of 27 (57.0 mg; 0.13 mmol) in acetonitrile (2 mL) was added aqueous sodium hydroxide (2.5 mL; 0.25 mmol; 0.1M). The reaction mixture was frozen in a dry ice acetone bath and lyophilized to yield the title compound as a white solid (60.6 mg).

Example 8

Preparation of 3-(tert-butyl-2-methoxyphenylsulfonamido)thiophene-2-carboxylic acid, disodium salt (34)

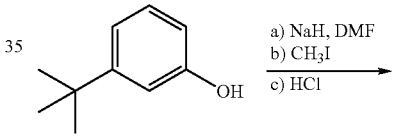

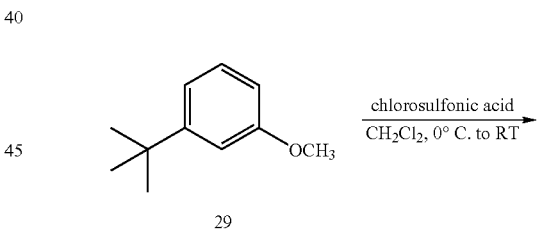

29

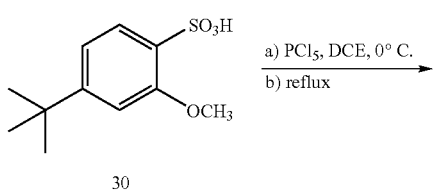

30

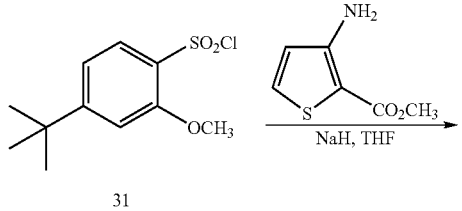

31

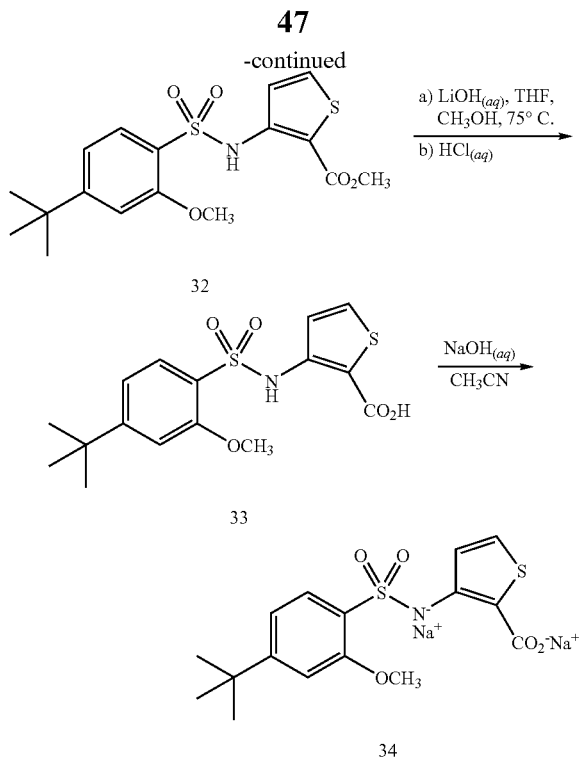

I. 1-tert-Butyl-3-methoxybenzene (29)

To a solution of 3-tert-butylphenol (5.0 g; 33.28 mmol) in N,N-dimethylformamide (166 mL) at room temperature under nitrogen was added sodium hydride (2.0 g; 49.92 mmol). The reaction mixture was stirred at room temperature for 10 minutes and then iodomethane (6.2 mL; 99.84 mmol) was added. After stirring at room temperature overnight, the reaction mixture was quenched with water and aqueous hydrochloric acid (2N) and extracted with ethyl acetate. The combined organic phases were successively washed with water and aqueous saturated sodium chloride, dried over magnesium sulfate, and filtered. The filtrate was concentrated under reduced pressure and the resulting crude residue was purified by automated silica gel column chromatography (Biotage®) eluting with ethyl acetate/hexanes (0 to 40% v/v over 400 mL gradient elution) to yield the title product as a clear oil (6.19 g).

II. 4-tert-Butyl-2-methoxybenzenesulfonic acid (30)

To a cooled (0° C.) solution of 29 (6.19 g; 37.69 mmol) in anhydrous dichloromethane (160 mL) was added chlorosulfonic acid (3.0 mL; 45.22 mmol) dropwise. After addition as complete, the reaction was stirred at 0° C. for an additional 30 minutes, allowed to gradually warm to room temperature and further stirred overnight. The reaction mixture was concentrated under reduced pressure to about 500 mL and washed with aqueous hydrochloric acid (20 nm; 20N). The organic layer was separated and dried over magnesium sulfate which resulted in formation of a white precipitate. Methanol (200 mL) was added to dissolve the precipitate. The organic solution was filtered and concentrated under reduced pressure to yield the title compound as a purple solid (12.07 g).

III. 4-tert-Butyl-2-methoxybenzene-1-sulfonyl chloride (31)

To cooled (0° C.) solution of 30 (12.0 g; 49.12 mmol) in dichloroethane (200 mL) was added phosphorus pentachloride (20.5 g; 98.24 mmol) slowly and portion-wise. After addition was complete, the reaction was heated at reflux overnight, cooled to room temperature, and then concentrated under reduced pressure. The resulting crude residue was purified by automated silica gel column chromatography (Biotage®) eluting with ethyl acetate/hexanes (0 to 50% v/v over 400 mL gradient elution) to give the title product as a dark solid (8.45 g; 65% yield).

IV. Methyl 3-(4-tert-butyl-2-methoxyphenylsulfonamido)thiophene-2-carboxylate (32)

To a solution of 31 (8.45 g; 32.16 mmol) and methyl 3-aminothiophene-2-carboxylate (5.60 g; 35.38 mmol) in tetrahydrofuran (160 mL) at room temperature was added sodium hydride (1.5 g; 38.59 mmol; 60% mineral oil). The reaction mixture was stirred at room temperature under nitrogen for 16 hours (an additional equivalent of sodium hydride was found to be necessary to drive reaction to an acceptable level of completion) and then quenched with water and aqueous hydrochloric acid (2N) and extracted with ethyl acetate. The combined organic phases were successively washed with water and aqueous saturated sodium chloride, dried over magnesium sulfate, and filtered. The filtrate was concentrated under reduced pressure and the resulting crude residue was taken up in ethyl acetate. The resulting precipitate was filtered and triturated from diethyl ether to yield the title compound as a light brown solid (3.58 g).

V. 3-(4-tert-Butyl-2-methoxyphenylsulfonamido)thiophene-2-carboxylic acid (33)

To a solution of 32 (0.25 g; 0.65 mmol) in tetrahydrofuran (15 mL) and methanol (5 mL) was added aqueous sodium hydroxide (10 mL; 2M). The reaction mixture was heated at 75-80° C. for 6 hours, allowed to cool to room temperature and then concentrated under reduced pressure. The resulting residue was dissolved in chloroform (15 mL) and washed with aqueous hydrochloric acid (2×10 mL, 2N). The organic phase was dried over magnesium sulfate, filtered, and concentrated under reduced pressure to yield the title compound as a white solid (188 mg).

VI. 3-(4-tert-Butyl-2-methoxyphenylsulfonamido)thiophene-2-carboxylic acid, disodium salt (34)

To a solution of 33 (188.0 mg; 0.51 mmol) in acetonitrile (10 mL) was added aqueous sodium hydroxide (10.2 mL;

1.01 mmol; 0.1M). The reaction mixture was frozen in a dry ice/acetone bath and lyophilized to yield the title compound as a white solid (202 mg).

Example 9

Preparation of 3-(4-tert-butyl-2-hydroxyphenylsulfonamido)thiophene-2-carboxylic acid, trisodium salt (36)

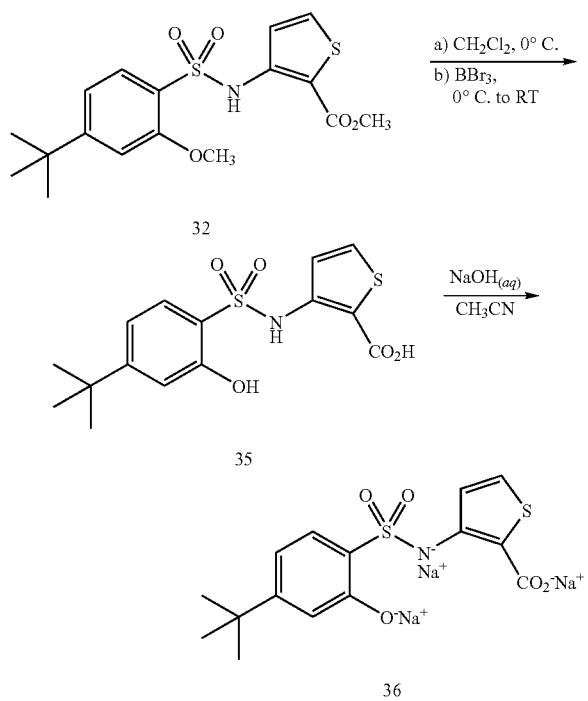

I. 3-(4-tert-Butyl-2-hydroxyphenylsulfonamido)thiophene-2-carboxylic acid (35)

To a cooled (0° C.) solution of 32 (300.0 mg; 0.78 mmol) in dichloromethane (3.9 mL) was added boron tribromide (0.52 mL; 5.47 mL) dropwise. The reaction mixture was stirred at 0° C. then allowed to gradually warm to room temperature. After stirring 4 hours at room temperature, the reaction mixture was cooled to 0° C. again, slowly quenched with methanol; and then diluted with chloroform. The organic layer was washed with water, dried over magnesium sulfate, filtered and concentrated under reduced pressure. The crude residue was re-dissolved in diethyl ether and washed with aqueous sodium hydroxide (2N). The aqueous layer was acidified to pH~2 with concentrated hydrochloric acid and extracted with chloroform (3×). The organic extracts were combined, dried over magnesium sulfate, filtered, and concentrated under reduced pressure. The crude residue was purified by automated silica gel column chromatography (Biotage®) eluting with ethyl acetate/hexanes and then by preparative HPLC to afford the title compound as a white solid (101 mg).

II. 3-(4-tert-Butyl-2-hydroxyphenylsulfonamido)thiophene-2-carboxylic acid, trisodium salt (36)

To a solution of 35 (97.6 mg; 0.27 mmol) in acetonitrile (8 mL) was added aqueous sodium hydroxide (8.2 mL; 0.82 mmol; 0.1M). The reaction mixture was frozen in a dry ice/acetone bath and lyophilized to yield the title compound as a white solid (119 mg).

Example 10

Preparation of 3-(4-tert-butyl-2-cyanophenylsulfonamido)thiophene-2-carboxylic acid, disodium salt (40)

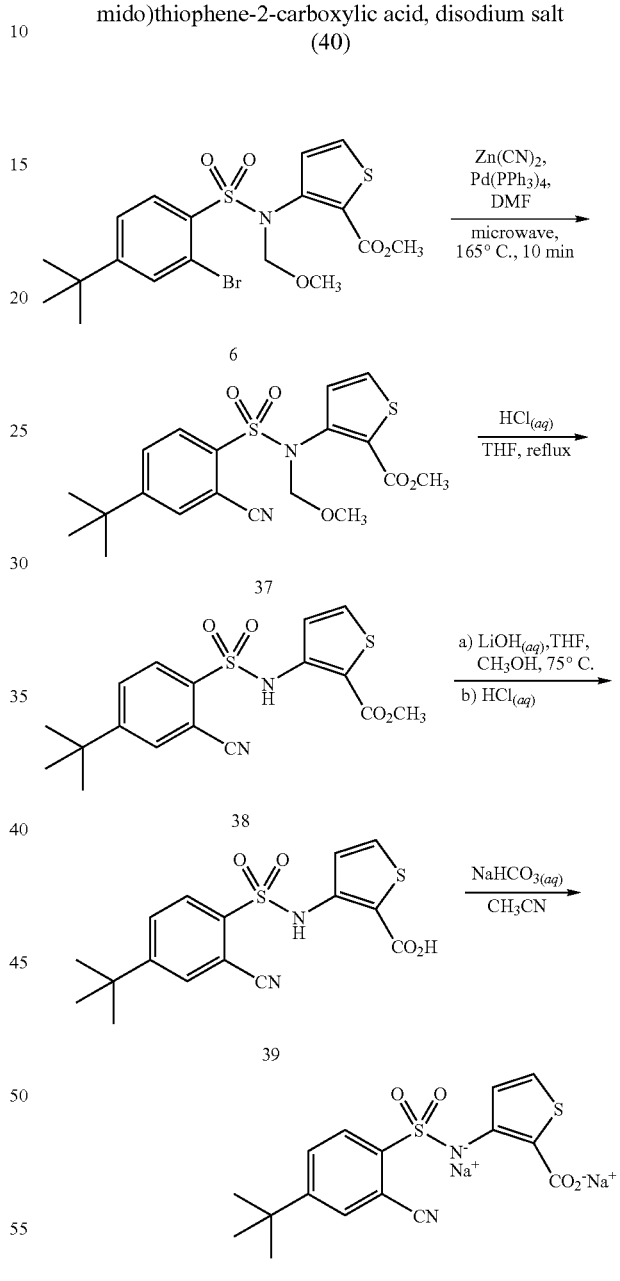

I. Methyl 3-[4-tert-butyl-2-cyano-N-(methoxymethyl)phenylsulfonamido]thiophene-2-carboxylate (37)

To a solution of 6 (0.6 g; 1.29 mol) in anhydrous N,N-dimethylformamide (4 mL) in a 2.5-5.0 mL microwave tube added zinc cyanide (182.8 mg; 1.55 mmol) and tetrakis(triphenylphosphine)palladium(0) (74.5 mg; 0.064 mmol). The reaction tube was purged with nitrogen and subjected to the following microwave reaction conditions: Power=200 W; Time=10 minutes; Temperature=165° C.; Cooling On; Absorption High. The reaction mixture was allowed to cool to room temperature and then was diluted with ethyl acetate (15 mL) and washed with aqueous hydrochloric acid (3×10 mL; 2N). The organic phase was dried over magnesium sulfate, filtered, and concentrated under reduced pressure. The resulting colorless oil was purified by automated silica gel column chromatography (Biotage®) eluting with ethyl acetate/hexanes (0 to 30% v/v over 400 mL gradient elution) to yield the title product as a white solid (340 mg).

II. Methyl 3-(4-tert-butyl-2-cyanophenylsulfonamido)thiophene-2-carboxylate (38)

To a solution of 37 (340.0 mg; 0.80 mmol) in tetrahydrofuran (16 mL) was added aqueous hydrochloric acid (5 mL; 10 mmol; 2N). The reaction mixture was heated at 75° C. for 4 hours, and then additional aqueous hydrochloric acid (3.0 mL; 6N) was added and the reaction mixture further heated at reflux for 4-5 hours. The reaction mixture was allowed to cool to room temperature and then extracted with ethyl acetate (15 mL). The organic layer was separated, dried over magnesium sulfate, filtered, and concentrated under reduced pressure to yield an off-white residue which was triturated from diisopropyl ether to yield the title product as a white solid (240 mg).

III. 3-(4-tert-Butyl-2-cyanophenylsulfonamido)thiophene-2-carboxylic acid (39)

To a solution of 38 (220.0 mg; 0.58 mmol) in tetrahydrofuran (4 mL) and methanol (1 mL) was added aqueous lithium hydroxide (1.45 mL; 2M. The reaction mixture was heated at 75-80° C. for 6 hours, allow ed to cool to room temperature and then concentrated under reduced pressure. The resulting residue was dissolved in chloroform (15 mL) and washed with aqueous hydrochloric acid (2×10 mL; 2N). The organic phase was dried over magnesium sulfate, filtered and the solvent evaporated under reduced pressure. The crude white solid residue was purified by preparative HPLC to yield the title compound as a white solid (110 mg).

IV. 3-(4-tert-Butyl-2-cyanophenylsulfonamido)thiophene-2-carboxylic acid, disodium salt (40)

To a solution of 39 (103.0 mg; 0.28 mmol) in acetonitrile (3 mL) was added aqueous sodium bicarbonate (5.64 mL; 0.56 mmol; 0.1M). The reaction mixture was frozen in a dry ice/acetone bath and lyophilized to yield the title compound as a white solid (110 mg).

Example 11

Preparation of 3-(4-tert-butyl-2-phenethylphenylsulfonamido)thiophene-2-carboxylic acid, disodium salt (44)

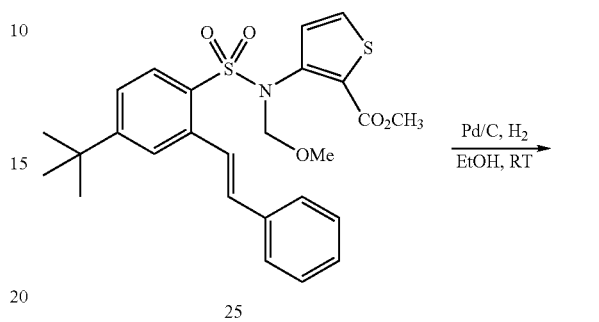

25

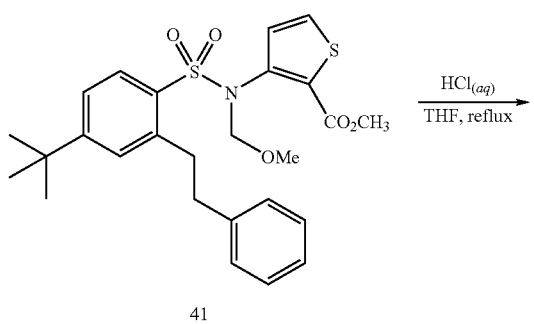

41

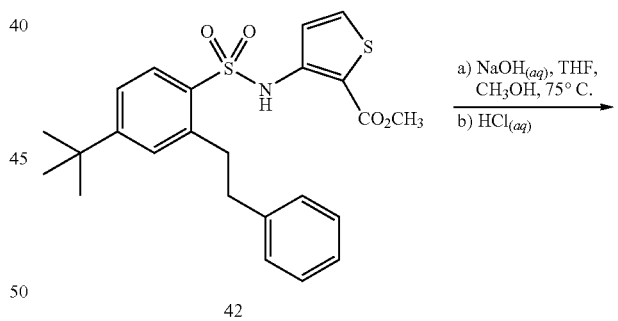

42

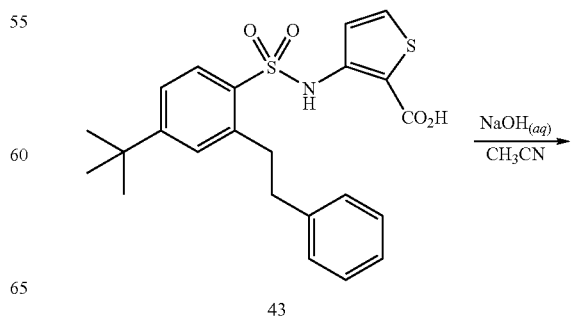

43

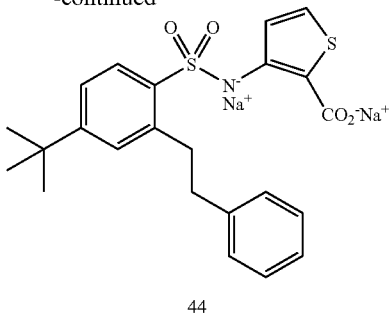

44

I. Methyl 3-[4-tert-butyl-N-(methoxymethyl)-2-phenethylphenylsulfonamido]thiophene-2-carboxylate (41)

A suspension of 25 (206.0 mg; 0.47 mmol) and palladium on carbon (103.0 mg; 0.91 mmol) in ethanol (2.3 mL) was evacuated and filled with hydrogen gas (3×) and then stirred at room temperature under hydrogen overnight. Additional palladium on carbon (103.0 mg) was added and stirring was continued at room temperature for 16 hours. The reaction mixture filtered through celite and the filtrate concentrated under reduced pressure to afford the title compound as a clear oil (143 mg).

II. Methyl 3-(4-tert-butyl-2-phenethylphenylsulfonamido)thiophene-2-carboxylate (42)

To a solution of 41 (143.0 mg; 0.32 mmol) in tetrahydrofuran (6 mL) was added aqueous hydrochloric acid (6 mL; 12 mmol; 2N). The reaction mixture was heated at 75° C. for 4 hours, and then additional aqueous hydrochloric acid (3.0 mL; 6N) was added and the reaction mixture further heated at reflux for 4-5 hours. The reaction mixture was allowed to cool to room temperature and then extracted with ethyl acetate (15 mL). The organic layer was separated, dried over magnesium sulfate, filtered and concentrated under reduced pressure to yield an orange oil residue which was purified by automated silica gel column chromatography (Biotage®) eluting with ethyl acetate/hexanes (0 to 40% v/v over 400 mL gradient elution) to yield the title product as a clear oil (80.0 mg).

III. 3-(4-tert-Butyl-2-phenethylphenylsulfonamido)thiophene-2-carboxylic acid (43)

To a solution of 42 (80.0 mg; 0.17 mmol) in tetrahydrofuran (3 mL) and methanol (1 mL) was added aqueous sodium hydroxide (4 mL; 2M). The reaction mixture was heated at 75-80° C. for 6 hours, allowed to cool to room temperature and then concentrated under reduced pressure. The resulting residue was dissolved in chloroform (15 mL) and washed with aqueous hydrochloric acid (2×10 mL; 2N). The organic phase was dried over magnesium sulfate, filtered, and concentrated under reduced pressure to yield the title compound as a clear oil (64.0 mg).

IV. 3-(4-tert-Butyl-2-phenethylphenylsulfonamido)thiophene-2-carboxylic acid, disodium salt (44)

To a solution of 43 (64.0 mg; 0.14 mmol) in acetonitrile (2 mL) was added aqueous sodium hydroxide (2.9 mL; 0.29 mmol; 0.1M). The reaction mixture was frozen in a dry ice/acetone bath and lyophilized to yield the title compound as a white solid (48.7 mg).

Example 12

Preparation of 3-(2-acetoxy-4-tert-butylphenylsulfonamido)thiophene-2-carboxylic acid, disodium salt (46)

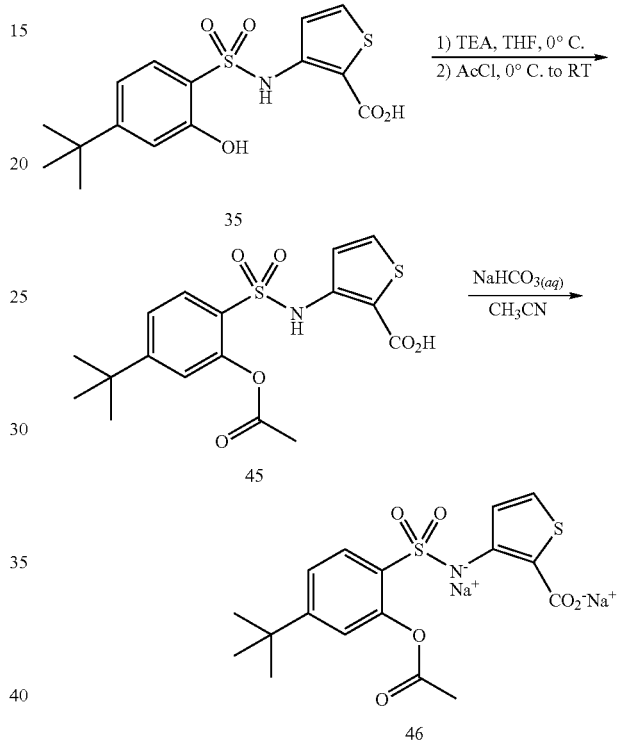

I. 3-(2-Acetoxy-4-tert-butylphenylsulfonamido)thiophene-2-carboxylic acid (45)

To a cooled (0° C.) solution of 35 (137.2 mg; 0.39 mmol) and triethylamine (0.06 mL; 0.46 mmol) in tetrahydrofuran (2 mL) was added acetyl chloride (0.03 mL; 0.46 mmol). After addition was complete, the reaction mixture was stirred at 0° C. for 30 minutes then allowed to warm to room temperature and stirred for 4 hours. The reaction mixture was diluted with ethyl acetate, washed successively with water, aqueous saturated sodium chloride, dried over magnesium sulfate and concentrated under reduced pressure. The crude residue was purified by automated silica gel column chromatography (Biotage®) eluting with ethyl acetate/hexanes to yield the title compound as a white foam (67.0 mg).

II. 3-(2-Acetoxy-4-tert-butylphenylsulfonamido)thiophene-2-carboxylic acid, disodium salt (46)

To a solution of 45 (5.1 mg; 0.013 mmol) in acetonitrile (0.5 mL) was added aqueous sodium bicarbonate (0.26 mL;

0.026 mmol; 0.1M). The reaction mixture was frozen in a dry ice/acetone bath and lyophilized to yield the title compound as a white solid (6.6 mg).

Example 13

Preparation of 3-(4-tert-butyl-2-methylphenylsulfonamido)thiophene-2-carboxylic acid, disodium salt (50)

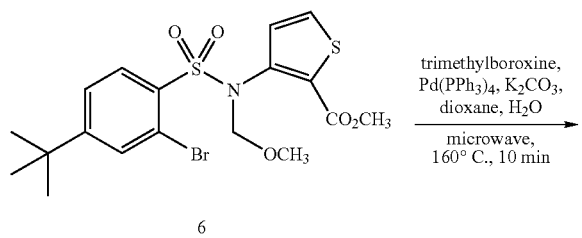

6

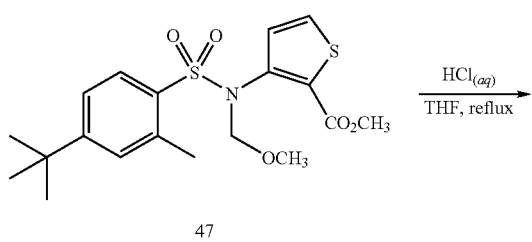

47

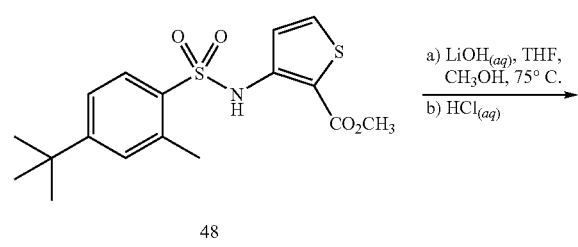

48

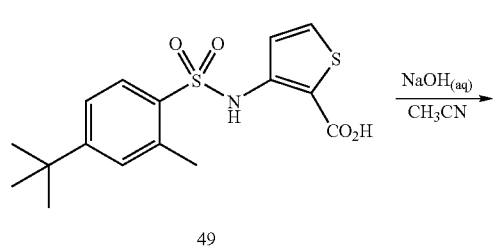

49

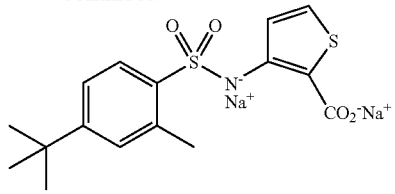

50

I. Methyl 3-[4-tert-butyl-N-(methoxymethyl)-2-methylphenylsulfonamide]thiophene-2-carboxylate (47)

A 2.5-5.0 mL microwave reaction tube was successively charged with 6 (200.0 mg; 0.43 mmol), trimethylboroxine (65.78 μl; 0.48 mmol), potassium carbonate (179.0 mg; 1.29 mmol), tetrakis(triphenylphosphine)palladium(0) (49.9 mg; 0.043 mmol), dioxane (3 mL) and water (0.5 mL). The reaction tube was purged with nitrogen and subjected to the following microwave conditions: Temperature=160° C.; Power=250 W; Time=10 minutes; Cooling On; Absorption High. The reaction mixture was allowed to cool to room temperature and then diluted with ethyl acetate (15 mL) and washed with hydrochloric acid (3×10 mL; 2N solution). The organic layer was dried over magnesium sulfate, filtered, and concentrated under reduced pressure. The resulting crude residue was purified by automated silica gel column chromatography (Biotage®) eluting with ethyl acetate/hexanes (0 to 15% v/v over 400 mL gradient elution) to give the title product as a yellow oil (450 mg; yield is from purification of 5 combined reaction batches obtained as described above).

II. Methyl 3-(4-tert-butyl-2-methylphenylsulfonamido)thiophene-2-carboxylate (48)

To a solution of 47 (439.0 mg; 1.06 mmol) in tetrahydrofuran (20 mL) was added aqueous hydrochloric acid (10 mL; 20 mmol; 2N). The reaction mixture was heated at 75° C. for 4 hours, and then additional aqueous hydrochloric acid (3.0 mL; 6N) was added and the reaction mixture further heated at reflux for 4-5 hours. The reaction mixture was allowed to cool to room temperature and then extracted with ethyl acetate (15 mL). The organic layer was separated, dried over magnesium sulfate, filtered, and concentrated under reduced pressure to yield an off-white residue which was triturated from diisopropyl ether to yield the title product as an off-white solid (260 mg).

III. 3-(4-tert-Butyl-2-methylphenylsulfonamido)thiophene-2-carboxylic acid (49)

To a solution of 48 (256.0 mg; 0.69 mmol) in tetrahydrofuran (15 mL) and methanol (3 mL) was added aqueous lithium hydroxide (3.5 mL; 2M). The reaction mixture was heated at 75-80° C. for 6 hours, allowed to cool to room temperature and then concentrated under reduced pressure. The resulting residue was dissolved in chloroform (15 mL) and washed with aqueous hydrochloric acid (2×10 mL; 2N). The organic phase was dried over magnesium sulfate, filtered and the solvent evaporated under reduced pressure. The crude beige residue was purified by automated silica gel column chromatography (Biotage®) eluting with ethyl acetate/hexanes (0 to 10% v/v over 350 mL gradient elution) to give the title product as a white solid (187 mg).

IV. 3-(4-tert-Butyl-2-methylphenylsulfonamido) thiophene-2-carboxylic acid, disodium salt (50)

To a solution of 49 (187.0 mg; 0.53 mmol) in acetonitrile (10 mL) was added aqueous sodium hydroxide (10.6 mL; 1.06 mmol; 0.1M). The reaction mixture was frozen in a dry ice/acetone bath and lyophilized to yield the title compound as a white solid (198 mg).

Example 14

Preparation of 3-(4-sec-butylphenylsulfonamido) thiophene-2-carboxylic acid, disodium salt (54)

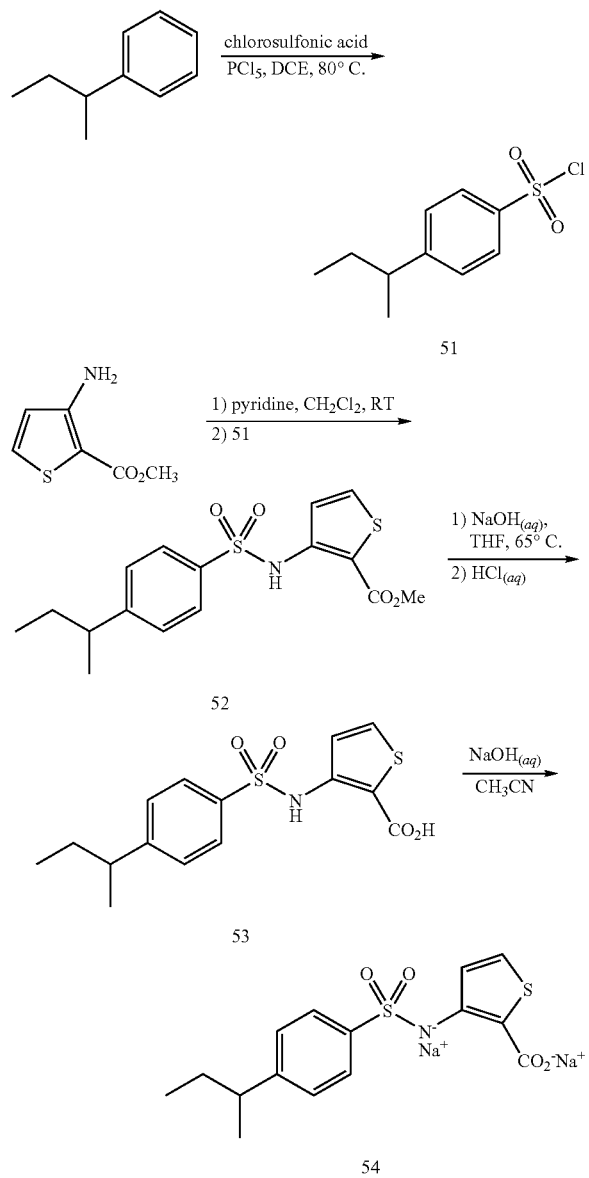

I. 4-sec-Butylbenzenesulfonyl chloride (51)

To a solution of commercially available sec-butylbenzene (1.34 g; 10 mmol) in 1,2-dichloroethane (50 mL) was added phosphorus pentachloride (2.5 g; 12 mmol) followed by chlorosulfonic acid (1.3 mL; 20 mmol) slowly. The mixture was heated at 80° C. overnight, then cooled to room temperature and mixed with ice water (150 mL). The organic phase was separated, and the aqueous phase was extracted with dichloromethane (2×10 mL). The organic phases were combined and dried over magnesium sulfate and concentrated under reduced pressure to give an orange oil which was used without further purification (2.3 g).

II. Methyl 3-[4-(sec-butyl)phenylsulfonamido] thiophene-2-carboxylate (52)

To a solution of methyl 3-aminothiophene-2-carboxylate (0.68 g; 4.3 mmol) in pyridine (0.52 mL; 6.4 mmol) and anhydrous dichloromethane (15 mL), was added a solution of 51 (1.0 g; 4.3 mmol) in dichloromethane (3 mL). After stirring 16 hours at room temperature, the reaction was mixed with water (50 mL), and the organic phase was separated. The aqueous phase was extracted with dichloromethane (2×10 mL), and the combined organic phases were dried over magnesium sulfate, filtered, and concentrated under reduced pressure. The crude residue was purified by flash chromatography on silica gel eluting with ethyl acetate/hexanes (0 to 25% v/v gradient elution) to yield the title product as a white solid (0.75 g).

III. 3-(4-sec-Butylphenylsulfonamido)thiophene-2-carboxylic acid (53)

To a solution of 52 (0.75 g, 2.12 mmol) in tetrahydrofuran (10 mL) was added aqueous sodium hydroxide (5 mL, 2N). The reaction mixture was heated at 65° C. for 2 days, allowed to cool to room temperature and then acidified to pH 5 with aqueous hydrochloric acid (2N) and extracted with tetrahydrofuran (3×5 mL). The combined organic phases were dried over magnesium sulfate, filtered and concentrated under reduced pressure to yield a golden oil (0.7 g), which later solidified. A portion of the crude residue was purified by preparative HPLC to afford the title compound as a white solid (129 mg).

IV. 3-(4-sec-Butylphenylsulfonamido)thiophene-2-carboxylic acid, disodium salt (54)

To a solution of 53 (129 mg; 0.38 mmol) in acetonitrile (2 mL) was added aqueous sodium hydroxide (7.6 mL; 0.76 mmol; 0.1N). The reaction mixture was frozen in a dry ice/acetone bath and lyophilized to yield the title compound as a white solid (145 mg).

Example 15

Preparation of 3-(4-tert-butyl-N-methylphenylsulfonamido)thiophene-2-carboxylic acid, sodium salt (58)

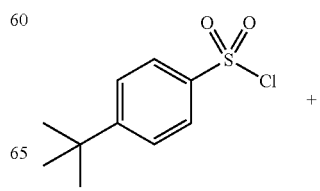 +

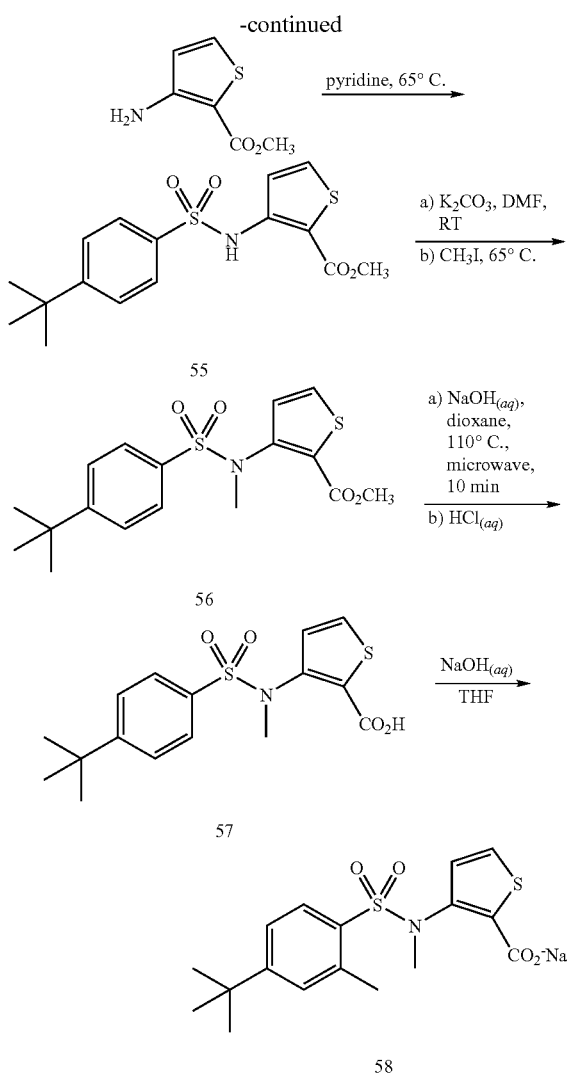

I. Methyl 3-(4-tert-butylphenylsulfonamido) thiophene-2-carboxylate (55)

In an appropriate vessel, methyl 3-aminothiophene-2-carboxylate (2.5 g; 15.9 mmol) was combined with 4-tert-butylbenzene sulfonyl chloride (3.70 g; 15.9 mmol) and dissolved by addition of pyridine (5.00 mL; 63.2 mmol). The reaction mixture was heated at 65° C. for 2 hours cooled to room temperature, diluted with aqueous hydrochloric acid (100 mL; 2M) and extracted with dichloromethane (3×30 mL). The combined organic extracts were washed with aqueous hydrochloric acid (100 mL), dried over magnesium sulfate, filtered, and concentrated under reduced pressure. The resulting crude solid was recrystallized from a minimal amount of isopropanol to give the title product as a yellow solid (5.2 g).

II. Methyl 3-(4-tert-butyl-N-methylphenylsulfonamido)thiophene-2-carboxylate (56)

To a solution of 55 (0.15 g; 0.42 mmol) in N,N-dimethylformamide (2 mL) at room temperature was added potassium carbonate (0.282 g; 2.12 mmol) followed by iodomethane (0.053 mL; 0.85 mmol). The reaction mixture was heated at 65° C. for 12 hours, cooled to room temperature, diluted with aqueous hydrochloric acid (50 mL; 2M) and extracted with dichloromethane (3×25 mL). The combined organic extracts were dried over magnesium sulfate, filtered, and concentrated under reduced pressure to yield a crude residue that was purified by chromatography on silica gel eluting with a 0 to 10% ethyl acetate/hexanes gradient to give the title product (0.129 g).

III. 3-(4-tert-Butyl-N-methylphenylsulfonamido) thiophene-2-carboxylic acid (57)

In an appropriate microwave vessel, a solution of 56 (0.129 g; 0.35 mmol) in dioxane (2 mL) at 25° C. was added aqueous sodium hydroxide (1.5 mL; 3.0 mmol; 2M). The vessel was sealed and brought to 110° C. for 10 minutes via the Biotage Initiator Microwave Synthesizer. Upon cooling to 25° C., the mixture was diluted with water (10 mL) and washed with diethyl ether (5 mL). The aqueous layer was treated with concentrated hydrochloric acid to pH 1 and extracted with dichloromethane (2×20 mL). The organic layers were combined, washed with water (5×25 mL), dried over magnesium sulfate, filtered, and concentrated under reduced pressure to yield the title product (0.54 g).

IV. 3-(4-tert-Butyl-N-methylphenylsulfonamido) thiophene-2-carboxylic acid, sodium salt (58)

To a solution of 57 (0.054 g; 0.15 mmol) in tetrahydrofuran (2 mL) was added aqueous sodium hydroxide (0.15 mL; 0.15 mmol; 1.0M). After 15 minutes, the solution was concentrated under reduced pressure and the resulting residue was dissolved in 1:1 acetonitrile/water (21 mL). The reaction mixture was frozen in a dry ice/acetone bath and lyophilized to yield the title compound as a yellow solid (0.017 g).

Example 16

Preparation of 3-(4-tert-butylphenylsulfonamido) thiophene-2-carboxylic acid, disodium salt (60)

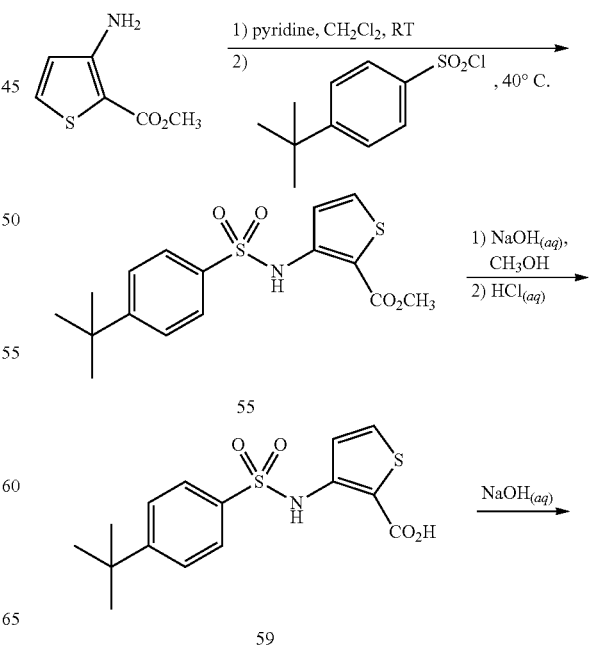

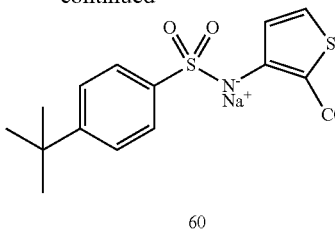

60

I. Methyl 3-(4-tert-butylphenylsulfonamido)
thiophene-2-carboxylate (55)

To a solution of methyl 3-aminothiophene-2-carboxylate (0.55 g; 3.5 mmol) in pyridine (2 mL) and dichloromethane (2 mL) was added 4-tert-butylbenzenesulfonyl chloride (0.98 g; 4.2 mmol). The resulting mixture was warmed to 40° C. to aid in solubility, then stirred at room temperature for 48 hours. The reaction mixture was diluted with dichloromethane and washed with aqueous hydrochloric acid (2N). The aqueous layer was separated and extracted with dichloromethane. The organic layers were combined, dried over anhydrous sodium sulfate, decanted, and filtered through a and of silica. The silica was washed with dichloromethane. The eluant was combined with hexanes and allowed to stand. After 24 hours the resulting solid product was collected by filtration to give the desired product as a white solid (817 mg).

II. 3-(4-tert-Butylphenylsulfonamido)thiophene-2-carboxylic acid (59)

To a solution of 55 (0.817 g; 2.31 mmol) in methanol (4.5 mL) was added aqueous sodium hydroxide (9.2 mL; 1N). After the reaction was complete, the mixture was partitioned between diethyl ether and water; the organic layer was separated and set aside. The aqueous layer was acidified with excess aqueous hydrochloric acid (2N) and extracted with ethyl acetate (2×). The diethyl ether and ethyl acetate organic layers were combined, dried over sodium sulfate, decanted, and concentrated under reduced pressure. The resulting residue yielded the desired product a white solid from a mixture of hexanes and dichloromethane (0.54 g).

III. 3-(4-tert-Butylphenylsulfonamido)thiophene-2-carboxylic acid, disodium salt (60)

The resulting 3-(4-tert-Butylphenylsulfonamido)thiophene-2-carboxylic acid, 59 (0.342 g; 1.01 mmol) was treated directly with a solution of aqueous sodium hydroxide (19.2 mL; 2.02 mmol; 0.1050N). The reaction mixture was frozen in a dry ice/acetone bath and lyophilized to give a white solid (0.39 g)

Example 17

Preparation of 3-(Naphthalene-2-sulfonamido) thiophene-2-carboxylic acid, disodium salt (63)

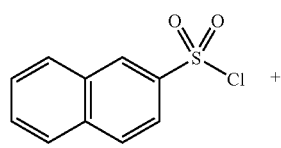

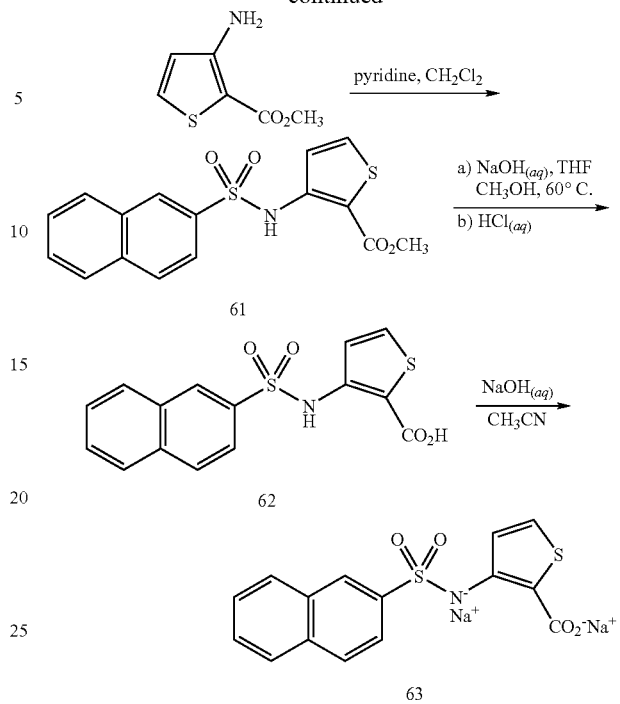

I. Methyl 3-(naphthalene-2-sulfonamido)thiophene-2-carboxylate (61)

To a flask containing a stir bar was added methyl 3-aminothiophene-2-carboxylate (0.74 g; 4.70 mmol), 2-naphthylenesulfonyl chloride (1.09 g; 4.80 mmol), and anhydrous dichloromethane (15 mL). The reaction mixture was stirred at room temperature under nitrogen and then pyridine (1.0 mL; 12.9 mmol) was added. After stirring overnight, aqueous hydrochloric acid (75 mL; 1N) was added. The aqueous layer was separated and extracted with dichloromethane (15 mL). The organic layer was separated and concentrated under reduced pressure. The resulting crude product was purified by automated silica gel column chromatography (Biotag®) eluting with ethyl acetate/hexanes (0 to 30% v/v gradient elution) to give the title product as a white solid (1.45 g).

II. 3-(Naphthalene-2-sulfonamido)thiophene-2-carboxylic acid (62)

To a flask containing 61 (1.10 g; 3.16 mmol) was added tetrahydrofuran (12 mL) and aqueous sodium hydroxide (8 mL; 2M). Water (4 mL), methanol (4 mL) and additional tetrahydrofuran (5 mL) were added to the reaction mixture to aid in dissolution of the starting methyl ester. The reaction was heated in an oil bath overnight at 60° C. and then diluted with water (50 mL) and dichloromethane (50 mL). The aqueous phase was separated, acidified with aqueous hydrochloric acid (1N), and extracted with ethyl acetate (3×20 mL). The organic extracts were combined, dried with sodium sulfate, filtered, and concentrated under reduced pressure. The resulting tan solid was recrystallized from hexanes/ethyl acetate to yield the desired product as a tan solid (522 mg).

III. 3-(Naphthalene-2-sulfonamido)thiophene-2-carboxylic acid, disodium salt (63)

To a round bottom flask containing 62 (468 mg; 1.45 mmol) was added acetonitrile (4 mL) and aqueous sodium hydroxide (27.6 mL; 2.90 mmol; 0.105M). The resulting suspension was heated to dissolve all solids and then filtered. After cooling to room temperature, the filtrate was frozen in a dry ice acetone bath and lyophilized to give a white solid (540 mg).

Example 18

Preparation of 3-(4-(1,1-Dimethylpropyl)phenylsulfonamido)thiophene-2-carboxylic acid, sodium salt (66)

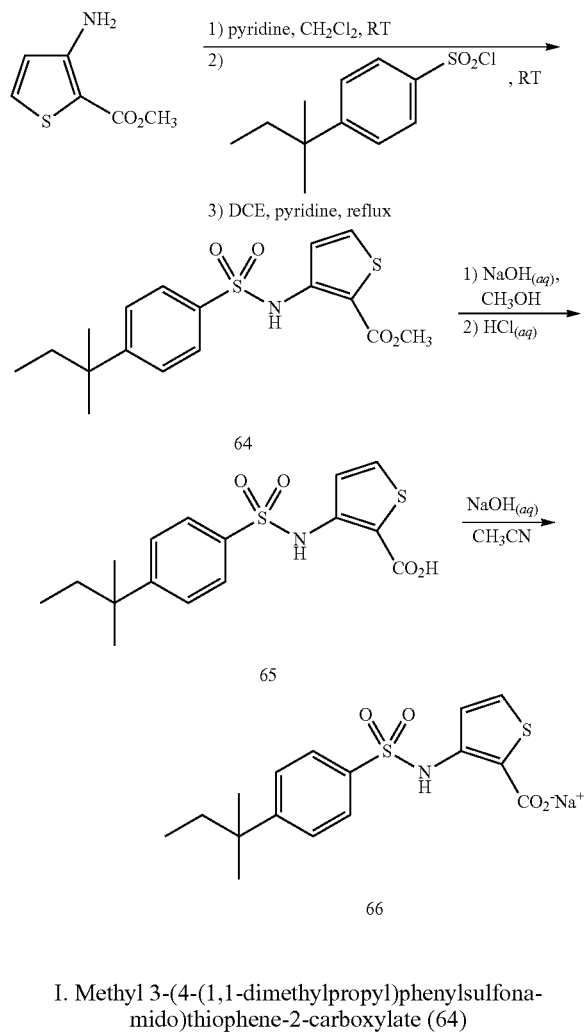

I. Methyl 3-(4-(1,1-dimethylpropyl)phenylsulfonamido)thiophene-2-carboxylate (64)

To a solution of methyl 3-aminothiophene-2-carboxylate (0.184 g; 1.17 mmol) in dichloromethane (2 mL) were added pyridine (0.199 mL; 2.34 mmol) and 4-(1,1-dimethylpropyl)benzenesulfonyl chloride (0.289 g; 1.17 mmol) sequentially. The reaction mixture was stirred for 24 hours at room temperature and then 1,2-dichloroethane (2 mL) and pyridine (1 mL) were added. The reaction mixture was heated at 70° C. for 24 hours, cooled to room temperature, diluted with ethyl acetate and acidified with aqueous hydrochloric acid (2N). The organic layer was separated, concentrated under reduced pressure, and the resulting crude product was purified by chromatography on silica gel eluting with ethyl acetate/hexanes (1:6 v/v) to give the desired product as a white solid (0.21 g).

II. 3-(4-(1,1-Dimethylpropyl)phenylsulfonamido)thiophene-2-carboxylic acid (65)

To a solution of 64 (210 mg; 0.14 mmol) in methanol (2 mL) was added aqueous sodium hydroxide (2 mL; 2N) and the resulting mixture was stirred overnight at room temperature. The solvent was removed under reduced pressure and the resulting residue was dissolved in water, acidified to pH 2 with aqueous hydrochloric acid (2N), and extracted with ethyl acetate. The combined organic layers were dried over magnesium sulfate, filtered, and concentrated under reduced pressure. The desired product was obtained from dichloromethane and hexanes as a yellow solid (75 mg).

III. 3-(4-(1,1-Dimethylpropyl)phenylsulfonamido)thiophene-2-carboxylic acid, sodium salt (66)

The resulting 3-(4-(1,1-dimethylpropyl)phenylsulfonamido)thiophene-2-carboxylic acid, 65 (0.072 g; 0.20 mmol) was dissolved in a minimum amount of acetonitrile, heating as necessary until the solid dissolved. A solution of aqueous sodium hydroxide (1.94 mL; 0.20 mmol; 0.1050N) was added and then the acetonitrile was removed under reduced pressure. The resulting aqueous mixture was frozen in a dry ice/acetone bath and lyophilized to give an off-white solid (0.070 g).

Example 19

Preparation of 3-(4-butyl-2-chlorophenylsulfonamido)thiophene-2-carboxylic acid, disodium salt (73)

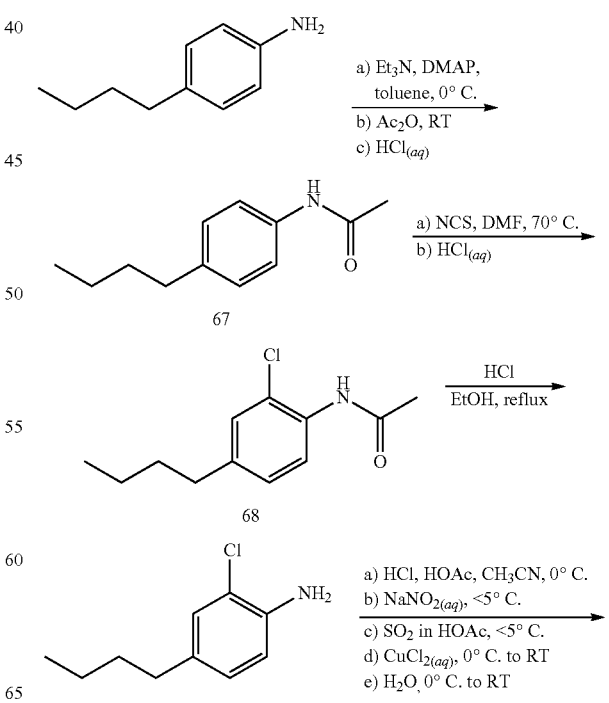

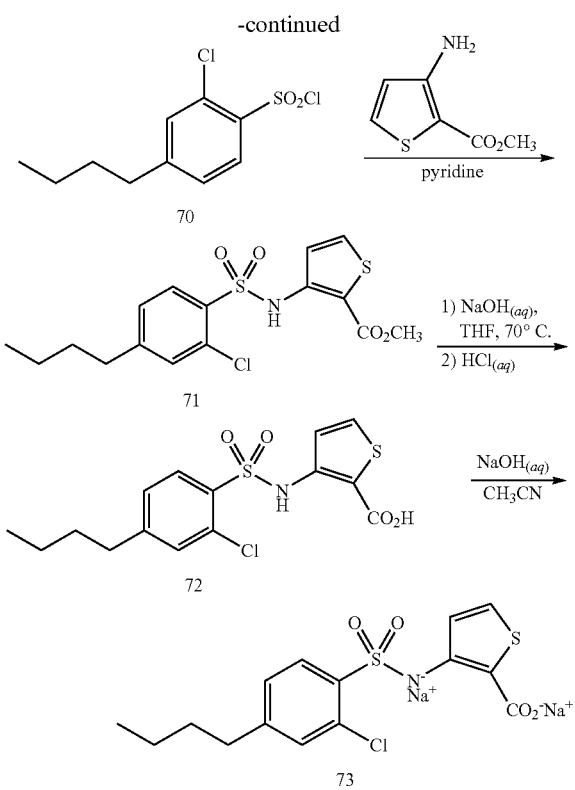

I. N-(4-Butylphenyl)acetamide (67)

To 4-butyl aniline (20 g; 134 mmol) dissolved in toluene (160 mL) with stirring was added 4-dimethylaminopyridine (0.82 g; 6.70 mmol) and triethylamine (26.0 mL; 188 mmol). The mixture was then treated with acetic anhydride (15.2 mL; 161 mmol) dropwise via an addition funnel over 30 minutes. After addition, the ice bath was removed and the reaction mixture was stirred for 12 hours at room temperature. The mixture was poured into aqueous hydrochloric acid (240 mL; 2M) and stirred 20 minutes. The layers were separated and the organic layer was washed with water. The organic layer was separated and crystals formed while standing. The resulting precipitate was isolated by filtration and dried under vacuum to give the title product as white crystals (15.0 g).

II. N-(4-Butyl-2-chlorophenyl)acetamide (68)

A mixture of 67 (7.0 g; 36.6 mmol) and N-chlorosuccinimide (7.8 g; 58.6 mmol) was dissolved in N,N-dimethylformamide (70 mL). The reaction was heated at 70° C. for 6 hours, cooled to room temperature, then poured into aqueous hydrochloric acid (400 mL; 2M), and stirred for 15 minutes. The resulting precipitate was isolated by filtration and dried under vacuum to give the title product as an orange solid (8.54 g).

III. 2-Chloro-4-butylaniline (69)

To a suspension of 68 (8.54 g; 37.9 mmol) in ethanol (20 mL) was added concentrated hydrochloric acid (20 mL). The resulting mixture was heated at 120° C. for 5 hours, allowed to cool to room temperature, then made basic with aqueous potassium hydroxide, and extracted with methyl tert-butyl ether (3×75 mL). The combined organic extracts were washed with aqueous saturated sodium chloride, dried over sodium sulfate, and filtered. The filtrate was concentrated under reduced pressure to give the title product as a dark oil (5.89 g).

IV. 4-Butyl-2-chlorobenzene-1-sulfonyl chloride (70)

In a 1 liter 3-necked round bottom flask equipped with a thermometer and addition funnel, 69 (5.89 g; 32.1 mmol) was dissolved in acetonitrile (250 mL) and cooled to 0° C. via an ice bath. Upon reaching the desired temperature, the reaction mixture was treated with glacial acetic acid (26 mL; 449 mmol) and concentrated hydrochloric acid (13 mL; 154 mmol) with stirring. The reaction was treated with a solution of sodium nitrite (2.66 g; 38.5 mmol) dissolved in water (10 mL) via syringe dropwise at a rate sufficient to keep the reaction temperature below 5° C. (about 20 minutes). After stirring for 30 minutes, the reaction was treated with a saturated solution of sulfur dioxide dissolved in glacial acetic acid (137 mL; 30% w/w) dropwise via the addition funnel. The solution was prepared by passing gaseous sulfur dioxide through a gas dispersion tube into glacial acetic acid for 30 minutes. The rate of addition of the sulfur dioxide saturated acetic acid solution was such that the internal reaction temperature did not rise above 5° C. (about 30 minutes) in 125 mL portions dictated by the size of the addition funnel. The remaining portions of the solution not added were infused with sulfur dioxide to maintain saturation. Following addition of the sulfur dioxide saturated acetic acid, the reaction was treated with a solution of copper(II) chloride dihydrate (6.84 gm, 40.1 mmol) dissolved in water (10 mL) over 5 minutes. The reaction stirred for 30 minutes at 0° C. then warmed to room temperature where it stirred for 16 hours. The reaction was then poured into ice water (1.5 L) and stirred 30 minutes. The resulting oil was isolated by extraction (3×200 mL 10% ethyl acetate/hexanes). The organic extracts were washed with water, aqueous saturated sodium chloride, dried over sodium sulfate, passed through a silica plug, and concentrated under reduced pressure to give the title product as an orange oil (7.44 g).

V. Methyl 3-(4-butyl-2-chlorophenylsulfonamido) thiophene-2-carboxylate (71)

A solution of 70 (2.5 g; 9.36 mmol) and methyl 3-aminothiophene-2-carboxylate (1.62 g; 10.30 mmol) in anhydrous pyridine (12.0 mL; 144 mmol) was stirred at room temperature for 12 hours. The reaction mixture was concentrated under reduced pressure and the resulting residue was purified by automated silica gel column chromatography (Biotage®) eluting with ethyl acetate/hexanes (0 to 20% v/v) to give the title compound as a clear oil (1.79 g).

VI. 3-(4-Butyl-2-chlorophenylsulfonamido) thiophene-2-carboxylic acid (72)

To a solution of 71 (1.75 g; 4.5 mmol) in tetrahydrofuran (25 mL) was added aqueous sodium hydroxide (20 mL; 6M) and then heated at 70° C. for 24 hours. The reaction mixture was allowed to cool to room temperature and then acidified to pH 2 with concentrated hydrochloric acid. The organic solvent was removed under reduced pressure and the resulting aqueous solution was extracted with chloroform (3×20 mL). The organic extracts were combined and successively washed with water and aqueous saturated sodium chloride, dried over sodium sulfate and filtered. The filtrate was concentrated under reduced pressure to yield the title compound as an off-white solid (1.57 g).

VII. 3-(4-Butyl-2-chlorophenylsulfonamido)thiophene-2-carboxylic acid, disodium salt (73)

To a solution of 72 (184 mg; 0.49 mmol) in acetonitrile (5 mL) was added aqueous sodium hydroxide (9.62 mL; 0.98 mmol; 0.1023M). The reaction mixture was frozen in a dry ice/acetone bath and lyophilized to yield the title compound as a white powder (201 mg).

Example 20

Preparation of 3-(4-bromophenylsulfonamido)thiophene-2-carboxylic acid, disodium salt (76)

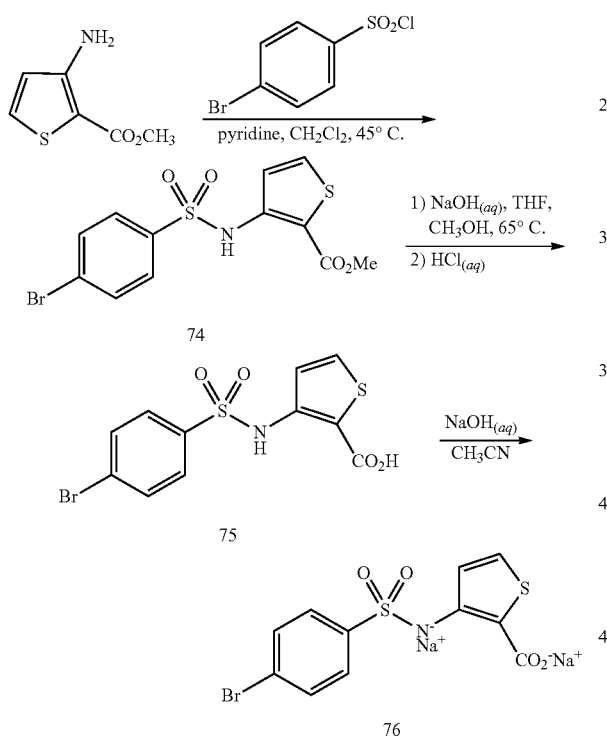

I. Methyl 3-(4-bromophenylsulfonamido)thiophene-2-carboxylate (74)

To a solution of methyl 3-aminothiophene-2-carboxylate (2.98 g; 11.7 mmol) in anhydrous dichloromethane (32 mL) were added pyridine (1.54 mL; 19.0 mmol) and 4-bromobenzenesulfonyl chloride (1.49 g; 9.5 mmol) in one portion. The reaction mixture was heated at 45° C. for 71 hours, allowed to cool to room temperature, and then diluted with dichloromethane (100 mL). The resulting mixture was successively washed with aqueous hydrochloric acid (50 mL; 2N) and aqueous saturated sodium chloride (50 mL), dried over magnesium sulfate, filtered and the filtrate was concentrated under reduced pressure to yield an off-white solid. The crude product was dissolved in dichloromethane (100 mL) and treated with aqueous sodium hydroxide (60 mL; 2N) resulting in a white precipitation. The white solid was isolated by filtration and washed with dichloromethane (50 mL). The white solid was then acidified with aqueous hydrochloric acid (60 mL; 6N) and extracted with dichloromethane (2×100 mL). The organic extracts were combined, washed with aqueous saturated sodium chloride, dried over magnesium sulfate, filtered, and concentrated under reduced pressure to yield the title compound as a pale yellow solid (2.53 g).

II. 3-(4-Bromophenylsulfonamido)thiophene-2-carboxylic acid (75)

To a solution of 74 (0.20 g; 5.32 mmol) in tetrahydrofuran (2.7 mL) were added aqueous sodium hydroxide (2.7 mL; 2N) and methanol (1.4 mL), sequentially. The reaction mixture was heated at 65° C. for 18 hours, allowed to cool to room temperature, and then extracted with aqueous sodium hydroxide (20 mL; 2N). The aqueous layer was washed with diethyl ether (30 mL×2), acidified with aqueous hydrochloric acid (20 mL; 6N), and extracted with dichloromethane (40 mL). The organic layer was successively washed with water (30 mL) and aqueous saturated sodium chloride (30 mL), dried over magnesium sulfate, and filtered. The filtrate was concentrated under reduced pressure to yield the title compound as a white solid (0.18 g).

III. 3-(4-Bromophenylsulfonamido)thiophene-2-carboxylic acid, disodium salt (76)

To a solution of 75 (139 mg; 0.38 mmol) in acetonitrile (7 mL) was added aqueous sodium hydroxide (7.67 mL. 0.77 mmol; 0.1N). The reaction mixture was frozen in a dry ice/acetone bath and lyophilized to yield the title compound as a white solid (105 mg).

Example 21

Preparation of 3-(5,6,7,8-tetrahydronaphthalene-2-sulfonamido)thiophene-2-carboxylic acid, disodium salt (80)

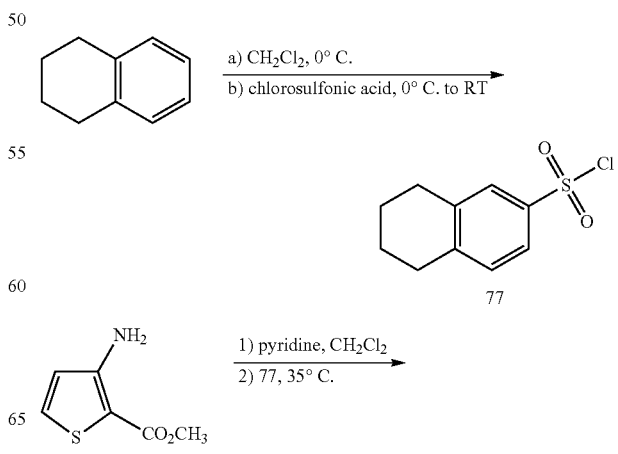

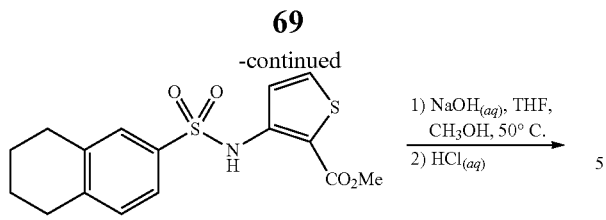

78

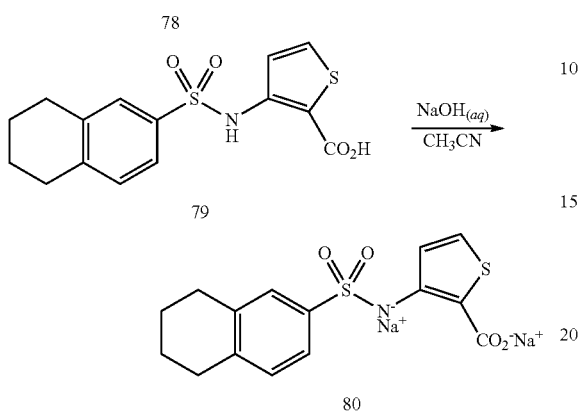

79

80

I. 5,6,7,8-Tetrahydronaphthalene-2-sulfonyl chloride (77)

To a solution of commercially available 5,6,7,8-tetrahydronaphthalene (1.45 g; 11.3 mmol) in dichloromethane (22.7 mL) cooled to 0° C. was added chlorosulfonic acid (0.9 mL; 13.5 mmol) fast dropwise. The reaction mixture was stirred overnight warming to room temperature gradually. The reaction mixture was used in the next reaction directly without purification.

II. Methyl 3-(5,6,7,8-tetrahydronaphthalene-2-sulfonamido)thiophene-2-carboxylate (78)

Synthesized as described for 52 except using a solution of 77 (1.30 g; 5.64 mmol) in anhydrous dichloromethane (11 mL), methyl 3-aminothiophene-2-carboxylate (892 mg; 5.67 mmol), pyridine (1.14 mL; 14.10 mmol) and anhydrous dichloromethane (11 mL). This afforded the desired product as yellow solid (0.62 g).

III. 3-(5,6,7,8-Tetrahydronaphthalene-2-sulfonamido)thiophene-2-carboxylic acid (79)

To a solution of 78 (71 mg, 0.20 mmol) in tetrahydrofuran (1 mL) were added aqueous sodium hydroxide (2 mL; 2N) and methanol (2 mL). The reaction mixture was heated at 50° C. for 27 hours, allowed to cool to room temperature, and then extracted with aqueous sodium hydroxide (20 mL; 2N). The aqueous layer was washed with diethyl ether (30 mL×2), acidified with aqueous hydrochloric acid (20 mL; 6N), and extracted with dichloromethane (40 mL). The organic layer was separated, dried over magnesium sulfate, and filtered. The filtrate was concentrated under reduced pressure to yield the title compound as a white solid (51 mg).

IV. 3-(5,6,7,8-Tetrahydronaphthalene-2-sulfonamido)thiophene-2-carboxylic acid, disodium salt (80)

A solution of 79 (51 mg; 0.14 mmol) in aqueous sodium hydroxide (2.64 mL; 0.28 mmol; 0.1050N) was achieved by sonication for 2 minutes. The reaction mixture was filtered, and the filtrate was frozen in a dry ice/acetone bath and lyophilized to yield the title compound as a white solid (47 mg).

Example 22

Preparation of 3-(2'-methylbiphenyl-3-ylsulfonamido)thiophene-2-carboxylic acid, disodium salt (84)

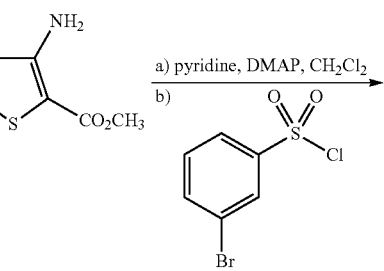

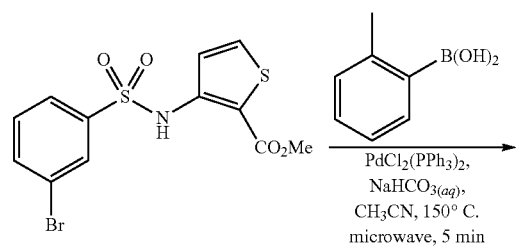

81

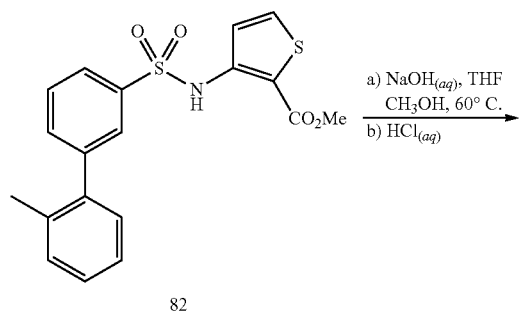

82

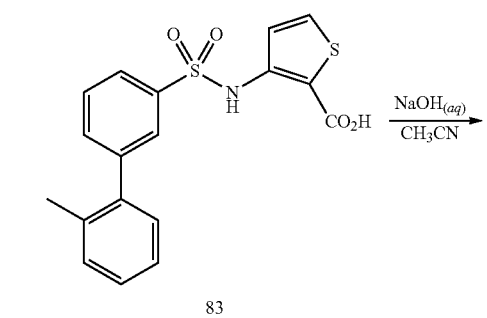

83

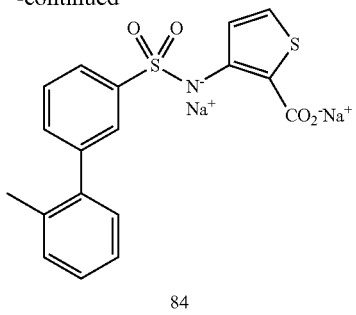

84

I. Methyl 3-(3-bromophenylsulfonamido)thiophene-2-carboxylate (81)

To a solution of commercially available methyl 3-aminothiophene-2-carboxylate (1.25 g; 7.9 mmol) in anhydrous dichloromethane (19.8 mL) was added pyridine (1.9 mL; 23.7 mmol), 4-dimethylaminopyridine (0.10 g; 0.8 mmol), and commercially available 3-bromobenzene-1-sulfonyl chloride (2.43 g; 9.5 mmol), sequentially. After addition was complete, the reaction was stirred at room temperature for 48 hours. The reaction was extracted with dichloromethane (50 mL) and washed with aqueous sodium hydroxide (75 mL; 2N), which resulted in the precipitation of a large quantity of white solid (sodium salt of 81). The solid was isolated by filtration on filter paper and was washed with dichloromethane (50 mL×2). The white solid was transferred to a 500-mL Erlenmeyer flask, suspended in dichloromethane (100 mL), and treated with aqueous hydrochloric acid (80 mL; 6N). The mixture was stirred at room temperature for 1 hour, and the dichloromethane layer was isolated. The dichloromethane extracts were washed with water (60 mL) and aqueous saturated sodium chloride (60 mL), dried over magnesium sulfate, filtered, and concentrated under reduced pressure to yield the title compound as a pale pink solid (2.79 g).

II. Methyl 3-(2'-methylbiphenyl-3-ylsulfonamido)thiophene-2-carboxylate (82)

A 2.5-5.0 mL microwave reaction tube was successively charged with 81 (136 mg; 0.36 mmol), o-tolylboronic acid (67 mg; 0.49 mmol), bis(triphenylphosphine)palladium(II) dichloride (14 mg; 0.02 mmol), acetonitrile (1 mL) and aqueous saturated sodium bicarbonate (0.25 mL). The reaction vessel was subjected to the following microwave conditions: Temperature=150° C.; Time=5 minutes; Power=250 W; Cooling on; Absorption=High. After cooling to room temperature, the reaction mixture was extracted with dichloromethane (30 mL). The organic layer was separated and successively washed with aqueous hydrochloric acid (20 mL; 2N) and aqueous saturated sodium chloride (20 mL), dried over magnesium sulfate, filtered, and concentrated under reduced pressure. The crude residue was purified by a silica gel plug eluting with a 10% to 20% ethyl acetate in hexanes gradient to yield the title compound as a white solid (79 mg).

III. 3-(2'-Methylbiphenyl-3-ylsulfonamido)thiophene-2-carboxylic acid (83)

To a solution of 82 (78 mg; 0.20 mmol) in tetrahydrofuran (2 mL) were added aqueous sodium hydroxide (1 mL; 2N) and methanol (0.5 mL), sequentially. The reaction mixture was heated at 60° C. for 17 hours, allowed to cool to room temperature, and then extracted with aqueous sodium hydroxide (20 mL; 2N). The aqueous layer was washed with dichloromethane (20 mL), acidified with aqueous hydrochloric acid (20 mL; 6N), and extracted with dichloromethane (30 mL). The organic layer was washed with aqueous saturated sodium chloride (20 mL), dried over magnesium sulfate, filtered and the filtrate was concentrated under reduced pressure. The resulting white solid was purified by a silica gel plug eluting with a 25% to 100% ethyl acetate gradient to yield the title compound as a white solid (36 mg).

IV. 3-(2'-Methylbiphenyl-3-ylsulfonamido)thiophene-2-carboxylic acid, disodium salt (84)

To a partial solution of 83 (36 mg; 0.096 mmol) in acetonitrile (1.0 mL) was added aqueous sodium hydroxide (1.84 mL; 0.19 mmol; 0.1050N). The reaction mixture was frozen in a dry ice/acetone bath and lyophilized to yield the title compound as a white solid (26 mg).

Example 23

Preparation of 3-[(4-morpholin-4-yl)phenylsulfonamido]thiophene-2-carboxylic acid, disodium salt (87)

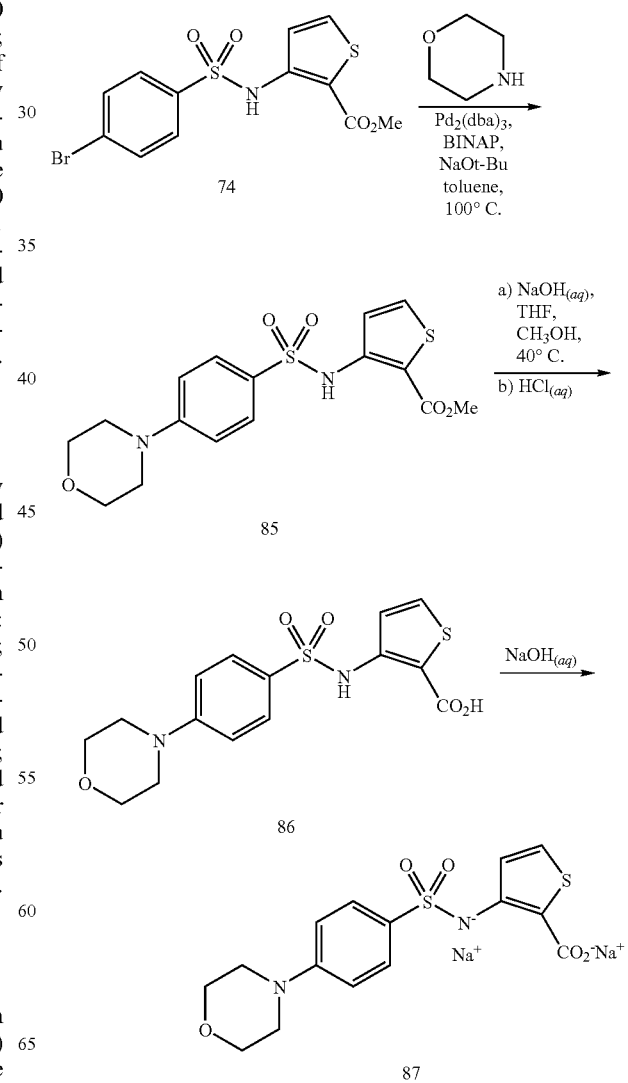

I. Methyl 3-(4-morpholinophenylsulfonamido) thiophene-2-carboxylate (85)

To a solution of 74 (1.02 g; 2.7 mmol) in anhydrous toluene (13.3 mL) were added morpholine (0.28 mL; 3.2 mmol), sodium tert-butoxide (0.52 g; 5.4 mmol), bis(dibenzylideneacetone)palladium(0) (79 mg; 0.1 mmol), and racemic-BINAP (104 mg; 0.2 mmol), sequentially. Additional toluene (13.3 mL) was added to aid in stirring. The reaction mixture was put under nitrogen atmosphere (flush×3) and then heated at 100° C. for 16 hours. After cooling to room temperature, the reaction mixture was extracted with dichloromethane (70 mL) and washed with aqueous hydrochloric acid (30 mL×2; 2N), water (30 mL), and aqueous saturated sodium chloride (30 mL). The dichloromethane extracts were dried over magnesium sulfate, filtered, and concentrated under reduced pressure to yield a yellow gel. The crude product was purified by silica gel chromatography (16% to 25% to 33% to 66% ethyl acetate in hexanes to 10% methanol in dichloromethane gradient) to yield the title compound as a pale yellow solid (307 mg).

II. 3-[(4-Morpholin-4-yl)phenylsulfonamido] thiophene-2-carboxylic acid (86)

To a solution of 85 (306 mg; 0.8 mmol) in tetrahydrofuran (2.7 mL) were added aqueous sodium hydroxide (5.3 mL; 2N) and methanol (5.3 mL) sequentially. The reaction mixture was heated at 40° C. for 17 hours, allowed to cool to room temperature, and then extracted with aqueous sodium hydroxide (20 mL; 2N). The aqueous layer was washed with diethyl ether (30 mL×2), acidified with aqueous hydrochloric acid (40 mL; 6N), and extracted with dichloromethane (40 mL). The organic layer was washed with aqueous saturated sodium chloride (20 mL), dried over magnesium sulfate, filtered and the filtrate was concentrated under reduced pressure. The resulting pale yellow solid was recrystallized from hot 80% ethyl acetate in hexane, to yield the title compound as a white solid (53 mg).

III. 3-[(4-Morpholin-4-yl)phenylsulfonamido] thiophene-2-carboxylic acid, disodium salt (87)

A solution of 86 (51 mg; 0.14 mmol) in aqueous sodium hydroxide (2.64 mL; 0.28 mmol; 0.1050N) was achieved by sonication for 1 minute. The reaction mixture was filtered, and the filtrate was frozen in a dry ice/acetone bath and lyophilized to yield the title compound as a white solid (61 mg).

Example 24

Preparation of 3-(4-tert-butylphenylsulfonamido) benzo[b]thiophene-2-carboxylic acid, disodium salt (90)

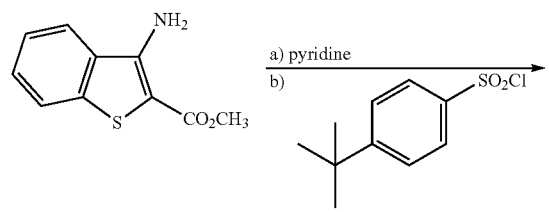

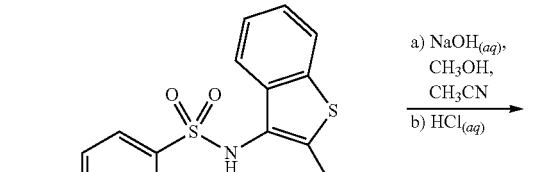

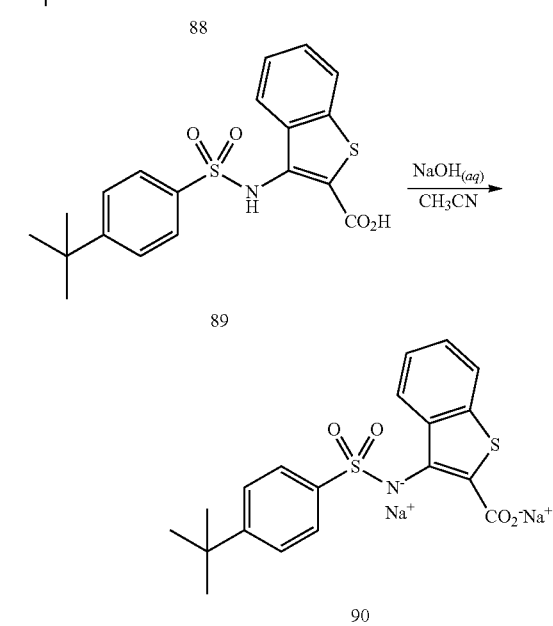

I. Methyl 3-(4-tert-butylphenylsulfonamido)benzo[b] thiophene-2-carboxylate (88)

To a solution methyl 3-aminobenzo[b]thiophene-2-carboxylate (0.207 g; 1 mmol) in pyridine (1 mL) was added 4-tert-butylbenzenesulfonyl chloride (0.256 g; 1.1 mmol). The resulting mixture was stirred at room temperature for 36 hours and then partitioned between dichloromethane and aqueous hydrochloric acid (2N). The organic layer was separated, dried over sodium sulfate, filtered through a pad of silica gel, and concentrated under reduced pressure to give the desired product as a yellow solid (120 mg).

II. 3-(4-tert-Butylphenylsulfonamido)benzo[b] thiophene-2-carboxylic acid (89)

To a solution of 88 (0.120 g; 0.31 mmol) in methanol (2 mL) was added aqueous sodium hydroxide (1 mL; 2 mmol; 2N). Acetonitrile (2 mL) was added to aid in solubility, and the resulting mixture was stirred overnight. The reaction mixture was acidified with aqueous hydrochloric acid (2N) and extracted with ethyl acetate. The organic layer was dried over sodium sulfate, decanted, and concentrated under reduced pressure. Trituration of the crude product from hexanes and dichloromethane yielded the desired product as a pink solid (121 mg).

III. 3-(4-tert-Butylphenylsulfonamido)benzo[b] thiophene-2-carboxylic acid, disodium salt (90)

To a solution of 89 (0.121 g; 0.30 mmol) in acetonitrile (2 mL), was added aqueous sodium hydroxide (5.8 mL; 0.61 mmol; 0.1050N). After stirring overnight at room temperature, the reaction mixture was frozen in a dry ice/acetone bath and lyophilized to give a white solid (0.121 g).

Example 25

Preparation of 3-(4-tert-butylphenylsulfonamido)-5-fluorobenzo[b]thiophene-2-carboxylic acid, disodium salt (93)

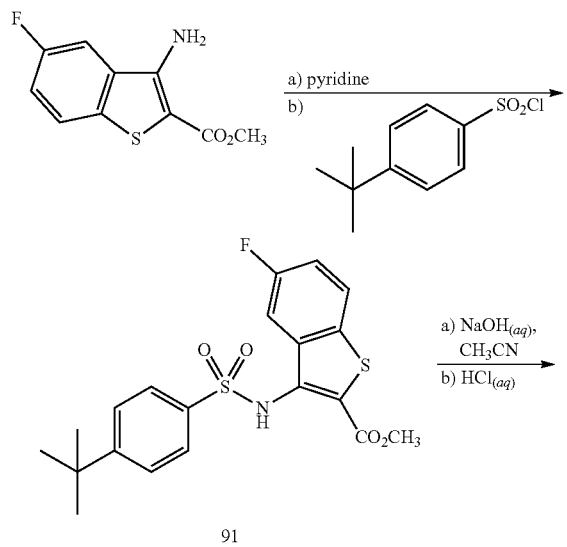

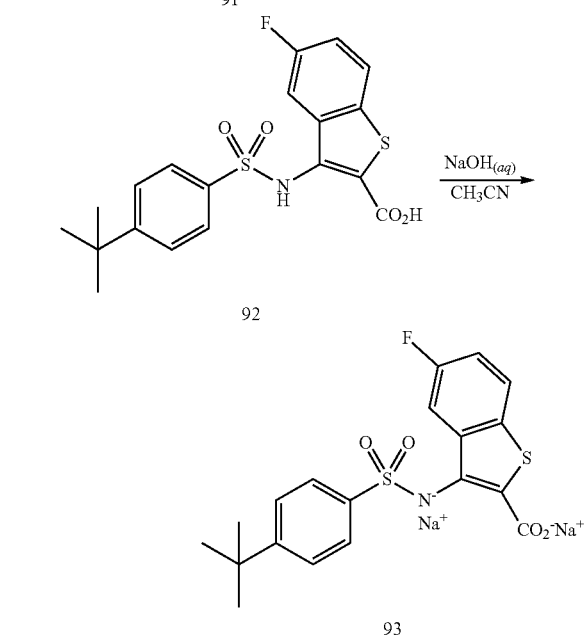

I. Methyl 3-(4-tert-butylphenylsulfonamido)-5-fluorobenzo[b]thiophene-2-carboxylate (91)

To a solution methyl 3-amino-4-fluorobenzo[b]thiophene-2-carboxylate (0.225 g; 1 mmol) in pyridine (1 mL) was added 4-tert-butylbenzenesulfonyl chloride (0.256 g; 1.1 mmol). The resulting mixture was stirred at room temperature for 36 hours and then partitioned between dichloromethane and aqueous hydrochloric acid (2N). The organic layer was separated, dried over sodium sulfate, decanted, and concentrated under reduced pressure. The residue obtained was purified by chromatography on silica gel (gradient from 0 to 35% ethyl acetate in hexanes) to give the desired product as a light yellow solid (176 mg).

II. 3-(4-tert-Butylphenylsulfonamido)-5-fluorobenzo[b]thiophene-2-carboxylic acid (92)

To a solution of 91 (176 mg; 0.42 mmol) in acetonitrile (2 mL) was added aqueous sodium hydroxide (0.83 mL; 2N). The resulting mixture was stirred overnight at room temperature. The reaction mixture was acidified with aqueous hydrochloric acid (2N) and extracted with ethyl acetate. The organic layer was dried over sodium sulfate, decanted, and concentrated under reduced pressure. The desired product was obtained as fine needles from dichloromethane and hexanes as a greenish-yellow solid (137 mg).

III. 3-(4-tert-Butylphenylsulfonamido)-5-fluorobenzo[b]thiophene-2-carboxylic acid, disodium salt (93)

To a solution of 92 (0.131 g; 0.33 mmol) in acetonitrile (3 mL), was added aqueous sodium hydroxide (6.4 mL; 0.67 mmol; 0.1050N). The reaction mixture was frozen in a dry ice/acetone bath and lyophilized to give a pale yellow solid (0.143 g).

Example 26

Preparation of 3-(4-tert-butylphenylsulfonamido)thieno[2,3-b]pyridine-2-carboxylic acid, disodium salt (96)

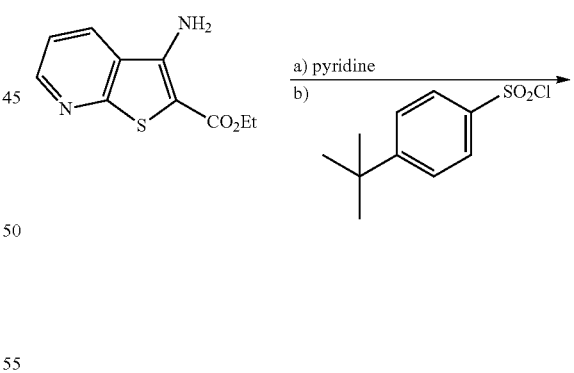

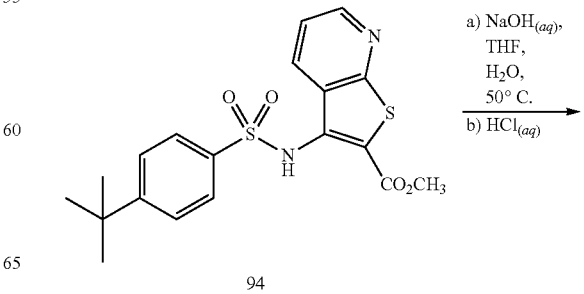

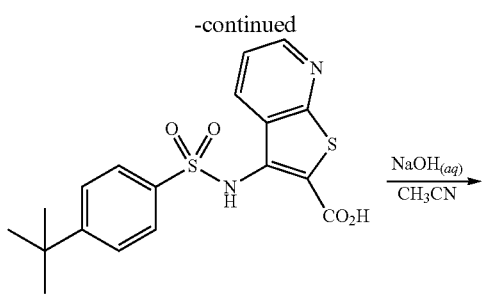

I. Methyl 3-(4-tert-butylphenylsulfonamido)thieno[2,3-b]pyridine-2-carboxylate (94)

To a solution of ethyl 3-aminothieno[2,3-b]pyridine-2-carboxylate (0.3 g; 1.35 mmol) in pyridine (10 mL) was added 4-tert-butylbenzenesulfonyl chloride (0.48 g; 2.03 mol). The reaction was stirred at room temperature for 18 hours and then diluted with water and extracted with ethyl acetate. The organic layer was separated and successively washed with aqueous hydrochloric acid (2N) and aqueous saturated sodium chloride solution, dried over magnesium sulfate, filtered, and evaporated under reduced pressure. The crude residue was purified by silica gel chromatography eluting with hexanes/ethyl acetate to yield the title compound as a white solid (0.070 g).

II. 3-(4-tert-Butylphenylsulfonamido)thieno[2,3-b]pyridine-2-carboxylic acid (95)

To a solution of 94 (0.070 g; 0.17 mmol) in tetrahydrofuran (2 mL), aqueous sodium hydroxide (2 mL; 4 mmol; 2N) and water (4 mL) were added. The reaction mixture was heated at 50° C. for 5 hours, cooled to room temperature, and then extracted with diethyl ether (2×). The ether solution was discarded. The aqueous layer was acidified with aqueous hydrochloric acid (2N) and extracted with ethyl acetate. The organic layer was separated and washed with aqueous saturated sodium chloride, dried over magnesium sulfate filtered, and evaporated under reduced pressure to yield the title compound as an off-white solid (0.067 g).

III. 3-(4-tert-Butylphenylsulfonamido)thieno[2,3-b]pyridine-2-carboxylic acid, disodium salt (96)

To a solution of 95 (0.067 g; 0.17 mmol) in acetonitrile (2 mL), aqueous sodium hydroxide (3.4 mL; 0.34 mmol; 0.1050N) and water (3 mL) were added. The reaction mixture was frozen in a dry ice/acetone bath and lyophilized to yield the title compound as a light yellow solid (0.076 g).

Example 27

Preparation of 3-[2-bromo-4-(trifluoromethyl)phenylsulfonamido]thiophene-2-carboxylic acid, disodium salt (99)

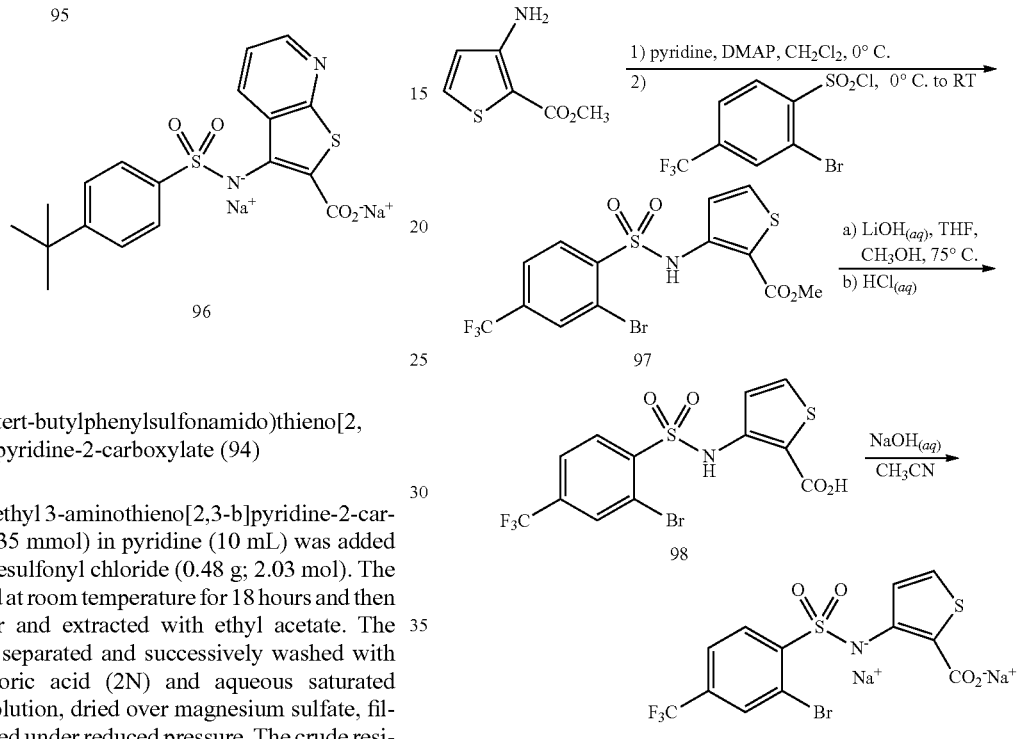

I. Methyl 3-[2-bromo-4-(trifluoromethyl)phenylsulfonamido]thiophene-2-carboxylate (97)

To a cooled (0° C.) solution of methyl 3-aminothiophene-2-carboxylate (534.0 mg; 3.4 mmol), 4-dimethylaminopyridine (94.3 mg; 0.77 mmol) and pyridine (2.5 mL; 30.9 mmol) in anhydrous dichloromethane (60 mL) was added 2-bromo-4-(trifluoromethyl)benzene-1-sulfonyl chloride (1.0 g; 3.09 mmol) portion-wise. After addition was complete the reaction mixture was stirred at 0° C. for 20 minutes, gradually allowed to war to room temperature, stirred for 16 hours, and then washed with aqueous hydrochloric acid (50 mL; 2N). The organic phase was dried over magnesium sulfate, filtered, and concentrated under reduced pressure. The crude residue was purified by automated silica gel column chromatography (Biotage®) eluting with ethyl acetate/hexanes (0 to 30% v/v over 400 mL gradient elution) to give the title product as a white solid (330 mg).

II. 3-[2-Bromo-4-(trifluoromethyl)phenylsulfonamido]thiophene-2-carboxylic acid (98)

To a solution of 97 (330.0 mg; 0.74 mmol) in tetrahydrofuran (8 mL) and methanol (2 mL) was added aqueous lithium hydroxide (4 mL; 2M). The reaction mixture was heated at 75-80° C. for 6 hours, allowed to cool to room temperature and then concentrated under reduced pressure. The resulting residue was dissolved in chloroform (15 mL) and washed with aqueous hydrochloric acid (2×10 mL; 2N). The organic phase was dried over magnesium sulfate, filtered, and concentrated under reduced pressure. The crude residue was purified by preparative HPLC to afford the title compound as a white solid (110 mg).

III. 3-[2-Bromo-4-(trifluoromethyl)phenylsulfonamido]thiophene-2-carboxylic acid, disodium salt (99)

To a solution of 98 (110.0 mg; 0.25 mmol) in acetonitrile (5 mL) was added aqueous sodium hydroxide (5.1 mL; 0.51 mmol; 0.1M). The reaction mixture was frozen in a dry ice/acetone bath and lyophilized to yield the title compound as a white solid (85.5 mg).

Example 28

Preparation of 3-(4-tert-butyl-2-phenoxyphenylsulfonamido)thiophene-2-carboxylic acid, disodium salt (105)

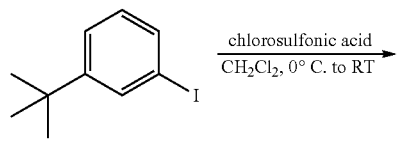

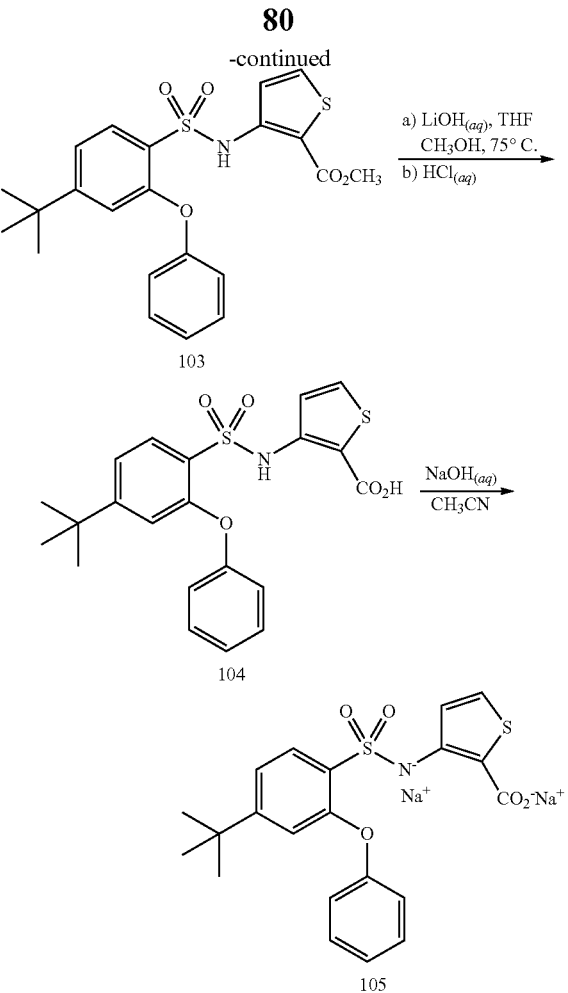

I. 4-tert-Butyl-2-iodobenzenesulfonic acid (100)

Synthesized as described for 1 using 1-tert-butyl-3-iodobenzene (9.65 g; 37.09 mmol), chlorosulfonic acid (3.20 mL; 48.22 mmol), and anhydrous dichloromethane (140 mL). Trituration of the crude product from hexanes yielded the title compound as a brown oil (12.0 g).

II. 4-tert-Butyl-2-iodobenzene-1-sulfonyl chloride (101)

To a suspension of 100 (12.0 g; 35.0 mmol) in dichloroethane (300 mL) at 50° C. was added phosphorus pentachloride (11.01 g; 52.9 mmol). After addition was complete, the reaction mixture was heated at 75-80° C. overnight, cooled to 50° C., and additional phosphorus pentachloride (6.0 g; 28.8 mmol) was added. After heating at 85° C. for an additional 12 hours, the reaction mixture was again cooled to 50° C. and additional phosphorus pentachloride (2.0 g; 9.60 mmol) was added. Heating was continued at 90° C. for 4 hours, cooled to room temperature, and concentrated under reduced pressure. The resulting crude oil was purified by automated silica gel column chromatography (Biotage®) eluting with ethyl acetate/hexanes (0 to 20% v/v over 400 mL gradient elution) to give the title compound as a yellow oil (9.98 g).

III. Methyl 3-(4-tert-butyl-2-iodophenylsulfonamido)thiophene-2-carboxylate (102)

Synthesized as described for 3 using methyl 3-aminothiophene-2-carboxylate (723.0 mg; 4.60 mmol), 4-dimethylaminopyridine (127.6 mg; 1.05 mmol), pyridine (3.38 mL; 41.8 mmol) and 101 (1.50 g; 4.18 mmol). The crude pink residue was triturated from diisopropyl ether to yield the title product as light pink solid (1.50 g).

IV. Methyl 3-(4-tert-butyl-2-phenoxyphenylsulfonamido)thiophene-2-carboxylate (103)

A mixture of 102 (800 mg; 1.66 mmol), phenol (103 mg; 1.09 mmol), salicylaldoxime (45.5 mg; 0.33 mmol), copper (I) oxide (11.8 mg; 0.083 mmol), cesium carbonate (811.3 mg; 2.49 mmol), powdered molecular sieves (300 mg; 3A°) and anhydrous acetonitrile (15 mL) was heated at 85° C. for 16 hours. The reaction mixture was allowed to cool to room temperature and then was diluted with ethyl acetate (20 mL), filtered through a pad of celite and concentrated under reduced pressure. The resulting green residue was purified by automated silica gel chromatography (Biotage®) eluting with ethyl acetate/hexanes (0 to 15% v/v over 600 mL gradient elution) to yield the title compound as a white solid (201 mg).

V. 3-(4-tert-Butyl-2-phenoxyphenylsulfonamido)thiophene-2-carboxylic acid (104)

Synthesized as described for 23 using 103 (205.0 mg; 0.46 mmol), aqueous lithium hydroxide (2.3 mL; 4.6 mmol; 2M), tetrahydrofuran (10 mL) and methanol (2 mL). This yielded a beige solid which was recrystallized from hexanes/dichloromethane to afford the title compound as a white solid (86.0 mg).

VI. 3-(4-tert-Butyl-2-phenoxyphenylsulfonamido)thiophene-2-carboxylic acid, disodium salt (105)

Synthesized as described for 5 using 104 (86.0 mg; 0.20 mmol), aqueous sodium hydroxide (3.99 mL; 0.40 mmol; 0.1M) and acetonitrile (7 mL). This afforded the title compound as a white solid (77.9 mg).

Example 29

Preparation of 3-(4-tert-butyl-2-fluorophenylsulfonamido)thiophene-2-carboxylic acid, disodium salt (111)

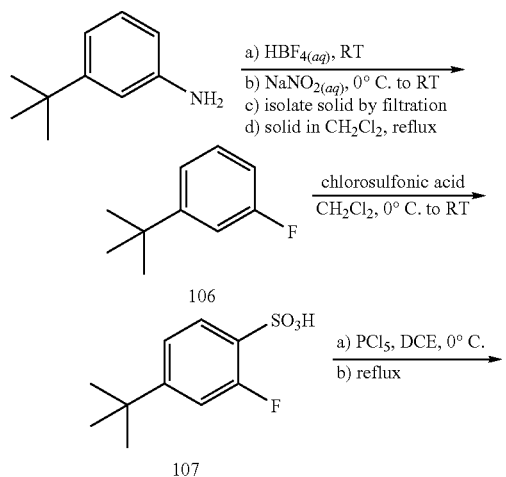

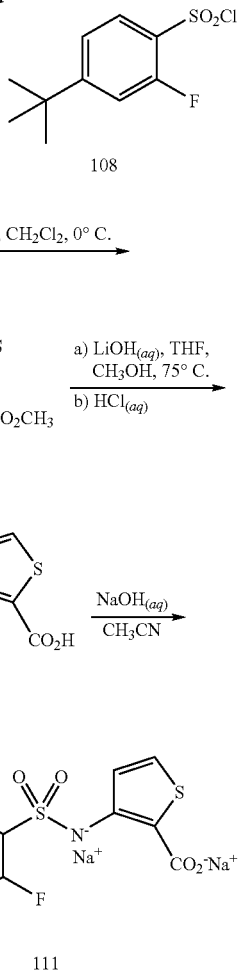

I. 1-tert-Butyl-3-fluorobenzene (106)

To a vigorously stirred solution of tetrafluoroboric acid (73.26 mL; 0.4 mol; 48% wt % solution in water) in a large beaker at room temperature was slowly added 3-tert-butylaniline (15.0 g; 0.10 mmol). The resulting mixture was stirred at room temperature for 30 minutes, cooled to 0° C. and then a solution of sodium nitrite (11.09 g; 0.16 mol) in water (30 mL) was added. After addition was complete reaction mixture was stirred at 0° C. for 30 minutes, warmed to room temperature and further stirred for 20 minutes. The resulting beige slushy material was filtered, washed with tetrafluoroboric acid (20 mL) and ether (3×20 mL) to yield an off-white solid (13.54 g). The latter was dissolved in dichloromethane (300 mL) and heated at reflux for 2 hours until the solid was dissolved and no more gas (HF) evolution was observed. The reaction mixture was cooled to room temperature and concentrated under reduced pressure to yield a dark oil that was purified by column chromatography eluting with ethyl acetate/hexanes (0 to 5% v/v gradient elution over 1 L) to yield the title compound as a pale yellow liquid (11.80 g).

II. 4-tert-Butyl-2-fluorobenzenesulfonic acid (107)

Synthesized as described for 1 using 106 (830.0 mg; 5.45 mmol), chlorosulfonic acid (0.44 mL; 6.54 mmol) and anhydrous dichloromethane (25 mL). The crude gray solid obtained was washed with hexanes and dried under reduced pressure. This afforded a 3:1 regioisomeric mixture of the title compound and 2-tert-butyl-4-fluorobenzenesulfonic acid (960 mg).

III. 4-tert-Butyl-2-fluorobenzene-1-sulfonyl chloride (108)

Synthesized as described for 2 using a 3:1 regioisomeric mixture of 107 (23.68 g; 0.10 mol) and 2-tert-butyl-4-fluorobenzenesulfonic acid, phosphorus pentachloride (23.13 g; 0.11 mol) and dichloroethane (700 mL). The title compound was obtained as a white solid which was a 1:1 regioisomeric ratio of itself and 2-tert-butyl-4-fluorobenzene-1-sulfonyl chloride (10.0 g).

IV. Methyl 3-(4-tert-butyl-2-fluorophenylsulfonamido)thiophene-2-carboxylate (109)

Synthesized as described for 3 using a regioisomeric mixture of 108 (2.53 g; 10.09 mmol) and 2-tert-butyl-4-fluorobenzene-1-sulfonyl chloride, methyl 3-aminothiophene-2-carboxylate (1.44 g; 9.17 mmol), 4-dimethylaminopyridine (280.0 mg; 2.29 mmol), pyridine (15.0 mL; 183 mmol) and anhydrous dichloromethane (50 mL). Purification of the crude residue afforded a regioisomeric mixture of 109 and methyl 3-(2-tert-butyl-4-fluorophenylsulfonamido)thiophene-2-carboxylate (1:1 ratio by HPLC). Separation of the regioisomers was achieved by preparative HPLC to give the title compound as a white solid (122 mg).

V. 3-(4-tert-Butyl-2-fluorophenylsulfonamido)thiophene-2-carboxylic acid (110)

Synthesized as described for 23 using 109 (122.0 mg; 0.33 mmol), aqueous lithium hydroxide (1.64 mL; 3.28 mmol; 2M), tetrahydrofuran (10 mL) and methanol (2 mL). This afforded the title compound as a white solid (115 mg).

VI. 3-(4-tert-Butyl-2-fluorophenylsulfonamido)thiophene-2-carboxylic acid, disodium salt (111)

Synthesized as described for 5 using 110 (115.0 mg; 0.32 mmol), aqueous sodium hydroxide (6.4 mL; 0.64 mmol; 0.1M) and acetonitrile (7 mL). This afforded the title compound as a white solid (110 mg).

Example 30

Preparation of 3-[4-tert-butyl-2-(2-carboxyvinyl)phenylsulfonamido]thiophene-2-carboxylic acid, trisodium salt (115)

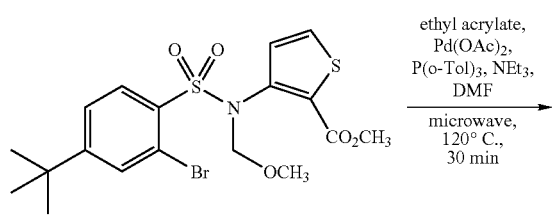

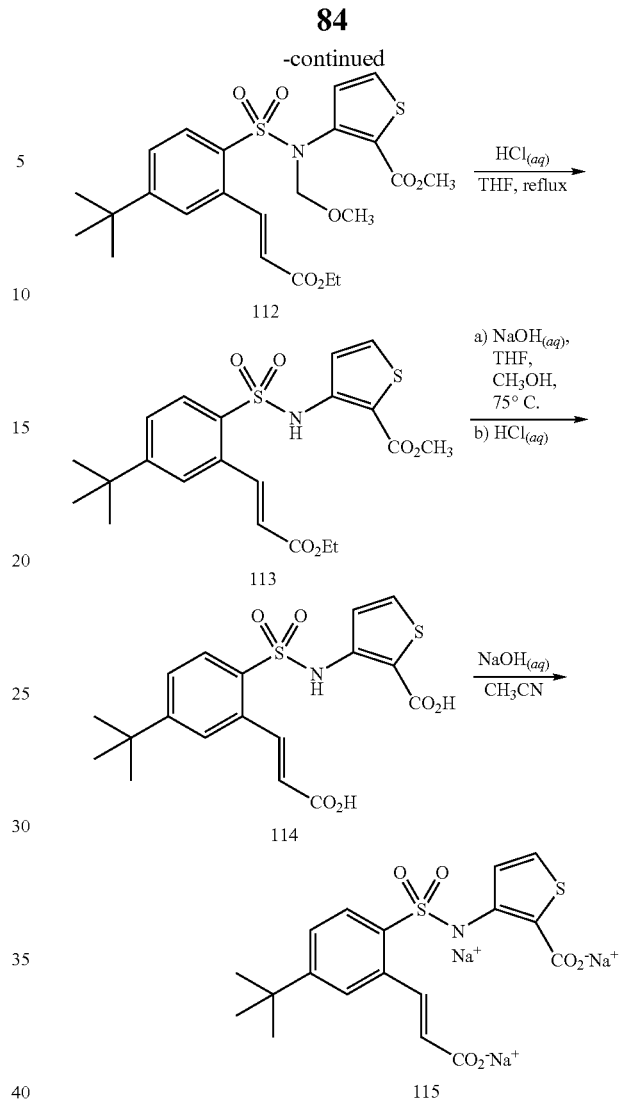

I. Methyl 3-[4-tert-butyl-2-(3-ethoxy-3-oxoprop-1-enyl)-N-(methoxymethyl)phenyl-sulfonamido]thiophene-2-carboxylate (112)

A 10.0 mL microwave reaction vial was charged with 6 (100.0 mg; 0.21 mmol), palladium(II) acetate (2.2 mg; 0.011 mmol) and tri(o-tolyl)phosphine (13.0 mg; 0.042 mmol). The reaction vial was then flushed with nitrogen and subsequently charged with NV-dimethylformamide (0.4 mL), triethylamine (0.04 mL; 0.26 mmol) and ethyl acrylate (0.03 mL; 0.262 mmol). The reaction vial was sealed and heated for 30 minutes at 120° C. under microwave conditions. The reaction mixture was allowed to cool to room temperature and then was diluted with dichloromethane (10.0 mL) and washed with water. The aqueous layer was separated and extracted with dichloromethane (2×10 mL). The organic layers were combined, dried over magnesium sulfate, filtered, and concentrated under reduced pressure. The resulting yellow oil residue was purified by automated silica gel column chromatography (Biotage®) eluting with ethyl acetate/hexanes (0 to 30% v/v gradient elution over 800 mL and then 30% to 100% v/v gradient elution over 200 mL) to afford the title compound as a clear oil (48.6 mg).

II. Methyl 3-[4-tert-butyl-2-(3-ethoxy-3-oxoprop-1-enyl)phenylsulfonamido]thiophene-2-carboxylate (113)

Synthesized as described for 22 using 112 (151.0 mg; 0.30 mmol), aqueous hydrochloric acid (5.0 mL; 2N) and tetrahydrofuran (5.0 mL). After heating reaction at reflux for 16 hours additional aqueous hydrochloric acid (3 mL; 6N) and tetrahydrofuran (3 mL) were added and heated for an additional 4 hours. The resulting clear oil was purified by automated silica gel chromatography (Biotage®) eluting with ethyl acetate/hexanes (0 to 20% v/v over 700 mL gradient elution followed by 20% to 100% v/v over 200 mL gradient elution) to yield the title compound as a clear oil (78.5 mg).

III. 3-[4-tert-Butyl-2-(2-carboxyvinyl)phenylsulfonamido]thiophene-2-carboxylic acid (114)

Synthesized as described for 27 using 113 (73.0 mg; 0.16 mmol), aqueous sodium hydroxide (5.0 mL; 2M), tetrahydrofuran (5 mL) and methanol (1 mL). This afforded the title compound as an off-white solid (67.0 mg).

IV. 3-[4-tert-Butyl-2-(2-carboxyvinyl)phenylsulfonamido]thiophene-2-carboxylic acid, trisodium salt (15)

Synthesized as described for 5 using 114 (59.0 mg; 0.14 mmol), aqueous sodium hydroxide (4.20 mL; 0.42 mmol; 0.1M) and acetonitrile (0.5 mL). This afforded the title compound as an off-white solid (82.5 mg).

Example 31

Preparation of 3-[4-(1H-pyrazol-1-yl)phenylsulfonamido]thiophene-2-carboxylic acid, disodium salt (118)

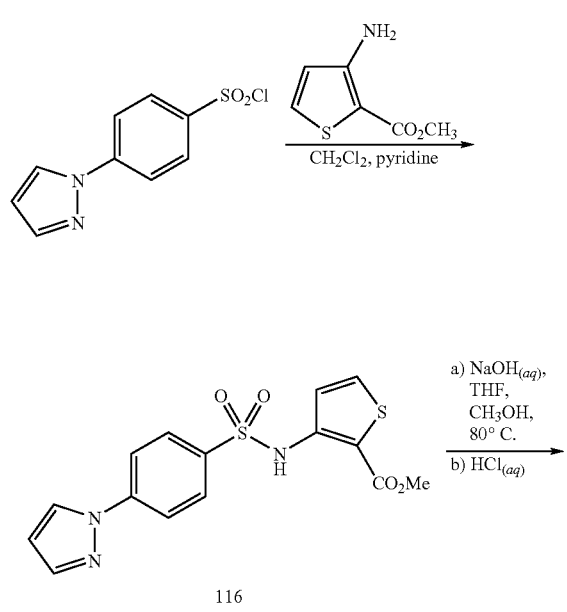

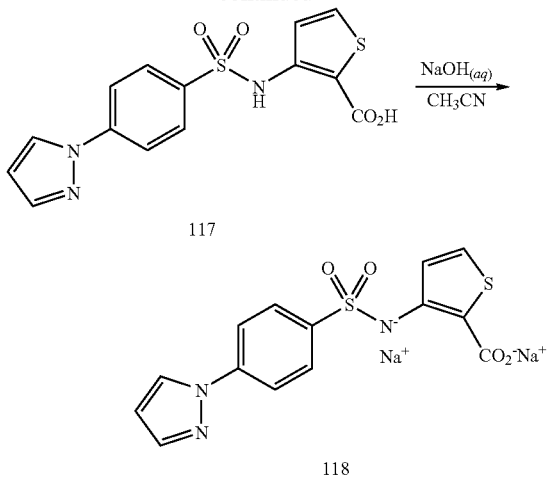

I. Methyl 3-[4-(1H-pyrazol-1-yl)phenylsulfonamido]thiophene-2-carboxylate (116)

To a solution of 4-(1H-pyrazol-1-yl)benzene-1-sulfonyl chloride (0.5 g; 2.0 mmol) in dichloromethane (4.5 mL) at room temperature, was added methyl 3-aminothiophene-2-carboxylate (0.27 g; 1.7 mmol) followed by pyridine (0.27 g; 3.4 mmol) and then stirred at room temperature under a nitrogen atmosphere for 24 hours. The reaction mixture was concentrated under reduced pressure and then taken up in ethyl acetate (50 mL) and washed with water. The aqueous layer separated and extracted with ethyl acetate (2×50 mL). The combined organic phases were successively washed with water and aqueous saturated sodium chloride, dried over magnesium sulfate, filtered and concentrated under reduced pressure. The crude residue was recrystallized from ethyl acetate/hexanes (1:9, v/v) to yield the title product as a tan/yellow solid (404 mg).

II. 3-[4-(1H-Pyrazol-1-yl)phenylsulfonamido]thiophene-2-carboxylic acid (117)

To a solution of 116 (0.40 g; 1.1 mmol) in tetrahydrofuran (20 mL) and methanol (7 mL) was added aqueous sodium hydroxide (20 mL; 2N) and then heated at 80° C. for 24 hours. The reaction mixture was allowed to cool to room temperature and then extracted with diethyl ether (20 mL). The aqueous layer was separated and acidified with aqueous hydrochloric acid (15 mL; 2N) then extracted with ethyl acetate (2×20 mL). The combined organic phases were dried over magnesium sulfate, filtered, and concentrated under reduced pressure to yield the title product as an off-white solid (0.34 g).

III. 3-[4-(1H-Pyrazol-1-yl)phenylsulfonamido]thiophene-2-carboxylic acid, disodium salt (118)

To a solution of 117 (0.22 g; 0.63 mmol) in acetonitrile (2 mL) was added aqueous sodium hydroxide (12.6 mL; 1.26 mmol; 0.1N and water (20 mL). The reaction mixture was frozen in a dry ice/acetone bath and lyophilized to yield the title compound as a tan solid (0.23 g).

Example 32

Preparation of 3-(3-methyl-4-(pyrrolidin-1-yl)phenylsulfonamido)thiophene-2-carboxylic acid, disodium salt (124)

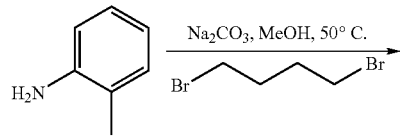

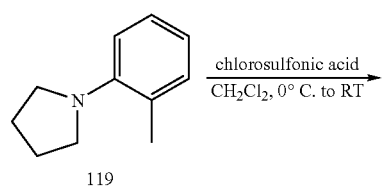

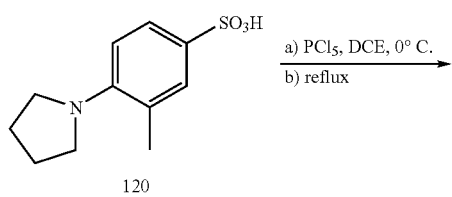

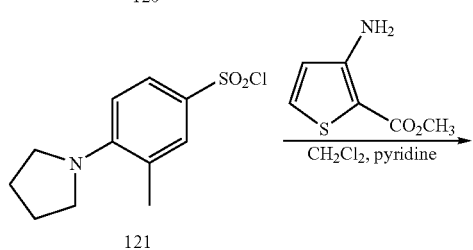

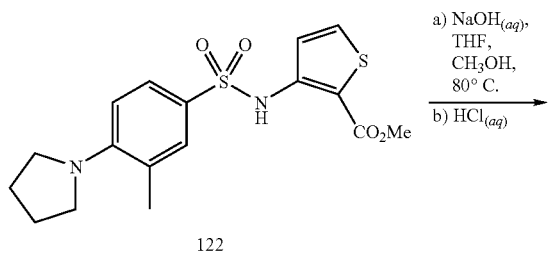

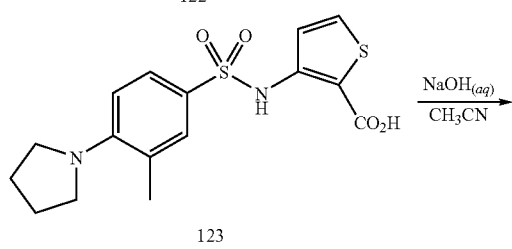

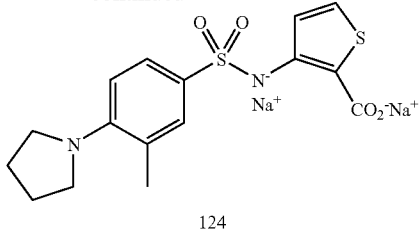

I. 1-o-Tolyl-pyrrolidine (119)

To a solution of o-toluidine (2.0 g; 18.7 mmol) in methanol (62 mL) was added sodium carbonate (4.95 g; 46.75 mmol) followed by 1,4-dibromobutane (4.85 g; 22.4 mmol). The resulting mixture was stirred at 50° C. under a nitrogen atmosphere overnight and then diluted with water and extracted with ethyl acetate. The organic layer was dried over magnesium sulfate, filtered, and concentrated under reduced pressure. The crude residue was purified by automated silica gel column chromatography (Biotage®) eluting with ethyl acetate/hexanes (0 to 40% v/v over 900 mL gradient elution) to yield the title product as a dark yellow-orange oil (1.24 g).

II. 3-Methyl-4-(pyrrolidin-1-yl)benzenesulfonic acid((20)

To a cooled (0° C.) solution of 119 (1.24 g; 7.7 mmol) in anhydrous dichloromethane (38 mL) was added chlorosulfonic acid (0.61 mL; 9.24 mmol) dropwise (1 mL/minutes). The reaction mixture w as allowed to gradually warm to room temperature while stirring overnight. The reaction mixture was concentrated under reduced pressure. The resulting oil w as taken up in diisopropyl ether (10 mL) and aqueous hydrochloric acid (0.5 mL; 2N) then stirred vigorously at room temperature for 2 hours. The organic phase was separated and concentrated under reduced pressure to yield the desired compound as an amber oil (1.8 g).

III. 3-Methyl-4-(pyrrolidin-1-yl)benzene-1-sulfonyl chloride (121)

To cooled (0° C.) solution of 120 (1.8 g; 7.7 mmol) in dichloroethane (15.3 mL) was added 1 equivalent of phosphorus pentachloride (total amount: 3.2 g; 15.4 mmol) slowly and portion-wise. The reaction mixture was heated at reflux for 2 hours, and then an additional equivalent of phosphorus pentachloride was added. After addition was complete, the reaction was heated at reflux for 48 hours. Additional phosphorus pentachloride (1.6 g; 7.7 mmol) was added, and heating was continued at reflux overnight, cooled to room temperature, and then concentrated under reduced pressure. The crude residue was taken up in ethyl acetate/hexanes (1:1, v/v) and passed through a plug of silica gel eluting with ethyl acetate/hexanes (1:1, v/v). The organic phase was concentrated under reduced pressure then taken up in ethyl acetate (50 mL) and washed with water (5 mL). The aqueous phase was extracted with ethyl acetate (2×50 mL), dried over magnesium sulfate, filtered, and concentrated under reduced pressure to yield the title product as a dark oil (1.5 g).

IV. Methyl 3-(3-methyl-4-(pyrrolidin-1-yl)phenylsulfonamido)thiophene-2-carboxylate (122)

To a solution of 121(1.5 g; 5.5 mmol) in dichloromethane (14 mL) at room temperature, methyl 3-aminothiophene-2- carboxylate (0.86 g; 5.5 mmol) was added followed by pyridine (0.87 g; 11.0 mmol) and then stirred at room temperature under a nitrogen atmosphere for 24 hours. The reaction mixture was concentrated under reduced pressure and then taken up in ethyl acetate (20 mL) and extracted with water. The aqueous layer was separated and extracted with ethyl acetate (2×20 mL). The combined organic phases were successively washed with water and aqueous saturated sodium chloride, dried over magnesium sulfate, filtered and concentrated under reduced pressure. The resulting crude residue was purified by automated silica gel column chromatography (Biotage®) eluting with ethyl acetate/hexanes (0 to 40% v/v over 900 mL gradient elution) to give the title product as a light red solid (86 mg).

V. 3-(3-Methyl-4-(pyrrolidin-1-yl)phenylsulfonamido)thiophene-2-carboxylic acid (123)

To a solution of 122 (85.0 mg; 0.22 mmol) in tetrahydrofuran (5 mL) and methanol (5 mL) was added aqueous sodium hydroxide (7.5 mL; 2N) and then heated at 80° C. for 16 hours. The reaction mixture was allowed to cool to room temperature and then extracted with diethyl ether. The aqueous layer was separated and acidified with aqueous hydrochloric acid (15 mL; 2N) then extracted with ethyl acetate (2×15 mL). The combined organic phases were dried over magnesium sulfate, filtered, and concentrated under reduced pressure. The resulting crude residue was purified by automated silica gel column chromatography (Biotage®) eluting with dichloromethane/methanol to give the title product as an off-white solid (47 mg).

VI. 3-(3-Methyl-4-(pyrrolidin-1-yl)phenylsulfonamido)thiophene-2-carboxylic acid, disodium salt (124)

To a solution of 123 (46.0 mg; 0.13 mmol) in acetonitrile (2.0 mL), aqueous sodium hydroxide (2.6 mL; 0.26 mmol; 0.1N) and water (10 mL) were added. The reaction mixture was frozen in a dry ice/acetone bath and lyophilized to yield the title compound as a tan solid (53 mg).

Example 33

Preparation of 3-(2,3-dihydro-1H-indene-5-sulfonamido)thiophene-2-carboxylic acid, disodium salt (127)

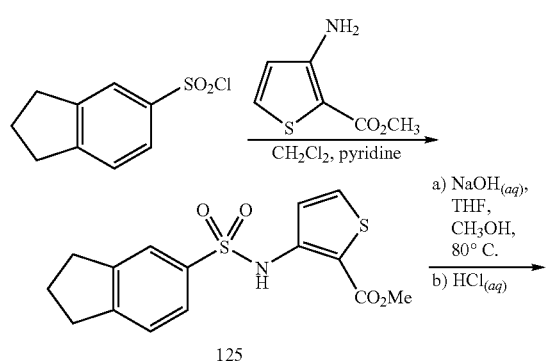

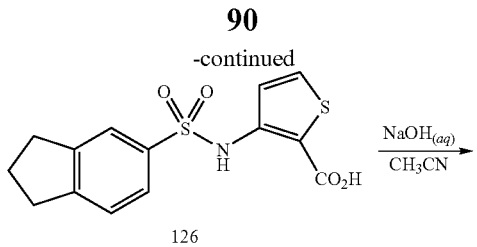

126

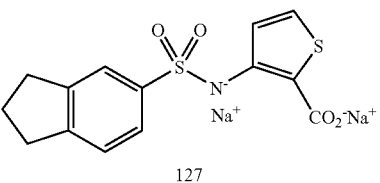

127

I. Methyl 3-(2,3-dihydro-1H-indene-5-sulfonamido)thiophene-2-carboxylate (125)

To a solution of 2,3-dihydro-1H-indene-5-sulfonyl chloride (0.5 g; 2.3 mmol) in dichloromethane (5 mL) at room temperature, methyl 3-aminothiophene-2-carboxylate (0.3 g; 1.9 mmol) was added followed by pyridine (0.32 g; 4.0 mmol) and then stirred at room temperature under a nitrogen atmosphere for 24 hours. The reaction mixture was concentrated under reduced pressure and then taken up in ethyl acetate (50 mL) and extracted with water. The aqueous layer separated and extracted with ethyl acetate (2×50 mL). The combined organic phases were successively washed with water and aqueous saturated sodium chloride, dried over magnesium sulfate, filtered and concentrated under reduced pressure. The resulting crude residue was recrystallized from acetonitrile to yield the title product as a white solid (0.3 g).

II. 3-(2,3-Dihydro-1H-indene-5-sulfonamido)thiophene-2-carboxylic acid (126)

To a solution of 125 (0.30 g; 0.89 mmol) in tetrahydrofuran (20 mL) and methanol (7 mL) was added aqueous sodium hydroxide (20 mL; 2N) and then heated at 80° C. for 16 hours. The reaction mixture was allowed to cool to room temperature and then extracted with diethyl ether (20 mL). The aqueous layer was separated and acidified with aqueous hydrochloric acid (15 mL; 2N) then extracted with ethyl acetate (2×20 mL). The combined organic phases were dried over magnesium sulfate, filtered, and concentrated under reduced pressure to yield the title product as an off-white solid (0.29 g).

III. 3-(2,3-Dihydro-1H-indene-5-sulfonamido)thiophene-2-carboxylic acid, disodium salt (127)

To a solution of 126 (0.19 g; 0.59 mmol) in acetonitrile (2 mL), aqueous sodium hydroxide (11.7 mL; 1.17 mmol; 0.1N) and water (20 mL) were added. The reaction mixture was frozen in a dry ice/acetone bath and lyophilized to yield the title compound as a tan solid (0.2 g).

Example 34

Preparation of 3-(4-cyclohexylphenylsulfonamido) thiophene-2-carboxylic acid, disodium salt (130)

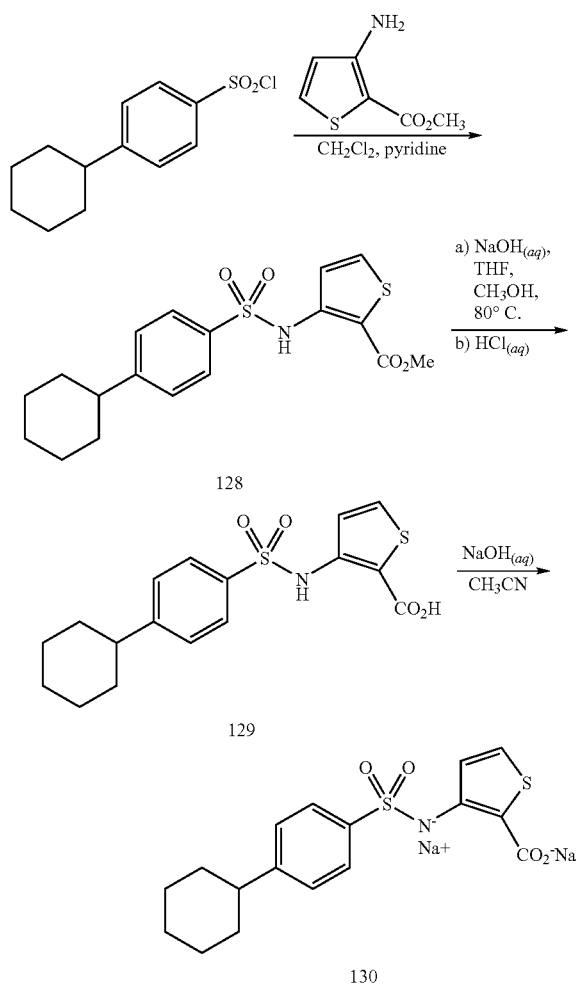

I. Methyl 3-(4-cyclohexylphenylsulfonamido) thiophene-2-carboxylate (128)

To a solution of 4-cyclohexylbenzene-1-sulfonyl chloride (0.45 g; 1.74 mmol) in dichloromethane (4.0 mL) at room temperature, methyl 3-aminothiophene-2-carboxylate (0.25 g; 1.6 mmol) was added followed by pyridine (0.25 g; 3.2 mmol) and then stirred at room temperature under a nitrogen atmosphere for 24 hours. The reaction mixture was concentrated under reduced pressure and then taken up in ethyl acetate (50 mL) and extracted with water. The aqueous layer separated and extracted with ethyl acetate (2×50 mL). The combined organic phases were successively washed with water and aqueous saturated sodium chloride, dried over magnesium sulfate, filtered and concentrated under reduced pressure. The resulting crude residue was purified by automated silica gel column chromatography (Biotage®) eluting with ethyl acetate/hexanes (0 to 40% v/v over 900 mL gradient elution) to give the title product as an off-white solid (0.55 g).

II. 3-(4-Cyclohexylphenylsulfonamido)thiophene-2-carboxylic acid (129)

To a solution of 128 (0.55 g; 1.46 mmol) in tetrahydrofuran (20 mL) and methanol (7 mL) was added aqueous sodium hydroxide (20 mL; 2N) and then heated at 80° C. for 16 hours. The reaction mixture was allowed to cool to room temperature and then extracted with diethyl ether (20 mL). The aqueous layer was separated and acidified with aqueous hydrochloric acid (15 mL; 2N) then extracted with ethyl acetate (2×20 mL). The combined organic phases were dried over magnesium sulfate, filtered, and concentrated under reduced pressure to yield the title product as a gray solid (0.39 g).

III. 3-(4-Cyclohexylphenylsulfonamido)thiophene-2-carboxylic acid, disodium salt (130)

To a solution of 129 (0.39 g; 1.1 mmol) in acetonitrile (2.0 mL), aqueous sodium hydroxide (21.4 mL; 2.14 mmol; 0.1N) and water (20 mL) were added. The reaction mixture was frozen in a dry ice/acetone bath and lyophilized to yield the title compound as a tan solid (0.44 g).

Example 35

Preparation of 3-(2-cyclopentyl-4-fluorophenylsulfonamido)thiophene-2-carboxylic acid, disodium salt (138)

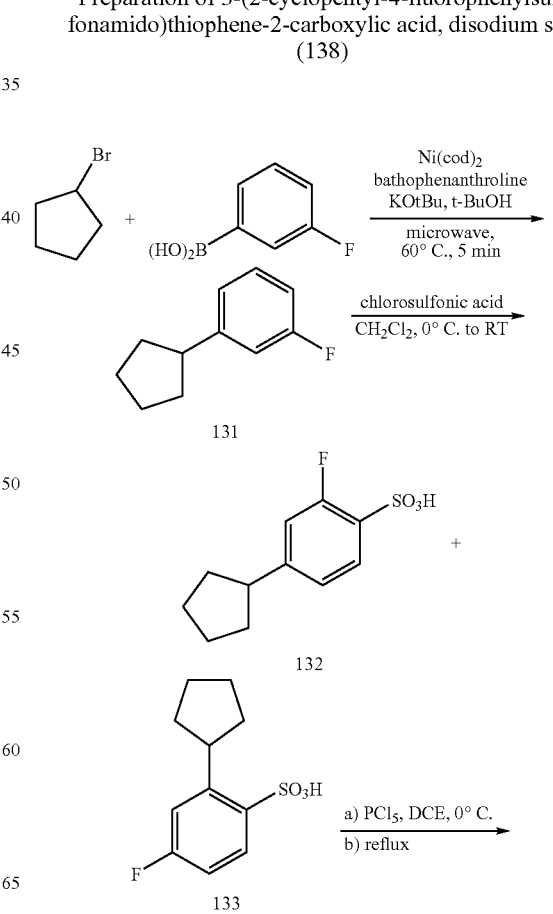

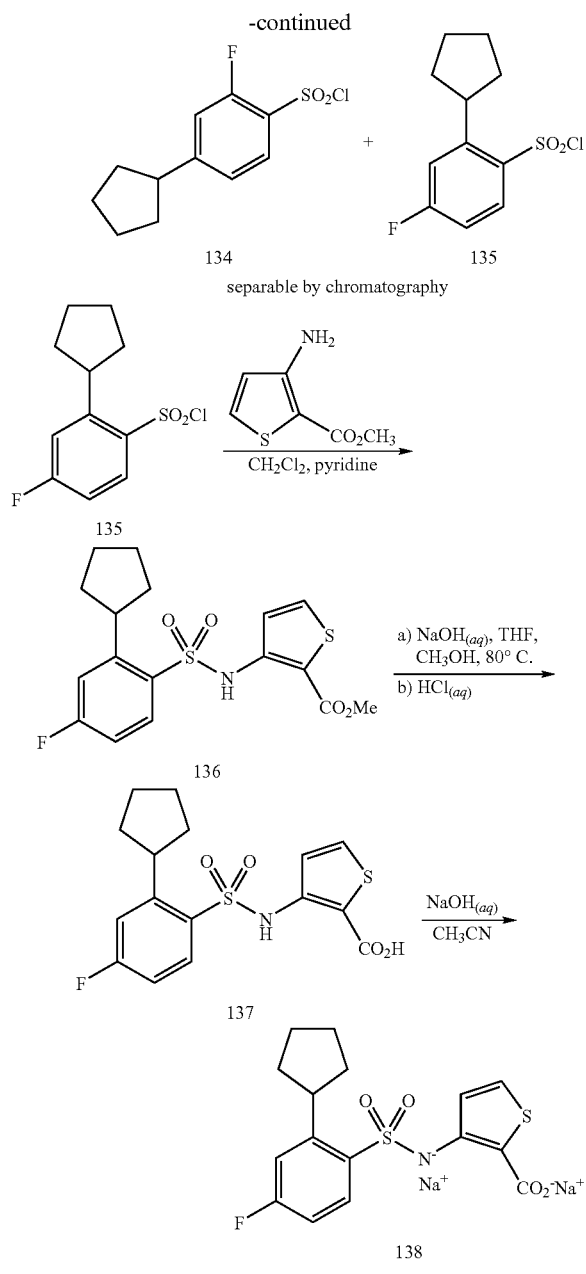

I. 1-Cyclopentyl-3-fluorobenzene (131)

3-fluorophenylboronic acid (0.5 g; 3.6 mmol), bromocyclopentane (0.41 g; 2.7 mmol), potassium tert-butoxide (0.49 g; 4.3 mmol), bathophenanthroline (72 mg; 0.22 mmol), bis(1,5-cyclooctadiene)nickel(0) (30 mg; 0.11 mmol) and t-butanol (9 mL) were added sequentially to a 10-20 mL microwave reactor tube containing a stir bar. The vessel was capped, placed under nitrogen, and then subjected to the following microwave conditions: Temperature=160° C.; Time=5 minutes; Power=250 W; Cooling turned on; Absorption=High; prestir=5 s; FHT turned off. The crude reaction mixture was allowed to cool to room temperature and then acidified by the addition of aqueous hydrochloric acid (15 mL; 1N) and extracted with ethyl acetate (3×20 mL). The combined organic phases were successively washed with aqueous saturated sodium bicarbonate, aqueous saturated sodium chloride, dried over magnesium sulfate, filtered, and concentrated under reduced pressure. The resulting crude residue was purified by automated silica gel column chromatography (Biotage®) eluting with ethyl acetate/hexanes to give the title product as a light red solid (0.2 g).

II. 4-Cyclopentyl-2-fluorobenzenesulfonic acid (132) and 2-cyclopentyl-4-fluorobenzenesulfonic acid (133)

To a cooled (0° C.) solution of 131 (0.2 g; 1.13 mmol) in anhydrous dichloroethane (5.6 mL) was added chlorosulfonic acid (0.1 mL; 1.36 mmol) dropwise (1 mL/minutes). The reaction mixture was allowed to gradually warm to room temperature while stirring overnight. The reaction mixture was diluted with aqueous hydrochloric acid (2 mL; 2N) and extracted with ethyl acetate (2×10 mL). The combined organic phases were dried over sodium sulfate, filtered, and concentrated under reduced pressure to yield a yellow-orange solid as a mixture of the two regioisomers (0.25 g).

III. 4-Cyclopentyl-2-fluorobenzene-1-sulfonyl chloride (134) and 2-cyclopentyl-4-fluorobenzene-1-sulfonyl chloride (135)

To a cooled (0° C.) solution of 132/133 (0.25 g; 1.0 mmol) in dichloroethane (10 mL) was added 1.0 equivalent phosphorus pentachloride (total amount: 0.56 g; 2.7 mmol) slowly. After addition was complete, the reaction was stirred for 10 minutes then heated at reflux for 4 hours then cooled to 60° C. Another equivalent of the phosphorus pentachloride was added, and the reaction was stirred 16 hours. The reaction was allowed to cool to 60° C. then the remainder of phosphorus pentachloride was added. The reaction was stirred for 4 hours. After cooling to room temperature, the mixture was concentrated under reduced pressure and the crude residue was purified by automated silica gel column chromatography (Biotage®) eluting with ethyl acetate/hexanes to give the 134 as a white solid (0.06 g) and 135 as a white solid (0.11 g).

IV. Methyl 3-(2-cyclopentyl-4-fluorophenylsulfonamido)thiophene-2-carboxylate (136)

To a solution of 135 (0.1 g; 0.4 mmol) in dichloromethane (1.6 mL) at room temperature, methyl 3-aminothiophene-2-carboxylate (0.063 g; 0.4 mmol) was added followed by pyridine (0.4 g; 0.8 mmol) and then stirred at room temperature under a nitrogen atmosphere for 24 hours. The reaction mixture was concentrated under reduced pressure and then taken up in ethyl acetate (10 mL) and extracted with water. The aqueous layer separated and extracted with ethyl acetate (2×10 mL). The combined organic phases were successively washed with water and aqueous saturated sodium chloride, dried over magnesium sulfate, filtered and concentrated under reduced pressure. The resulting crude residue was purified by automated silica gel column chromatography (Biotage®) eluting with ethyl acetate/hexanes (0 to 40% v/v over 900 mL gradient elution) to give the title product as an off-white solid (79 mg).

V. 3-(2-Cyclopentyl-4-fluorophenylsulfonamido)thiophene-2-carboxylic acid (137)

To a solution of 136 (78.0 mg; 0.2 mmol) in tetrahydrofuran (5 mL) and methanol (5 mL) was added aqueous sodium hydroxide (7.5 mL; 2N) and then heated at 80° C. for 16 hours. The reaction mixture was allowed to cool to room temperature and then extracted with diethyl ether (20 mL).

The aqueous layer was separated and acidified with aqueous hydrochloric acid (15 mL; 2N) then extracted with ethyl acetate (2×15 mL). The combined organic phases were dried over magnesium sulfate, filtered, and concentrated under reduced pressure to yield the title product as a brown solid (76 mg).

VI. 3-(2-Cyclopentyl-4-fluorophenylsulfonamido) thiophene-2-carboxylic acid, disodium salt (138)

To a solution of 137 (74.0 mg; 0.2 mmol) in acetonitrile (2 mL), aqueous sodium hydroxide (4.0 mL; 0.4 mmol; 0.1N) and water (10 mL) were added. The reaction mixture was frozen in a dry ice/acetone bath and lyophilized to yield the title compound as a brown solid (76 mg).

Example 36

Preparation of 3-(4-cyclopentyl-2-fluorophenylsulfonamido)thiophene-2-carboxylic acid, disodium salt (141)

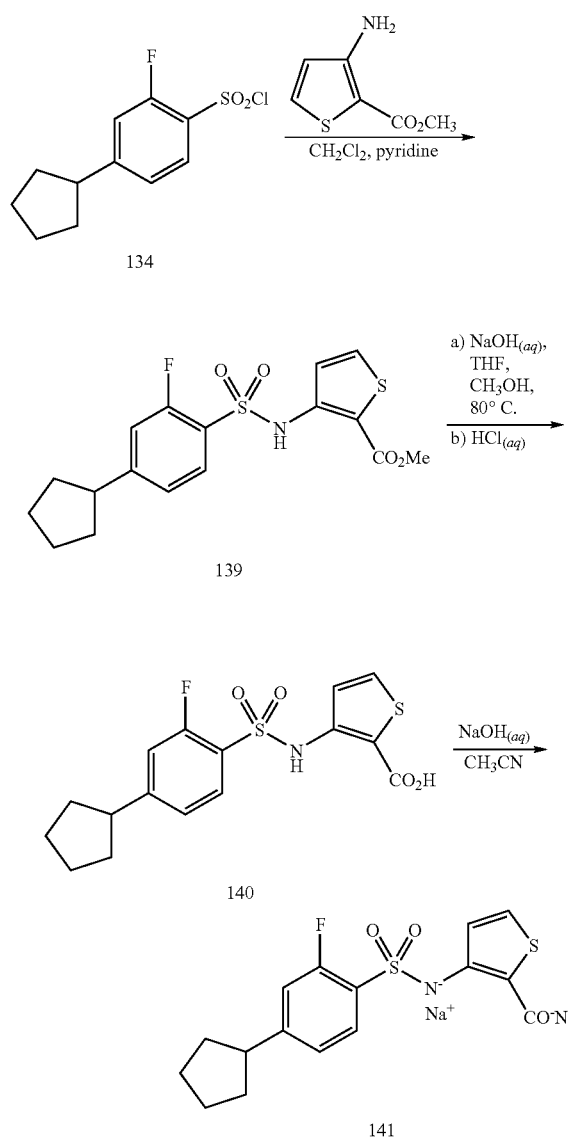

I. Methyl 3-(4-cyclopentyl-2-fluorophenylsulfonamido)thiophene-2-carboxylate (139)

To a solution of 4-cyclopentyl-2-fluorobenzene-1-sulfonyl chloride, 134 (0.06 g; 0.21 mmol) in dichloromethane (1 mL) at room temperature, methyl 3-aminothiophene-2-carboxylate (0.033 g; 0.21 mmol) was added followed by pyridine (0.033 g; 0.42 mmol) and then stirred at room temperature under a nitrogen atmosphere for 24 hours. The reaction mixture was concentrated under reduced pressure and then taken up in ethyl acetate (10 mL) and washed with water. The aqueous layer was separated and extracted with ethyl acetate (2×10 mL). The combined organic phases were successively washed with water and aqueous saturated sodium chloride, dried over magnesium sulfate, filtered and concentrated under reduced pressure. The resulting crude residue was purified by automated silica gel column chromatography (Biotage®) eluting with ethyl acetate/hexanes (0 to 40% v/v over 900 mL gradient elution) to give the title product as an off-white solid (34 mg).

II. 3-(4-Cyclopentyl-2-fluorophenylsulfonamido) thiophene-2-carboxylic acid (140)

To a solution of 139 (33.0 mg; 0.084 mmol) in tetrahydrofuran (5 mL) and methanol (5 mL) was added aqueous sodium hydroxide (7.5 mL; 2N) and then heated at 80° C. for 16 hours. The reaction mixture was allowed to cool to room temperature and then extracted with diethyl ether. The aqueous layer was separated and acidified with aqueous hydrochloric acid (5 mL; 2N) then extracted with ethyl acetate (2×15 mL). The combined organic phases were dried over magnesium sulfate, filtered, and concentrated under reduced pressure to yield the title product as a brown solid (32 mg).

III. 3-(4-Cyclopentyl-2-fluorophenylsulfonamido) thiophene-2-carboxylic acid, disodium salt (141)

To a solution of 140 (30.0 mg; 0.081 mmol). In acetonitrile (2 mL) aqueous sodium hydroxide (1.63 mL; 0.16 mmol; 0.1N) and water (10 mL) were added. The reaction mixture was frozen in a dry ice/acetone bath and lyophilized to yield the title compound as a brown solid (32 mg).

Example 37

Preparation of 3-[4-(iso-propylphenyl)sulfonamido] thiophene-2-carboxylic acid, disodium salt (144)

I. Methyl 3-[4-(iso-propyl)phenylsulfonamido] thiophene-2-carboxylate (142)

Synthesized as described for 52 using commercially available 4-iso-propylbenzenesulfonyl chloride (1.0 g; 4.57 mmol), methyl 3-aminothiophene-2-carboxylate (0.72 g; 4.57 mmol), pyridine (0.55 mL; 6.86 mmol), and anhydrous dichloromethane (3 mL). This afforded the title compound as a white solid (1.0 g).

II. 3-[4-(iso-Proylphenyl)sulfonamido]thiophene-2-carboxylic acid (143)

Synthesized as described for 53 using 142 (0.65 g; 1.9 mmol), aqueous sodium hydroxide (5 mL; 2N) and tetrahydrofuran (10 mL). This afforded the title compound as a white solid (0.21 g).

III. 3-[4-(iso-Propylphenyl)sulfonamido]thiophene-2-carboxylic acid, disodium salt (144)

Synthesized as described for 54 using 143 (210 mg; 0.65 mmol), acetonitrile (2 mL) and aqueous sodium hydroxide (12.9 mL; 1.3 mmol; 0.1N). This afforded the title compound as an off-white solid (211 mg).

Example 38

Preparation of 3-[4-(n-butylphenyl)sulfonamide]thiophene-2-carboxylic acid, disodium salt (147)

I. Methyl 3-[4-(n-butyl)phenylsulfonamido]thiophene-2-carboxylate (145)

Synthesized as described for 52 using commercially available 4-n-butylbenzenesulfonyl chloride (0.47 g; 2 mmol), methyl 3-aminothiophene-2-carboxylate (314 mg; 2 mmol), pyridine (0.2 mL; 2.4 mmol), and anhydrous dichloromethane (10 mL). This afforded the title compound as a clear oil which later solidified (0.6 g).

II. 3-[4-(n-Butylphenyl)sulfonamide]thiophene-2-carboxylic acid (146)

Synthesized as described for 53 using 145 (166 mg; 0.47 mmol), aqueous lithium hydroxide (1 mL; 2N) and tetrahydrofuran (4 mL). This afforded the title compound as a white solid (109 mg).

III. 3-[4-(n-Butylphenyl)sulfonamide]thiophene-2-carboxylic acid, disodium salt (147)

Synthesized as described for 54 using 146 (109 mg; 0.32 mmol), acetonitrile (1 mL) and aqueous sodium hydroxide (6.4 mL; 0.1N). This afforded the title compound as a white solid 123 mg).

Example 39

Preparation of 3-(2'-ethylbiphenyl-3-ylsulfonamido)thiophene-2-carboxylic acid, disodium salt (150)

I. Methyl 3-(2'-ethylbiphenyl-3-ylsulfonamido)thiophene-2-carboxylate (148)

Synthesized as described for 82 using 81 (500 mg; 1.33 mmol), 2-ethylphenylboronic acid (398 mg; 2.65 mmol), bis(triphenylphosphine)palladium(II) dichloride (47 mg; 0.07 mmol), acetonitrile (3 mL), aqueous saturated sodium bicarbonate (1.1 mL) and Reaction Time=30 minutes. The crude product was purified by automated silica gel column chromatography (Biotage®) eluting with 25% ethyl acetate in hexanes to give the title compound as a tan solid (436 mg).

II. 3-(2'-Ethylbiphenyl-3-ylsulfonamido)thiophene-2-carboxylic acid (149)

Synthesized as described for 83 using 148 (434 mg; 1.08 mmol), tetrahydrofuran (20 mL), methanol (5.8 mL), aqueous sodium hydroxide (13 mL; 26.0 mmol; 2M) and the reaction was heated at 70° C. The crude product was purified by automated silica gel column chromatography (Biotage®) to give the title compound as a white solid (89 mg).

III. 3-(2'-Ethylbiphenyl-3-ylsulfonamido)thiophene-2-carboxylic acid, disodium salt (150)

Synthesized as described for 84 using 149 (89 mg; 0.23 mmol), acetonitrile (3 mL) and aqueous sodium hydroxide (2.19 mL; 0.23 mmol; 0.105M). This afforded the title compound as a pink solid (81 mg).

Example 40

Preparation of 3-(biphenyl-3-ylsulfonamido)thiophene-2-carboxylic acid, disodium salt (153)

I. Methyl 3-(biphenyl-3-ylsulfonamido)thiophene-2-carboxylate (151)

To a solution of 81 (318 mg; 0.85 mmol) in toluene (8.5 mL) was added a solution of phenylboronic acid (152 mg; 1.12 mmol) in ethanol (5.6 mL). Bis(triphenylphosphine)palladium(II) dichloride (32 mg; 0.05 mmol) was then added, followed by the addition of aqueous saturated sodium bicarbonate (3.3 mL). The reaction was placed under a nitrogen atmosphere and then heated at 80° C. for 17 hours. After cooling to room temperature, the reaction was extracted with dichloromethane (70 mL) and washed with aqueous hydrochloric acid (40 mL; 2N), water (40 mL), and aqueous saturated sodium chloride (40 mL). The dichloromethane extracts were dried over magnesium sulfate, filtered, and concentrated under reduced pressure. The crude residue was purified by a silica gel chromatography (9% to 16% ethyl acetate in hexanes gradient) to yield the title compound as a white solid (217 mg).

II. 3-(Biphenyl-3-ylsulfonamido)thiophene-2-carboxylic acid (152)

Synthesized as described for 83 using 151 (215 mg; 0.58 mmol), tetrahydrofuran (5.8 mL), methanol (1.4 mL) and aqueous sodium hydroxide (5.8 mL; 2M). This afforded the title compound as white solid (207 mg).

III. 3-(Biphenyl-3-ylsulfonamido)thiophene-2-carboxylic acid, disodium salt (153)

Synthesized as described for 84 using 152 (131 mg; 0.36 mmol), acetonitrile (6.0 mL) and aqueous sodium hydroxide (6.9 mL; 0.73 mmol; 0.105 M). This afforded the title compound as off-white solid (43 mg).

Example 41

Preparation of 3-(2',6'-dimethylbiphenyl-3-ylsulfonamido)thiophene-2-carboxylic acid, disodium salt (156)

I. Methyl 3-(2',6'-dimethylbiphenyl-3-ylsulfonamido)thiophene-2-carboxylate (154)

Synthesized as described for 82 using 81 (513 mg; 1.36 mmol), 2,6-dimethylphenyboronic acid (262 mg; 1.75 mmol), bis(triphenylphosphine)palladium(II) dichloride (47 mg; 0.07 mmol), acetonitrile (2.7 mL) and aqueous saturated sodium bicarbonate (2.7 mL). The crude product was purified by automated silica gel column chromatography (Biotage®)

eluting with ethyl acetate/hexanes (4 to 24% v/v gradient elution; 3 runs required to obtain pure product) to give the title compound as a white solid (239 mg).

II. 3-(2',6'-Dimethylbiphenyl-3-ylsulfonamido) thiophene-2-carboxylic acid (155)

A solution of 154 (172 mg; 0.43 mmol) in tetrahydrofuran (2.1 mL) was placed in a 2.5-5.0 mL microwave reactor tube. Aqueous sodium hydroxide (2.1 mL; 2N) was added and the reaction vessel was subjected to the following microwave conditions: Temperature=140° C.; Time=30 minutes; Power=250 W; Cooling on; Absorption=High. After cooling to room temperature, the reaction mixture was acidified with aqueous hydrochloric acid (25 mL; 6N) and extracted with ethyl acetate (40 mL×2). The organic layers were combined and successively washed with aqueous sodium hydroxide (20 mL; 2N), aqueous hydrochloric acid (25 mL; 6N), and aqueous saturated sodium chloride (25 mL). The dichloromethane extracts were dried over magnesium sulfate, filtered, and concentrated under reduced. The resulting white solid was purified by silica gel chromatography (2 columns; $1^{st}$ column gradient: 16% ethyl acetate in hexanes to 5% methanol in dichloromethane; $2^{nd}$ column gradient: dichloromethane to 5% methanol in dichloromethane) to yield the title compound as a white solid (61 mg).

III. 3-(2',6'-Dimethylbiphenyl-3-ylsulfonamido) thiophene-2-carboxylic acid, disodium salt (156)

Synthesized as described for 84 using 155 (58 mg; 0.15 mmol), acetonitrile (8.0 mL) and aqueous sodium hydroxide (2.85 mL, 0.30 mmol; 0.105 M). This afforded the title compound as white solid (59 mg).

Example 42

Preparation of 3-(3',5'-dimethylbiphenyl-3-ylsulfonamido)thiophene-2-carboxylic acid, disodium salt (159)

I. Methyl 3-(3',5'-dimethylbiphenyl-3-ylsulfonamido)thiophene-2-carboxylate (157)

Synthesized as described for 82 using 81 (503 mg; 1.34 mmol), 3,5-dimethylphenyboronic acid (263 mg; 1.75 mmol), bis(triphenylphosphine)palladium(II) dichloride (48 mg; 0.07 mmol), acetonitrile (2.7 mL) and aqueous saturated sodium bicarbonate (0.7 mL). This afforded the title compound as white solid (0.14 g).

II. 3-(3',5'-Dimethylbiphenyl-3-ylsulfonamido) thiophene-2-carboxylic acid (158)

Synthesized as described for 155 using 157 (0.14 g; 0.35 mmol), tetrahydrofuran (1.7 mL) and aqueous sodium hydroxide (1.7 mL; 3.4 mmol; 2M). The crude white solid was recrystallized from 16% ethyl acetate in hexanes at room temperature to yield the title compound as a white solid (62 mg).

III. 3-(3',5'-Dimethylbiphenyl-3-ylsulfonamido) thiophene-2-carboxylic acid, disodium salt (159)

Synthesized as described for 84 using 158 (61 mg; 0.16 mmol), acetonitrile (3.0 mL) and aqueous sodium hydroxide (3.00 mL; 0.32 mmol; 0.105M). This afforded the title compound as white solid (67 mg).

Example 43

Preparation of 3-(2'-isopropylbiphenyl-3-ylsulfonamido)thiophene-2-carboxylic acid, disodium salt (162)

I. Methyl 3-(2'-isopropylbiphenyl-3-ylsulfonamido) thiophene-2-carboxylate (160)

Synthesized as described for 82 using 81 (367 mg; 0.98 mmol), (2-isopropylphenyl)boronic acid (209 mg; 1.27 mmol), bis(triphenylphosphine)palladium(II) dichloride (32 mg; 0.05 mmol), acetonitrile (2.0 mL), aqueous saturated sodium bicarbonate (0.5 mL) and Reaction Time=1 minute. This afforded the title compound as colorless film (184 mg).

II. 3-(2'-Isopropylbiphenyl-3-ylsulfonamido) thiophene-2-carboxylic acid (161)

Synthesized as described for 155 using 160 (70 mg; 0.17 mmol), tetrahydrofuran (1.4 mL) and aqueous sodium hydroxide (1.4 mL; 2.8 mmol; 2M). The crude product was purified by semi-preparative HPLC (gradient=30% to 95% acetonitrile in 0.1% $TFA_{(aq)}$) to yield the title compound as a white solid (35 mg).

III. 3-(2'-Isopropylbiphenyl-3-ylsulfonamido) thiophene-2-carboxylic acids disodium salt (162)

Synthesized as described for 84 using 161 (15 mg; 0.04 mmol), acetonitrile (1 mL) and aqueous sodium hydroxide (0.72 mL; 0.08 mmol; 0.105M). This afforded the title compound as white solid (13 mg).

Example 44

Preparation of 3-(2'-propoxybiphenyl-3-ylsulfonamido)thiophene-2-carboxylic acid, disodium salt (165)

I. Methyl 3-(2'-propoxybiphenyl-3-ylsulfonamido) thiophene-2-carboxylate (163)

Synthesized as described for 82 using 81 (506 mg; 1.34 mmol), 2-propoxyphenylboronic acid (488 mg; 2.71 mmol), bis(triphenylphosphine)palladium(II) dichloride (51 mg; 0.07 mmol), acetonitrile (3.3 mL), aqueous saturated sodium bicarbonate (1.1 mL) and Reaction Time=20 minutes. Purification of the crude product was not performed. This afforded the title compound as orange-yellow oil (no mass measured).

II. 3-(2'-Propoxybiphenyl-3-ylsulfonamido) thiophene-2-carboxylic acid (164)

Synthesized as described for 155 using 163 (540 mg; 1.34 mmol), tetrahydrofuran (2.7 mL), aqueous sodium hydroxide (1.4 mL; 2.80 mmol; 2M) and Reaction Time=1 hour. This afforded the title compound as colorless film (77 mg).

III. 3-(2'-Propoxybiphenyl-3-ylsulfonamido) thiophene-2-carboxylic acid, disodium salt (165)

Synthesized as described for 84 using 164 (56 mg; 0.14 mmol), acetonitrile (2.0 mL) and aqueous sodium hydroxide (2.57 mL; 0.27 mmol; 0.105M). This afforded the title compound as white solid (57 mg).

Example 45

Preparation of 3-[4-tert-Butyl-2-(3-chloropyridin-4-yl)phenyl-sulfonamido]thiophene-2-carboxylic acid (168)

I. Methyl 3-[4-tert-butyl-2-(3-chloropyridin-4-yl)-N-(methoxymethyl)phenylsulfonamido]thiophene-2-carboxylate (166)

Synthesized as described for 7 using 3-chloropyridin-4-ylboronic acid (102.0 mg; 0.65 mmol), 6 (200.0 mg; 0.43 mmol), cesium carbonate (420.0 mg; 1.29 mmol), tetrakis(triphenylphosphine)palladium(0) (25.0 mg; 0.022 mmol), toluene (1.3 mL), ethanol (1.3 mL) and water (1.3 mL). Purification by automated silica gel column chromatography (Biotage®) eluting with ethyl acetate/hexanes (0 to 25% v/v over 400 mL gradient elution) yielded the title product as a white solid (25.0 mg).

II. Methyl 3-[4-tert-butyl-2-(3-chloropyridin-4-yl)phenylsulfonamido]thiophene-2-carboxylate (167)

Synthesized as described for 22 using 166 (25.0 mg, 0.049 mmol), tetrahydrofuran (1 mL) and aqueous hydrochloric acid (1 mL). Purification by automated silica gel column chromatography (Biotage®) eluting with ethyl acetate/hexanes (0 to 30% v/v over 400 mL gradient elution) yielded the title product as a clear oil (15.2 mg).

III. 3-[4-tert-Butyl-2-(3-chloropyridin-4-yl)phenyl-sulfonamido]thiophene-2-carboxylic acid (168)

Synthesized as described for 23 using 167 (15.2 mg; 0.032 mmol) tetrahydrofuran (0.5 mL), methanol (0.5 mL) and aqueous lithium hydroxide (1.0 mL; 2M). Purification by preparative HPLC afforded the title compound as a white solid (7.5 mg).

Example 46

Preparation of 3-(5-tert-butylbiphenyl-2-ylsulfonamido)thiophene-2-carboxylic acid, disodium salt (172)

I. Methyl 3-[5-tert-butyl-N-(methoxymethyl)biphenyl-2-ylsulfonamido]thiophene-2-carboxylate (169)

Synthesized as described for 7 using 6 (200.0 mg; 0.43 mmol), phenylboronic acid (79.0 mg; 0.65 mmol), cesium carbonate (420 mg; 1.29 mmol), tetrakis(triphenylphosphine)palladium(0) (25.0 mg; 0.022 mmol), toluene (1.3 mL), ethanol (1.3 mL) and water (1.3 mL). This yielded the title product as a yellow oil (127 mg).

II. Methyl 3-(5-tert-butylbiphenyl-2-ylsulfonamido)thiophene-2-carboxylate (170)

Synthesized as described for 22 using 169 (126.0 mg; 0.27 mmol), tetrahydrofuran (5 mL) and aqueous hydrochloric acid (5 mL; 2N). The crude yellow oil was purified by automated silica gel column chromatography (Biotage®) eluting with ethyl acetate/hexanes (0 to 30% v/v over 400 mL gradient elution) to give the title product as clear oil (67.5 mg).

III. 3-(5-tert-Butylbiphenyl-2-ylsulfonamido)thiophene-2-carboxylic acid (171)

Synthesized as described for 23 using 170 (67.0 mg; 0.16 mmol), tetrahydrofuran (4 mL), methanol (1 mL) and aqueous sodium hydroxide (2.0 mL; 4.0 mmol; 2N). This yielded the title compound as a white solid (74.0 mg).

IV. 3-(5-tert-Butylbiphenyl-2-ylsulfonamido)thiophene-2-carboxylic acid, disodium salt (172)

Synthesized as described for 5 using 171 (71.0 mg; 0.17 mmol), aqueous sodium hydroxide (3.4 mL; 0.35 mmol; 0.1M). This yielded the title compound as a white solid (74.5 mg).

Example 47

Preparation of 3-[4-tert-Butyl-2-(piperidin-1-yl)phenylsulfonamido]thiophene-2-carboxylic acid (174)

I. Methyl 3-[4-tert-butyl-2-(piperidin-1-yl)phenylsulfonamido]thiophene-2-carboxylate (173)

Synthesized as described for 11 using 3 (200.0 mg; 0.46 mmol), copper(I) iodide (88.0 mg; 0.46 mmol), potassium carbonate (190.0 mg; 1.39 mmol), L-Proline (53.0 mg; 0.46 mmol), dimethyl sulfoxide (0.5 mL) and piperidine (0.091 mL; 0.93 mmol). The crude dark oil was purified by silica gel column chromatography eluting with ethyl acetate/hexanes (5 to 20% gradient elution) to give a white solid which was further purified by preparative HPLC to afford the title compound as a white solid (49.4 mg).

II. 3-[4-tert-Butyl-2-(piperidin-1-yl)phenylsulfonamido]thiophene-2-carboxylic acid (174)

Synthesized as described for 23 using 173 (40.0 mg; 0.091 mmol), aqueous sodium hydroxide (2 mL; 2M) and tetrahydrofuran (4 mL) and methanol (1 mL). After the usual work-up the title compound was obtained as a clear oil (35.0 mg).

Example 48

Preparation of 3-(4-tert-butyl-2-ethylphenylsulfonamido)thiophene-2-carboxylic acid, disodium salt (179)

I. 4-tert-Butyl-2-ethylbenzene-1-sulfonyl chloride (176)

Synthesized as described for 1 using 1-tert-butyl-3-ethylbenzene (5.0 g; 30.80 mmol), chlorosulfonic (2.46 mL; 36.96 mmol), and anhydrous dichloromethane (200 mL). The crude orange oil was purified by automated silica gel chromatography (Biotage®) eluting with ethyl acetate/hexanes (0 to 45% v/v over 350 mL gradient elution) to yield the title compound as dark oil (1.60 g).

II. Methyl 3-(4-tert-butyl-2-ethylphenylsulfonamido)thiophene-2-carboxylate (177)

Synthesized as described for 3 using 176 (1.60 g; 6.13 mmol), methyl 3-aminothiophene-2-carboxylate (1.06 g; 6.74 mmol), 4-dimethylaminopyridine (187.0 mg; 1.53 mmol), pyridine (4.95 mL; 61.3 mmol) and anhydrous dichloromethane (50 mL). Purification by automated silica gel chromatography (Biotage®) eluting with ethyl acetate/hexanes (0 to 10% v/v over 400 mL gradient elution) yielded the title product as a white solid (1.24 g).

III. 3-(4-tert-Butyl-2-ethylphenylsulfonamido) thiophene-2-carboxylic acid (178)

Synthesized as described for 23 using 177 (1.24 g; 3.26 mmol), tetrahydrofuran (20 mL), methanol (5 mL) and aqueous lithium hydroxide (16.3 mL; 2M). The crude beige solid obtained was co-evaporated twice from diisopropyl ether and then washed with hexanes to afford the title compound an off-white solid as (590 mg).

IV. 3-(4-tert-Butyl-2-ethylphenylsulfonamido) thiophene-2-carboxylic acid, disodium salt (179)

Synthesized as described for 5 using 178 (581 mg; 1.58 mmol), acetonitrile (10 mL) and aqueous sodium hydroxide (31.62 mL; 31.62 mmol; 0.1M). This afforded the title compound as an off-white solid (664 mg).

Example 49

Preparation of 3-(5,5,8,8-tetramethyl-5,6,7,8-tetrahydronaphthalene-2-sulfonamido)thiophene-2-carboxylic acid, disodium salt (182)

I. Methyl 3-(5,5,8,8-tetramethyl-5,6,7,8-tetrahydronaphthalene-2-sulfonamido)thiophene-2-carboxylate (180)

Synthesized as described for 3 using 5,5,8,8-tetramethyl-5,6,7,8-tetrahydronaphthalene-2-sulfonyl chloride (500.0 mg; 1.74 mmol), methyl 3-aminothiophene-2-carboxylate (301.4 mg; 1.91 mmol), 4-dimethylaminopyridine (53.1 mg; 0.44 mmol), pyridine (1.40 mL; 17.4 mmol) and anhydrous dichloromethane (200 mL). The crude residue was purified by automated silica gel chromatography (Biotage®) eluting with ethyl acetate/hexanes (0 to 25% v/v over 350 mL gradient elution) to yield the title compound as a white solid (359 mg).

II. 3-(5,5,8,8-Tetramethyl-5,6,7,8-tetrahydronaphtalene-2-sulfonamido)thiophene-2-carboxylic acid (181)

Synthesized as described for 23 using 180 (350.0 mg; 0.86 mmol), aqueous lithium hydroxide (4.3 mL; 8.6 mmol; 2M) and tetrahydrofuran (10 mL) and methanol (3 mL). This afforded the title compound as a white solid (318 mg).

III. 3-(5,5,8,8-Tetramethyl-5,6,7,8-tetrahydronaphthalene-2-sulfonamido)thiophene-2-carboxylic acid, disodium salt (182)

Synthesized as described for 5 using 181 (318 mg; 0.81 mmol), acetonitrile (12 mL), and aqueous sodium hydroxide (16.16 mL; 1.62 mmol; 0.1M). This afforded the title compound as an off-white solid (339 mg).

Example 50

Preparation of 3-[2-chloro-4-(trifluoromethoxy)phenylsulfonamido]thiophene-2-carboxylic acid, disodium salt (185)

I. Methyl 3-[2-chloro-4-(trifluoromethoxy)phenylsulfonamido]thiophene-2-carboxylate (183)

Synthesized as described for 3 using 2-chloro-4-(trifluoromethoxy)benzene-1-sulfonyl chloride (5.0 g; 16.94 mmol), methyl 3-aminothiophene-2-carboxylate (2.93 g; 18.63 mmol), 4-dimethylaminopyridine (517.0 mg; 4.23 mmol) pyridine (38.0 mL; excess) and anhydrous dichloromethane (100 mL). The resulting crude white crystalline solid was washed with acetone to afford the title compound as a white solid (2.14 g).

II. 3-[2-Chloro-4-(trifluoromethoxy)phenylsulfonamido]thiophene-2-carboxylic acid (184)

Synthesized as described for 23 using 183 (2.14 g; 5.15 mmol), aqueous lithium hydroxide (51.5 mL; 103 mmol; 2M), tetrahydrofuran (100 mL) and methanol (25 mL). The resulting crude beige solid was washed with acetonitrile to afford the title compound as a white solid (1.80 g).

III. 3-[2-Chloro-4-(trifluoromethoxy)phenylsulfonamido]thiophene-2-carboxylic acid, disodium salt (185)

Synthesized as described for 5 using 184 (1.23 g; 3.05 mmol), aqueous sodium hydroxide (61.10 mL; 6.11 mmol; 0.1M) and acetonitrile (15 mL). This afforded the title compound as a white solid (1.05 g).

Example 51

Preparation of 3-[2,6-dichloro-4-(trifluoromethyl) phenylsulfonamido]thiophene-2-carboxylic acid, disodium salt (188)

I. Methyl 3-[2,6-dichloro-4-(trifluoromethyl)phenylsulfonamido]thiophene-2-carboxylate (186)

Synthesized as described for 3 using 2,6-dichloro-4-(trifluoromethyl)benzene-1-sulfonyl chloride (2.5 g; 7.97 mmol), methyl 3-aminothiophene-2-carboxylate (1.14 g; 7.25 mmol), 4-dimethylaminopyridine (221.4 mg; 1.81 mmol), pyridine (11.81 mL; 145.0 mmol) and anhydrous dichloromethane (50 mL). Purification by automated silica gel chromatography (Biotage®) eluting with ethyl acetate/hexanes (0 to 30% v/v over 400 mL gradient elution) afforded the title compound as a white solid (2.20 g).

II. 3-[2,6-Dichloro-4-(trifluoromethyl)phenylsulfonamido]thiophene-2-carboxylic acid (187)

Synthesized as described for 23 using 186 (2.20 g; 5.06 mmol), aqueous lithium hydroxide (50 mL; 100 mmol; 2M), tetrahydrofuran (100 mL) and methanol (25 mL). The resulting crude beige solid was washed with acetonitrile to yield the title compound as a white solid (980 mg).

III. 3-[2,6-Dichloro-4-(trifluoromethyl)phenylsulfonamido]thiophene-2-carboxylic acid, disodium salt (188)

Synthesized as described for 5 using 187 (980 mg; 2.33 mmol), aqueous sodium hydroxide (46.6 mL; 4.66 mmol; 0.1M) and acetonitrile (15 mL). This afforded the title compound as a yellow solid (858 mg).

Example 52

Preparation of 3-[4-tert-butyl-2-(2-cyclopropylvinyl)phenylsulfonamido]thiophene-2-carboxylic acid, disodium salt (192)

I. Methyl 3-[4-tert-butyl-2-(2-cyclopropylvinyl)-N-(methoxymethyl)phenyl sulfonamido]thiophene-2-carboxylate (189)

Synthesized as described for 7 using 6 (400.0 mg; 0.87 mmol), cesium carbonate (845.0 mg; 2.60 mmol), cyclopropylvinylboronic acid pinacol ester (0.27 mL; 1.30 mmol), tetrakis(triphenylphosphine)palladium(0) (50.0 mg; 0.043 mmol), toluene (2 mL), water (2 mL) and ethanol (2 mL). The crude brown oil was purified by automated silica gel chromatography (Biotage®) eluting with ethyl acetate/hexanes (0 to 5% v/v gradient elution followed by 10% to 15% gradient elution) to give the title compound as a yellow oil (404 mg).

II. Methyl-3-[4-tert-butyl-2-(2-cyclopropylvinyl)phenylsulfonamido]thiophene-2-carboxylate (190)

Synthesized as described for 22 using 189 (400.0 mg; 0.86 mmol), hydrochloric acid (14.0 mL; 2N) and tetrahydrofuran (14 mL). After heating reaction at reflux for 16 hours, additional aqueous hydrochloric acid (14 mL; 6N) and tetrahydrofuran (14 mL) were added and heated for a further 4 hours. The crude clear oil was purified by automated silica gel chromatography (Biotage®) eluting with ethyl acetate/hexanes (0 to 20% gradient elution over 500 mL) to yield the title compound as a white solid (260 mg).

III. 3-[4-tert-Butyl-2-(2-cyclopropylvinyl)phenylsulfonamido]thiophene-2-carboxylic acid (191)

Synthesized as described for 23 using 190 (260.1 mg; 0.62 mmol), aqueous sodium hydroxide (9.0 mL; 2M), tetrahydrofuran (14 mL) and methanol (5 mL). This afforded the title compound as an off-white solid (205 mg).

IV. 3-[4-tert-Butyl-2-(2-cyclopropylvinyl)phenylsulfonamido]thiophene-2-carboxylic acid, disodium salt (192)

Synthesized as described for 5 using 191 (100 mg; 0.25 mmol), aqueous sodium hydroxide (4.8 mL; 0.49 mmol; 0.1M) and acetonitrile (1 mL). This afforded the title compound as a white solid (107 mg).

Example 53

Preparation of 3-(5-tert-butyl-3'-chlorobiphenyl-2-ylsulfonamido)thiophene-2-carboxylic acid, disodium salt (196)

I. Methyl 3-[5-tert-butyl-3'-chloro-N-(methoxymethyl)biphenyl-2-ylsolfonamido]thiophene-2-carboxylate (193)

Synthesized as described for 7 using 6 (200.0 mg; 0.43 mmol), cesium carbonate (420.0 mg 1.30 mmol), 3-chlorophenylboronic acid (100.0 mg; 0.65 mmol), tetrakis(triphenylphosphine)palladium(0) (25.0 mg; 0.022 mmol), toluene (1 mL), water (1 mL) and ethanol (1 mL). Purification by automated silica gel chromatography (Biotage®) yielded the title compound as a clear oil (135.6 mg).

II. Methyl 3-(5-tert-butyl-3'-chlorobiphenyl-2-ylsulfonamido)thiophene-2-carboxylate (194)

Synthesized as described for 22 using 193 (135.6 mg; 0.27 mmol), aqueous hydrochloric acid (5 mL; 2N) and tetrahydrofuran (5 mL). After heating the reaction at reflux for 16 hours, additional aqueous hydrochloric acid (5 mL; 6N) and tetrahydrofuran (5 mL) were added and the reaction heated for a further 4 hours. The crude yellow oil was purified by automated silica gel chromatography (Biotage®) eluting with ethyl acetate/hexanes (0 to 20% gradient elution over 500 mL) to yield the title compound as a clear oil (88 mg).

III. 3-(5-tert-Butyl-3'-chlorobiphenyl-2-ylsulfonamido)thiophene-2-carboxylic acid (195)

Synthesized as described for 23 using 194 (85.1 mg; 0.18 mmol), aqueous sodium hydroxide (4 mL; 2M), tetrahydrofuran (4 mL) and methanol (1.5 mL). This afforded the title compound as an off-white solid (70.6 mg).

IV. 3-(5-tert-Butyl-3'-chlorobiphenyl-2-ylsulfonamido)thiophene-2-carboxylic acid, disodium salt (196)

Synthesized as described for 5 using 195 (70.0 mg; 0.16 mmol), aqueous sodium hydroxide (3.0 mL; 0.31 mmol; 0.1M) and acetonitrile (1 mL). This afforded the title compound as a white solid (72 mg).

Example 54

Preparation of 3-(5-tert-butyl-3'-fluorobiphenyl-2-ylsulfonamido)thiophene-2-carboxylic acid, disodium salt (200)

I. Methyl 3-[5-tert-butyl-3'-fluoro-N-(methoxymethyl)biphenyl-2-ylsolfonamido]thiophene-2-carboxylate (197)

Synthesized as described for 7 using 6 (200.0 mg; 0.43 mmol), cesium carbonate (420.0 mg; 1.30 mmol), 3-fluorophenylboronic acid (91.0 mg; 0.65 mmol), tetrakis(triphenylphosphine)palladium(0) (25.0 mg; 0.022 mmol), toluene (1 mL), water (1 mL) and ethanol (1 mL). Purification of the crude brown oil by automated silica gel chromatography (Biotage®) afforded the title compound as a clear oil (154 mg).

II. Methyl 3-(5-tert-butyl-3'-fluorobiphenyl-2-ylsulfonamido)thiophene-2-carboxylate (198)

Synthesized as described for 22 using 197 (154.0 mg; 0.31 mmol), hydrochloric acid (5.0 mL; 2N) and tetrahydrofuran (5 mL). After heating the reaction at reflux for 16 hours additional aqueous hydrochloric acid (5 mL; 6N) and tetrahydrofuran (5 mL) were added and the reaction heated for a further 4 hours. The crude yellow oil was purified by automated silica gel chromatography (Biotage®) eluting with ethyl acetate/hexanes (0 to 20% gradient elution over 500 mL) to yield the title compound as a clear oil (111 mg).

III. 3-(5-tert-Butyl-3'-fluorobiphenyl-2-ylsulfonamido)thiophene-2-carboxylic acid (199)

Synthesized as described for 23 using 198 (110.8 mg; 0.25 mmol), aqueous sodium hydroxide (4.0 mL; 2M), tetrahydro-

IV. 3-(5-tert-Butyl-3'-fluorobiphenyl-2-ylsulfonamido)thiophene-2-carboxylic acid, disodium salt (200)

Synthesized as described for 5 using 199 (107 mg; 0.25 mmol), aqueous sodium hydroxide (4.8 mL; 0.49 mmol; 0.1M) and acetonitrile (1 mL). This afforded the title compound as a white solid (103 mg).

Example 55

Preparation of 3-[4-tert-butyl-2-(3-methoxyprop-1-enyl)phenylsulfonamido]thiophene-2-carboxylic acid, disodium salt (204)

I. Methyl 3-[4-tert-butyl-N-(methoxymethyl)-2-(3-methoxyprop-1-enyl)phenyl sulfonamido]thiophene-2-carboxylate (201)

Synthesized as described for 7 using 6 (300.0 mg; 0.65 mmol), cesium carbonate (634.0 mg; 1.95 mmol), (E)-2-(3-methoxyprop-1-enyl)-4,4,5,5-tetramethyl-1,3,2-dioxoborolane (193.0 mg; 0.97 mmol), tetrakis(triphenylphosphine)palladium(0) (37.0 mg; 0.032 mmol), toluene (1.5 mL), water (1.5 mL) and ethanol (1.5 mL). The crude dark oil purified by automated silica gel chromatography (Biotage®) eluting with ethyl acetate/hexanes (0 to 20% gradient elution over 500 mL) to yield the title compound as a yellow oil (189 mg).

II. Methyl 3-[4-tert-butyl-2-(3-methoxyprop-1-enyl)phenylsulfonamido]thiophene-2-carboxylate (202)

Synthesized as described for 22 using 201 (189.2 mg; 0.40 mmol), hydrochloric acid (6 mL; 2N) and tetrahydrofuran (6 mL). After heating the reaction at reflux for 16 hours, additional aqueous hydrochloric acid (6 mL; 6N) and tetrahydrofuran (6 mL) were added and the reaction heated for a further 4 hours. The crude clear oil was purified by automated silica gel chromatography (Biotage®) eluting with ethyl acetate/hexanes (0 to 20% gradient elution over 500 mL) to yield the title compound as a yellow solid (176 mg).

III. 3-[4-tert-Butyl-2-(3-methoxyprop-1-enyl)phenylsulfonamido]thiophene-2-carboxylic acid (203)

Synthesized as described for 23 using 202 (176.0 mg; 0.42 mmol), aqueous sodium hydroxide (7.0 mL; 2M), tetrahydrofuran (9 mL) and methanol (3.5 mL). This afforded the title compound was obtained as a yellowish oil (136 mg).

IV. 3-[4-tert-Butyl-2-(3-methoxyprop-1-enyl)phenylsulfonamido]thiophene-2-carboxylic acid, disodium salt (204)

Synthesized as described for 5 using 203 (86.9 mg; 0.21 mmol), aqueous sodium hydroxide (4.2 mL; 0.42 mmol; 0.1M) and acetonitrile (1 mL). This afforded the title compound as an off-white solid (108 mg).

Example 56

Preparation of 3-(4-tert-butyl-2-propylphenylsulfonamido)thiophene-2-carboxylic acid, disodium salt (209)

I. Methyl 3-[4-tert-butyl-N-(methoxymethyl)-2-(prop-1-enyl)phenylsulfonamido]thiophene-2-carboxylate (205)

Synthesized as described for 7 using 6 (600.0 mg; 1.30 mmol), cesium carbonate (1.27 g; 3.89 mmol), trans-1-propen-1-ylboronic acid (167.0 mg; 1.95 mmol), tetrakis(triphenylphosphine)palladium(0) (75.0 mg; 0.065 mmol), toluene (3 mL), water (3 mL) and ethanol (3.0 mL). This afforded a dark oil which was purified by automated silica gel column chromatography (Biotage®) eluting with ethyl acetate/hexanes (0 to 20% v/v over 500 mL gradient elution) to give the title compound as a yellow oil (332 mg).

II. Methyl 3-[4-tert-butyl-2-(prop-1-enyl)phenylsulfonamido]thiophene-2-carboxylate (206)

Synthesized as described for 22 using 205 (332.3 mg; 0.759 mmol), aqueous hydrochloric acid (12 mL; 2N) and tetrahydrofuran (12 mL). After heating the reaction at reflux for 16 hours, additional aqueous hydrochloric acid (12 mL; 6N) and tetrahydrofuran (12 mL) were added and the reaction heated for a further 4 hours. The crude clear oil was purified by automated silica gel chromatography (Biotage®) eluting with ethyl acetate, hexanes (0 to 20% gradient elution over 500 mL) to yield the title as a yellow solid (321 mg).

III. 3-[4-tert-butyl-2-(prop-1-enyl)phenylsulfonamido]thiophene-2-carboxylic acid (207)

Synthesized as described for 23 using 206 (321.0 mg; 0.82 mmol), aqueous sodium hydroxide (13 mL; 2M) tetrahydrofuran (18 mL) and methanol (7 mL). This afforded the title compound as a yellow oil (275 mg).

IV. 3-(4-tert-Butyl-2-propylphenylsulfonamido)thiophene-2-carboxylic acid (208)

A reaction vessel was charged with 207 (170.0 mg; 0.448 mmol), palladium on carbon (85.0 mg) and ethanol (4.5 mL) and then evacuated and filled with hydrogen gas (3×) and stirred at room temperature under hydrogen for 7 hours. The reaction mixture filtered through celite and the filtrate concentrated under reduced pressure to afford the title compound as a clear oil (147 mg).

IV. 3-(4-tert-Butyl-2-propylphenylsulfonamido)thiophene-2-carboxylic acid, disodium salt (209)

Synthesized as described for 5 using 208 (146 mg; 0.38 mmol), aqueous sodium hydroxide (7.70 mL; 0.77 mmol; 0.1M) and acetonitrile (1 mL). This afforded the title compound as an off-white solid (167 mg).

Example 57

Preparation of 3-[4-tert-Butyl-2-(2-cyclopropylethyl)phenylsulfonamido]thiophene-2-carboxylic acid, disodium salt (214)

I. Methyl 3-[4-tert-butyl-2-(2-cyclopropylvinyl)-N-(methoxymethyl)phenyl sulfonamido]thiophene-2-carboxylate (210)

Synthesized as described for 7 using 6 (400.0 mg; 0.87 mmol), cesium carbonate (845.0 mg; 2.60 mmol), cyclopropylvinylboronic acid pinacol ester (0.27 mL; 1.30 mmol), tetrakis(triphenylphosphine)palladium(0) (50.0 mg; 0.043 mmol), toluene (2 mL), water (2 mL) and ethanol (2 mL). The crude brown oil was purified by automated silica gel column chromatography (Biotage®) eluting with ethyl acetate/hexanes (0 to 20% v/v gradient elution) to give the title compound as a yellow oil (404 mg).

II. Methyl-3-[4-tert-butyl-2-(2-cyclopropylvinyl) phenylsulfonamido]thiophen-2-carboxylate (211)

Synthesized as described for 22 using 210 (400.0 mg; 0.86 mmol), aqueous hydrochloric acid (14 mL; 2N) and tetrahydrofuran (14 mL). After heating reaction at reflux for 16 hours additional aqueous hydrochloric acid (14 mL; 6N) and tetrahydrofuran (14 mL) were added and the reaction heated for a further 4 hours. The crude clear oil was purified by automated silica gel column chromatography (Biotage®) eluting with ethyl acetate/hexanes (0 to 20% v/v gradient elution over 500 mL) to give the title compound as a white solid (260 mg).

III. 3-[4-tert-Butyl-2-(2-cyclopropylvinyl)phenylsulfonamido]thiophen-2-carboxylic acid (212)

Synthesized as described for 23 using 211 (260.1 mg; 0.62 mmol), aqueous sodium hydroxide (9 mL; 2M), tetrahydrofuran (14 mL) and methanol (5 mL). This afforded the title compound as an off-white solid (205 mg).

IV. 3-[4-tert-Butyl-2-(2-cyclopropylethyl)phenylsulfonamido]thiophene-2-carboxylic acid (213)

Synthesized as described for 208 using 212 (85.0 mg; 0.21 mmol), palladium on carbon (43.0 mg; 0.91 mmol) and ethanol (2 mL). This afforded the title compound as a clear white solid (80.0 mg).

V. 3-[4-tert-Butyl-2-(2-cyclopropylethyl)phenylsulfonamido]thiophene-2-carboxylic acid, disodium salt (214)

Synthesized as described for 5 using 213 (100 mg; 0.25 mmol), aqueous sodium hydroxide (4.8 mL; 0.48 mmol; 0.1M) and acetonitrile (1 mL) and the reaction mixture required heating in a water bath in order to achieve a homogeneous solution. This afforded a mixture of the title compound (214) and 3-(4-tert-butyl-2-pentylphenylsulfonamido) thiophene-2-carboxylic acid (215; 29.9 mg). The title compound was purified by preparative HPLC to afford a white solid (31.5 mg; 0.08 mmol) which was dissolved in acetonitrile (1 mL) and treated with aqueous sodium hydroxide (1.5 mL; 0.15 mmol; 0.1M). The reaction mixture was frozen in a dry ice/acetone bath and lyophilized to yield the title compound as a white solid (28.9 mg).

Example 58

Preparation of 3-(4-tert-butyl-2-pentylphenylsulfonamido)thiophene-2-carboxylic acid, disodium salt (216)

I. Disodium (4-tert-butyl-2-pentylphenylsulfonyl) (carboxylatothiophen-3-yl)amide (216)

Synthesized as described for 5 using 215 (by-product from synthesis of 214) (26.9 mg; 0.066 mmol), aqueous sodium hydroxide (1.3 mL; 0.13 mmol; 0.1M) and acetonitrile (0.5 mL). This afforded a white solid as the title compound (24.6 mg).

Example 59

Preparation of 3-[4-tert-butyl-2-(3-methoxypropyl) phenylsulfonamido]thiophene-2-carboxylic acid, disodium salt (221)

I. Methyl 3-[4-tert-butyl-N-(methoxymethyl)-2-(3-methoxyprop-1-enyl)phenyl sulfonamido]thiophene-2-carboxylate (217)

Synthesized as described for 7 using 6 (300.0 mg, 0.65 mmol), cesium carbonate (634.0 mg; 1.95 mmol), (E)-2-(3-methoxyprop-1-enyl)-4,4,5,5-tetramethyl-1,3,2-dioxoborolane (193.0 mg; 0.97 mmol), tetrakis(triphenylphosphine) palladium(0) (37.0 mg; 0.032 mmol), toluene (1.5 mL), water (1.5 mL) and ethanol (1.5 mL). The crude dark oil was purified by automated silica gel column chromatography (Biotage®) eluting with ethyl acetate/hexanes (0 to 20% v/v gradient elution over 500 mL) to give the title compound as a yellow oil (189 mg).

II. Methyl 3-[4-tert-butyl-2-(3-methoxyprop-1-enyl) phenylsulfonamido]thiophene-2-carboxylate (218)

Synthesized as described for 22 using 217 (189.2 mg; 0.40 mmol), aqueous hydrochloric acid (6 mL; 2N) and tetrahydrofuran (6 mL). After heating the reaction at reflux for 16 hours, additional aqueous hydrochloric acid (6 mL; 6N) and tetrahydrofuran (6 mL) were added and the reaction heated for a further 4 hours. The crude clear oil was purified by automated silica gel chromatography (Biotage®) eluting with ethyl acetate/hexanes (0 to 20% gradient elution over 500 mL) to yield the title compound as a yellow solid (176 mg).

III. 3-[4-tert-Butyl-2-(3-methoxyprop-1-enyl)phenylsulfonamido]thiophene-2-carboxylic acid (219)

Synthesized as described for 23 using 218 (176.0 mg; 0.42 mmol), aqueous sodium hydroxide (7 mL; 2M), tetrahydrofuran (9 mL) and methanol (3.5 mL). This afforded the title compound as a yellow oil (136 mg).

IV. 3-[4-tert-Butyl-2-(3-methoxypropyl)phenylsulfonamido]thiophene-2-carboxylic acid (220)

Synthesized as described for 208 using 219 (50.0 mg; 0.12 mmol), palladium on carbon (25.0 mg) and ethanol (1.2 mL). This afforded the title compound as a clear oil (33.1 mg).

V. 3-[4-tert-Butyl-2-(3-methoxypropyl)phenylsulfonamido]thiophene-2-carboxylic acid, disodium salt (221)

Synthesized as described for 5 using 220 (20.8 mg; 0.051 mmol), aqueous sodium hydroxide (1 mL; 0.10 mmol; 0.1M) and acetonitrile (0.3 mL). This afforded the title compound as an off-white solid (10.4 mg).

Example 60

Preparation of 3-[4-tert-butyl-2-(furan-3-yl)-phenylsulfonamido]thiophene-2-carboxylic acid, disodium salt (225)

I. Methyl 3-[4-tert-butyl-2-(furan-3-yl)-N-(methoxymethyl)phenylsulfonamido]thiophene-2-carboxylate (222)

Synthesized as described for 7 using 6 (300.0 mg; 0.65 mmol), cesium carbonate (634.0 mg; 1.95 mmol), furan-3-ylboronic acid (109.0 mg; 0.97 mmol), tetrakis(triphenylphosphine)palladium(0) (37.0 mg; 0.032 mmol), toluene (1.5 mL), water (1.5 mL) and ethanol (1.5 mL). The crude dark oil was purified by automated silica gel chromatography (Biotage®) eluting with ethyl acetate/hexanes (0 to 20% gradient elution over 500 mL followed by 20% to 100% over 200.0 mL gradient elution) to yield the title compound as a brown oil (263 mg).

II. Methyl 3-[4-tert-butyl-2-(furan-3-yl)-phenylsulfonamido]thiophene-2-carboxylate (223)

Synthesized as described for 22 using 222 (263.0 mg; 0.59 mmol), aqueous hydrochloric acid (8 mL; 2N) and tetrahydrofuran (8 mL). After heating the reaction at reflux for 16 hours, additional aqueous hydrochloric acid (8 mL; 6N) and tetrahydrofuran (8 mL) were added and the reaction heated for a further 4 hours. The crude clear oil was purified by automated silica gel chromatography (Biotage®) eluting with ethyl acetate/hexanes (0 to 20% gradient elution over 700 mL followed by 20% to 100% over 200.0 mL gradient elution) to yield the title compound as a white solid (172 mg).

III. 3-[4-tert-Butyl-2-(furan-3-yl)-phenylsulfonamido]thiophene-2-carboxylic acid (224)

Synthesized as described for 23 using 223 (172.0 mg; 0.42 mmol), aqueous sodium hydroxide (10 mL; 2M), tetrahydrofuran (6 mL) and methanol (2 mL). This afforded the title compound as a white solid (137 mg).

IV. 3-[4-tert-Butyl-2-(furan-3-yl)-phenylsulfonamido]thiophene-2-carboxylic acid, disodium salt (225)

Synthesized as described for 5 using 224 (135 mg; 0.34 mmol), aqueous sodium hydroxide (6.9 mL; 0.69 mmol; 0.1M) and acetonitrile (1.0 mL). This afforded the title compound as a white solid (132 mg).

Example 61

Preparation of 3-(4-tert-butyl-2-vinylphenylsulfonamido)thiophene-2-carboxylic acid, disodium salt (229)

I. Methyl 3-[4-tert-butyl-N-(methoxymethyl)-2-vinylphenylsulfonamido]thiophene-2-carboxylate (226)

Synthesized as described for 7 using 6 (200.0 mg; 0.43 mmol), cesium carbonate (423.0 mg; 1.30 mmol), 2,4,6-trivinylcyclotriboroxane pyridine complex (156.1 mg; 0.65 mmol), tetrakis(triphenylphosphine)palladium(0) (25.0 mg; 0.022 mmol), toluene (1 mL), water (1 mL) and ethanol (1 mL). The crude dark oil was purified by automated silica gel chromatography (Biotage®) eluting with ethyl acetate/hexanes (0 to 20% gradient elution over 700 mL followed by 20% to 100% over 200.0 mL gradient elution) to yield the title compound as a yellow oil (84.8 mg).

II. Methyl 3-(4-tert-butyl-2-vinylphenylsulfonamido)thiophene-2-carboxylate (227)

Synthesized as described for 22 using 226 (84.8 mg; 0.21 mmol), aqueous hydrochloric acid (3 mL; 2N) and tetrahydrofuran (3 mL). After heating the reaction at reflux for 16 hours, additional aqueous hydrochloric acid (14 mL; 6N) and tetrahydrofuran (14 mL) were added and the reaction heated for a further 4 hours. The crude clear oil was purified by automated silica gel column chromatography (Biotage®) eluting with ethyl acetate/hexanes (0 to 20% v/v gradient elution over 500 mL followed by 20% to 100% v/v gradient elution) to give the title compound as a white solid (76.0 mg).

III. 3-(4-tert-Butyl-2-vinylphenylsulfonamido)thiophene-2-carboxylic acid (228)

Synthesized as described for 23 using 227 (76.0 mg; 0.21 mmol), aqueous sodium hydroxide (5 mL; 2M), tetrahydrofuran (5 mL) and methanol (1 mL). This afforded the title compound as a white solid (56.9 mg).

IV. 3-(4-tert-Butyl-2-vinylphenylsulfonamido)thiophene-2-carboxylic acid, disodium salt (229)

Synthesized as described for 5 using 228 (53.9 mg; 0.15 mmol), aqueous sodium hydroxide (3.06 mL; 0.31 mmol; 0.1M) and acetonitrile (0.5 mL). This afforded the title compound as an off-white solid (52.1 mg).

Example 62

Preparation of 3-(4-tert-butyl-2,6-dimethylphenylsulfonamido)thiophene-2-carboxylic acid, disodium salt (233)

I. 4-tert-Butyl-2,6-dimethylbenzene-1-sulfonyl chloride (230)

Synthesized as described for 1 using 1-tert-butyl-3,5-dimethylbenzene (5.76 mL; 30.81 mmol), chlorosulfonic acid (2.46 mL; 36.96 mmol) and anhydrous dichloromethane (200 mL). The crude residue was purified by automated silica gel column chromatography (Biotage®) eluting with ethyl acetate/hexanes (0 to 25% v/v gradient elution over 400 mL) to give the title compound as a white solid (1.60 g).

II. Methyl 3-(4-tert-butyl-2,6-dimethylphenylsulfonamido)thiophene-2-carboxylate (231)

Synthesized as described for 3 using 230 (1.58 g; 6.05 mmol), methyl 3-aminothiophene-2-carboxylate (1.05 g; 6.66 mmol), 4-dimethylaminopyridine (184.7 mg; 1.51 mmol), pyridine (4.89 mL; 60.5 mmol) and anhydrous dichloromethane (60 mL). The crude beige solid was purified by automated silica gel column chromatography (Biotage®) eluting with ethyl acetate/hexanes (0 to 25% v/v gradient elution over 400 mL) to give the title compound as a white solid (1.28 g).

III. 3-(4-tert-Butyl-2,6-dimethylphenylsulfonamido) thiophene-2-carboxylic acid (232)

Synthesized as described for 23 using 231 (1.28 g; 3.34 mmol), aqueous lithium hydroxide (16.7 mL; 33.4 mmol; 2M), tetrahydrofuran (30 mL) and methanol (8 mL). The crude beige solid washed with 20:3 v/v mL of hexanes/diisopropyl ether to afford the title compound as an off-white solid (590 mg).

IV. 3-(4-tert-Butyl-2,6-dimethylphenylsulfonamido) thiophene-2-carboxylic acids disodium salt (233)

Synthesized as described for 5 using 232 (586 mg; 1.59 mmol), aqueous sodium hydroxide (31.9 mL; 3.19 mmol; 0.1M) and acetonitrile (12 mL). This afforded the title compound as a white solid (661 mg).

Example 63

Preparation of 3-(2-chloro-4-fluoro-5-methoxyphenylsulfonamido)thiophene-2-carboxylic acid, disodium salt (236)

I. Methyl 3-(2-chloro-4,5-difluorophenylsulfonamido)thiophene-2-carboxylate (234)

Synthesized as described for 3 using 2-chloro-4,5,-difluorobenzenesulfonyl chloride (500 mg; 2.02 mmol), methyl 3-aminothiophene-2-carboxylate (382 mg; 2.43 mmol), 4-dimethylaminopyridine (62 mg; 0.51 mmol), pyridine (10 mL), and anhydrous dichloromethane (10 mL). The crude product was purified by automated silica gel chromatography (Biotage®) using ethyl acetate/hexanes as eluant system (0 to 20% v/v over 7 column volume gradient elution) to yield the title product as a white solid (249 mg).

II. 3-(2-Chloro-4-fluoro-5-methoxyphenylsulfonamido)thiophene-2-carboxylic acid (235)

Synthesized as described for 15 using 234 (0.25 g; 0.67 mmol), tetrahydrofuran (10 mL; methanol (2 mL) and aqueous sodium hydroxide (10 mL; 2N). This afforded the title compound as a white solid (204 mg).

III. 3-(2-Chloro-4-fluoro-5-methoxyphenylsulfonamido)thiophene-2-carboxylic acid, disodium salt (236)

Synthesized as described for 5 using 235 (202 mg; 0.57 mmol), acetonitrile (2 mL) and aqueous sodium hydroxide (11.4 mL; 1.14 mmol; 0.1M). This yielded the title compound as an off-white solid (237 mg).

Example 64

Biological Activity

CCR9 antagonist activity of exemplary compounds was determined using CCR9 FLIPR/FlexStation Assay as described in Section 4.4 and is provided in Table 1 below. The $IC_{50}$ for the compounds are represented as follows: A≦100 nM; B>100-500 nM; C>500 nM.

TABLE 1

| Ex# | Structure | Name | Mass Spec (m/z) | Binding $IC_{50}$ (nM) |
|---|---|---|---|---|
| 16 | 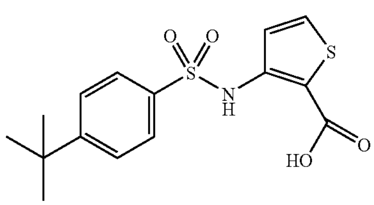 | 3-(4-tert-butylphenylsulfonamido)thiophene-2-carboxylic acid | Measured (M − H)⁻ = 338.07<br>Calculated (M − H)⁻ = 338.05 | A |
| 20 | 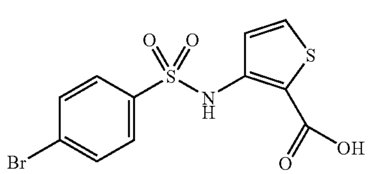 | 3-(4-bromophenylsulfonamido)thiophene-2-carboxylic acid | Measured (M − H)⁻ = 359.93<br>Calculated (M − H)⁻ = 359.90 | C |
| 40 | 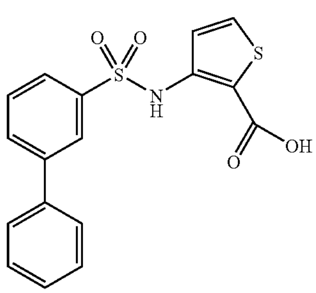 | 3-(biphenyl-3-ylsulfonamido)thiophene-2-carboxylic acid | Measured (M − H)⁻ = 358.07<br>Calculated (M − H)⁻ = 358.02 | C |

TABLE 1-continued

| Ex# | Structure | Name | Mass Spec (m/z) | Binding IC$_{50}$ (nM) |
|---|---|---|---|---|
| 18 | 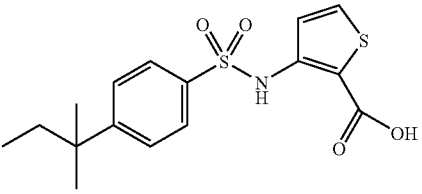 | 3-(4-(1,1-dimethylpropyl)phenyl-sulfonamido)thiophene-2-carboxylic acid | Measured (M − H)⁻ = 352.11<br>Calculated (M − H)⁻ = 352.07 | B |
| 25 | 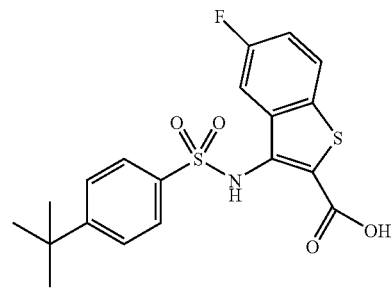 | 3-(4-tert-butylphenylsulfonamido-5-fluorobenzo[b]thiophene-2-carboxylic acid | Measured (M − H)⁻ = 406.00<br>Calculated (M − H)⁻ = 406.06 | C |
| 24 | 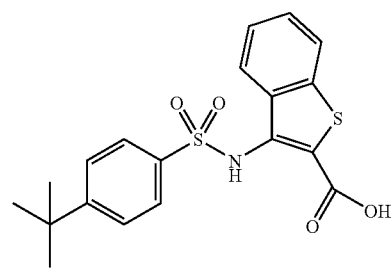 | 3-(4-tert-butylphenylsulfonamido)benzo[b]thiophene-2-carboxylic acid | Measured (M − H)⁻ = 388.10<br>Calculated (M − H)⁻ = 388.07 | B |
| 22 | 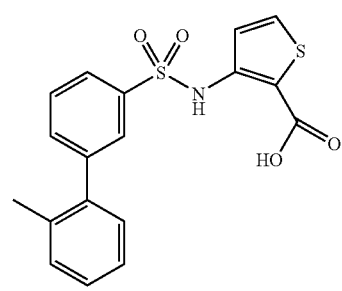 | 3-(2'-methylbiphenyl-3-ylsulfonamido)thiophene-2-carboxylic acid | Measured (M − H)⁻ = 372.07<br>Calculated (M − H)⁻ = 372.04 | C |
| 3 | 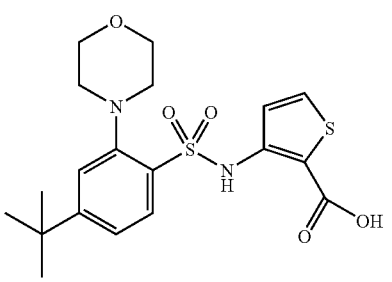 | 3-[4-tert-butyl-2-(morpholin-4-yl)phenylsulfonamido]thiophene-2-carboxylic acid | Measured (M − H)⁻ = 423.17<br>Calculated (M − H)⁻ = 423.11 | B |
| 1 | 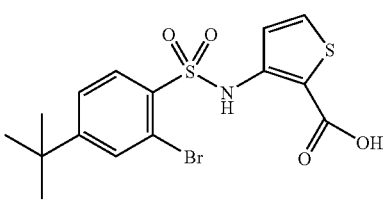 | 3-(2-bromo-4-tert-butylphenyl-sulfonamido)thiophene-2-carboxylic acid | Measured (M − H)⁻ = 415.98<br>Calculated (M − H)⁻ = 415.96 | A |

TABLE 1-continued

| Ex# | Structure | Name | Mass Spec (m/z) | Binding IC$_{50}$ (nM) |
|---|---|---|---|---|
| 26 | 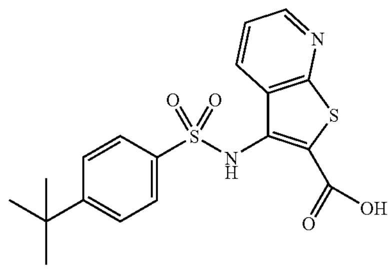 | 3-(4-tert-butylphenylsulfonamido)thieno[2,3-b]pyridine-2-carboxylic acid | Measured (M − H)⁻ = 389.10<br>Calculated (M − H)⁻ = 389.06 | C |
| 2 | 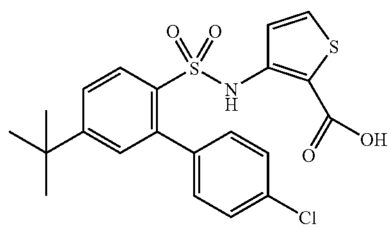 | 3-(5-tert-butyl-4'-chlorobiphenyl-2-ylsulfonamido)thiophene-2-carboxylic acid | Measured (M − H)⁻ = 448.10<br>Calculated (M − H)⁻ = 448.04 | C |
| 4 | 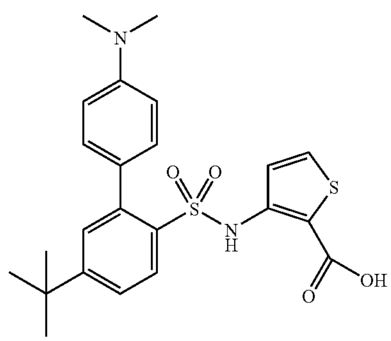 | 3-[5-tert-butyl-4'-(dimethylamino)biphenyl-2-ylsulfonamido]thiophene-2-carboxylic acid | Measured (M − H)⁻ = 457.17<br>Calculated (M − H)⁻ = 457.13 | C |
| 45 | 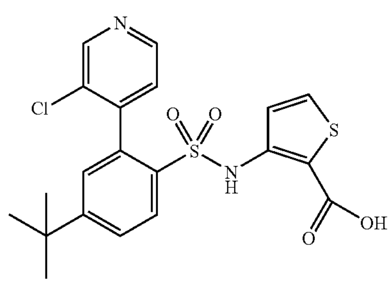 | 3-[4-tert-butyl-2-(3-chloropyridin-4-yl)phenylsulfonamido]thiophene-2-carboxylic acid | Measured (M − H)⁻ = 449.10<br>Calculated (M − H)⁻ = 449.04 | C |
| 47 | 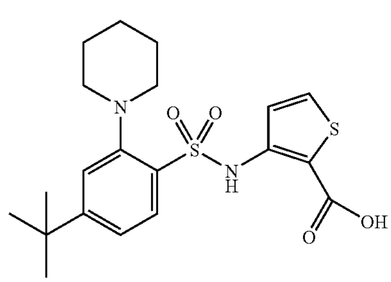 | 3-[4-tert-butyl-2-(piperidin-1-yl)phenylsulfonamido]thiophene-2-carboxylic acid | Measured (M − H)⁻ = 421.20<br>Calculated (M − H)⁻ = 421.13 | B |

TABLE 1-continued

| Ex# | Structure | Name | Mass Spec (m/z) | Binding IC$_{50}$ (nM) |
|---|---|---|---|---|
| 41 | 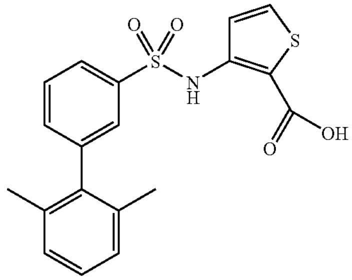 | 3-(2',6'-dimethylbiphenyl-3-ylsulfonamido)thiophene-2-carboxylic acid | Measured (M − H)⁻ = 386.00<br>Calculated (M − H)⁻ = 386.05 | C |
| 42 | 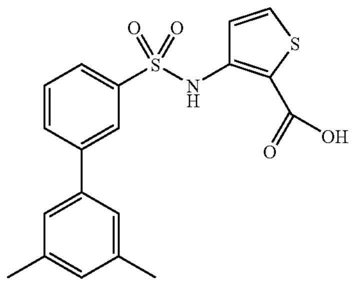 | 3-(3',5'-dimethylbiphenyl-3-ylfulfonamido)thiophene-2-carboxylic acid | Measured (M − H)⁻ = 386.00<br>Calculated (M − H)⁻ = 386.05 | C |
| 43 | 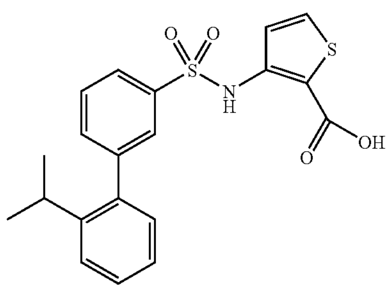 | 3-(2'-isopropylbiphenyl-3-ylsulfonamido)thiophene-2-carboxylic acid | Measured (M − H)⁻ = 400.08<br>Calculated (M − H)⁻ = 400.07 | C |
| 27 | 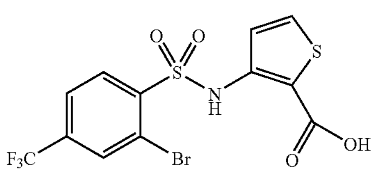 | 3-[2-bromo-4-(trifluoromethyl)phenylsulfonamido]thiophene-2-carboxylic acid | Measured (M − H)⁻ = 427.96<br>Calculated (M − H)⁻ = 427.89 | A |
| 46 | 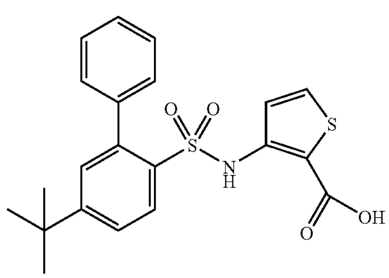 | 3-(5-tert-butylbiphenyl-2-ylsulfonamido)thiophene-2-carboxylic acid | Measured (M − H)⁻ = 414.06<br>Calculated (M − H)⁻ = 414.08 | C |

Expressing $(M-H)^-$ values where $M$ represents the molecular mass.

TABLE 1-continued

| Ex# | Structure | Name | Mass Spec (m/z) | Binding IC$_{50}$ (nM) |
|---|---|---|---|---|
| 44 | 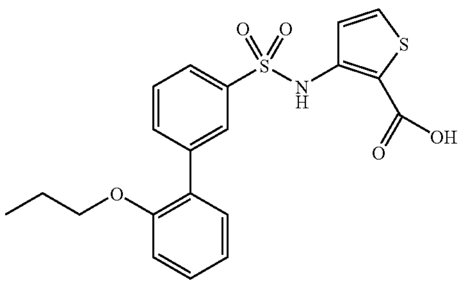 | 3-(2'-propoxybiphenyl-3-ylsulfonamido)thiophene-2-carboxylic acid | Measured (M − H)$^-$ = 418.09<br>Calculated (M − H)$^-$ = 418.08 | C |
| 5 | 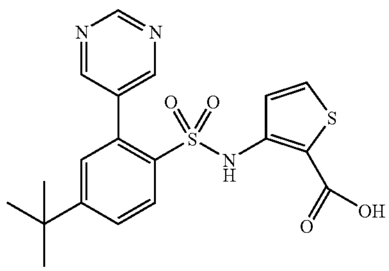 | 3-[4-tert-butyl-2-(pyrimidin-5-yl)phenylsulfonamido]thiophene-2-carboxylic acid | Measured (M − H)$^-$ = 416.07<br>Calculated (M − H)$^-$ = 416.07 | C |
| 39 | 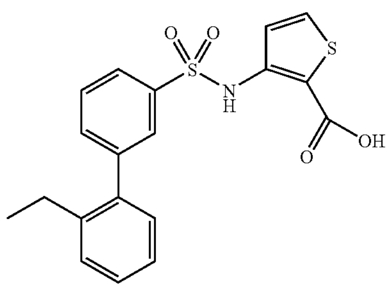 | 3-(2'-ethylbiphenyl-3-ylsulfonamido) thiophene-2-carboxylic acid | Measured (M − H)$^-$ = 385.05<br>Calculated (M − H)$^-$ = 386.05 | C |
| 6 | 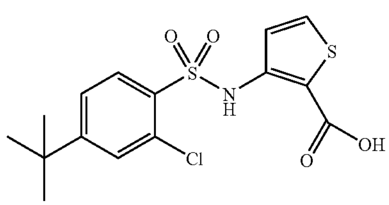 | 3-(4-tert-butyl-2-chlorophenylsulfonamido) thiophene-2-carboxylic acid | Measured (M − H)$^-$ = 372.01<br>Calculated (M − H)$^-$ = 372.01 | A |
| 7 | 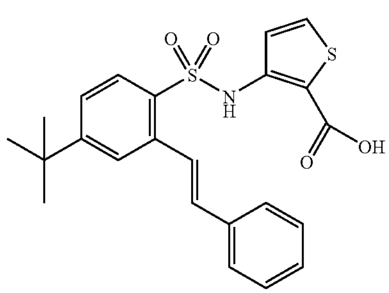 | 3-(4-tert-butyl-2-styrylphenylsulfonamido) thiophene-2-carboxylic acid | Measured (M + H)$^+$ = 442.11<br>Calculated (M + H)$^+$ = 442.11 | B |
| 8 | 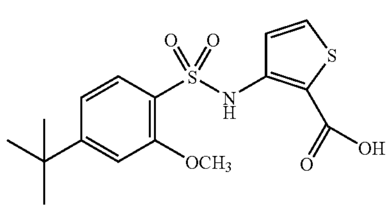 | 3-(4-tert-butyl-2-methoxyphenylsulfonamido)thiophene-2-carboxylic acid | Measured (M − H)$^-$ = 368.04<br>Calculated (M − H)$^-$ = 368.06 | A |

TABLE 1-continued

| Ex# | Structure | Name | Mass Spec (m/z) | Binding IC$_{50}$ (nM) |
|---|---|---|---|---|
| 9 | 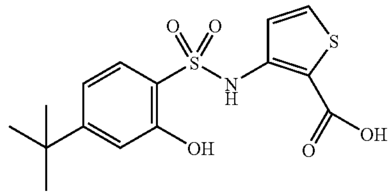 | 3-(4-tert-butyl-2-hydroxyphenylsulfon-amido)thiophene-2-carboxylic acid | Measured (M − H)⁻ = 354.05<br>Calculated (M − H)⁻ = 354.05 | B |
| 23 | 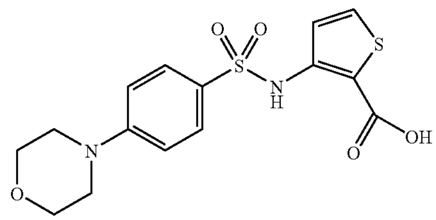 | 3-[(4-morpholin-4-yl)phenylsulfonamido]thiophene-2-carboxylic acid | Measured (M − H)⁻ = 367.10<br>Calculated (M − H)⁻ = 367.04 | C |
| 17 | 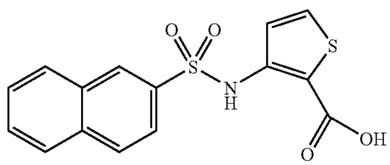 | 3-(naphthalene-2-sulfonamido)thiophene-2-carboxylic acid | Measured (M − H)⁻ = 331.98<br>Calculated (M − H)⁻ = 332.01 | C |
| 14 | 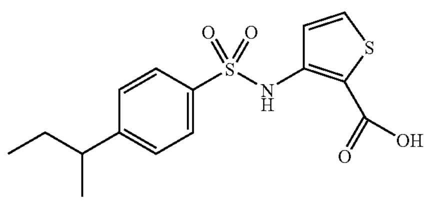 | 3-(4-sec-butylphenylsulfonamido)thiophene-2-carboxylic acid | Measured (M − H)⁻ = 338.00<br>Calculated (M − H)⁻ = 338.05 | A |
| 37 | 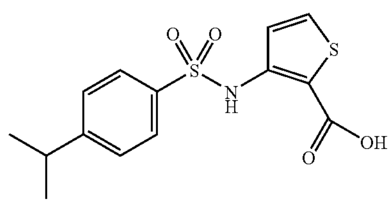 | 3-(4-isopropylphenylsulfonamido)thiophene-2-carboxylic acid | Measured (M − H)⁻ = 324.03<br>Calculated (M − H)⁻ = 324.04 | B |
| 21 | 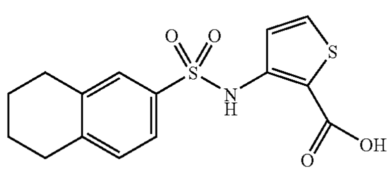 | 3-(5,6,7,8-tetrahydronaphthalene-2-sulfonamido)thiophene-2-carboxylic acid | Measured (M − H)⁻ = 336.02<br>Calculated (M − H)⁻ = 336.04 | B |
| 10 | 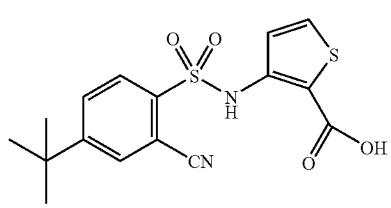 | 3-(4-tert-butyl-2-cyanophenylsulfonamido)thiophene-2-carboxylic acid | Measured (M − H)⁻ = 363.05<br>Calculated (M − H)⁻ = 363.05 | A |

TABLE 1-continued

| Ex# | Structure | Name | Mass Spec (m/z) | Binding IC$_{50}$ (nM) |
|---|---|---|---|---|
| 11 | 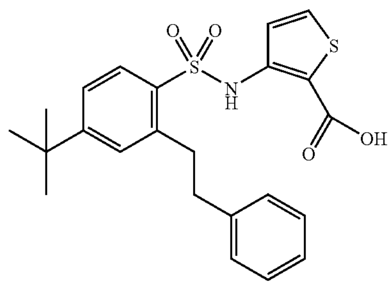 | 3-(4-tert-butyl-2-phenethylphenylsulfonamido)thiophene-2-carboxylic acid | Measured (M − H)⁻ = 442.10<br>Calculated (M − H)⁻ = 442.11 | A |
| 12 | 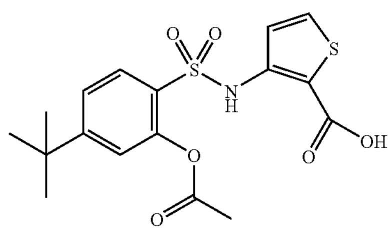 | 3-(2-acetoxy-4-tert-butylphenylsulfonamido)thiophene-2-carboxylic acid | Measured (M − H)⁻ = 396.00<br>Calculated (M − H)⁻ = 396.06 | B |
| 15 | 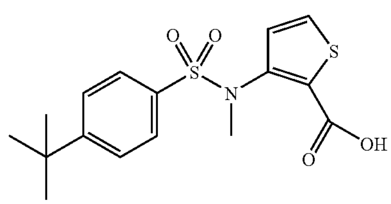 | 3-(4-tert-butyl-N-methylphenylsulfonamido)thiophene-2-carboxylic acid | Measured (M + H)⁺ = 353.95<br>Calculated (M + H)⁺ = 354.08 | C |
| 13 | 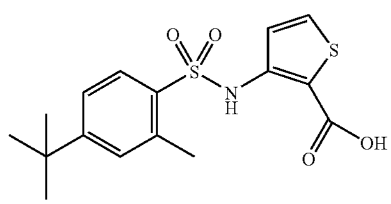 | 3-(4-tert-butyl-2-methylphenylsulfonamido)thiophene-2-carboxylic acid | Measured (M − H)⁻ = 352.01<br>Calculated (M − H)⁻ = 352.07 | A |
| 38 | 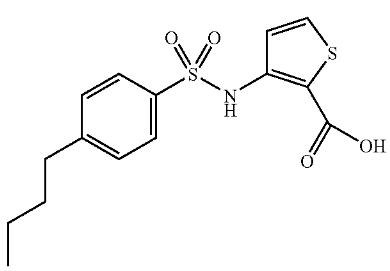 | 3-(4-butylphenylsulfonamido)thiophene-2-carboxylic acid | Measured (M − H)⁻ = 338.00<br>Calculated (M − H)⁻ = 338.05 | A |
| 48 | 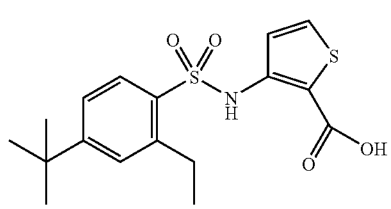 | 3-(4-tert-butyl-2-ethylphenylsulfonamido)thiophene-2-carboxylic acid | Measured (M − H)⁻ = 366.07<br>Calculated (M − H)⁻ = 366.08 | A |

TABLE 1-continued

| Ex# | Structure | Name | Mass Spec (m/z) | Binding IC$_{50}$ (nM) |
|---|---|---|---|---|
| 32 | 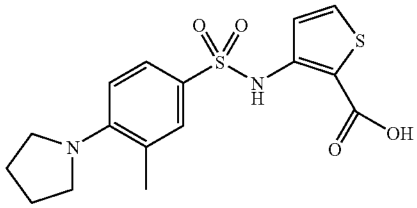 | 3-[3-methyl-4-(pyrrolidin-1-yl)phenylsulfonamido]thiophene-2-carboxylic acid | Measured (M − H)$^-$ = 365.07<br>Calculated (M − H)$^-$ = 365.06 | C |
| 28 | 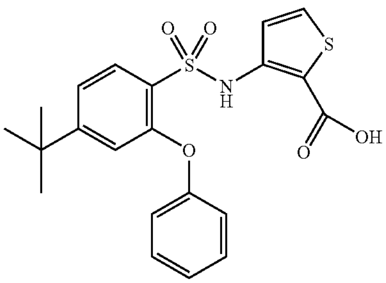 | 3-(4-tert-butyl-2-phenoxyphenylsulfonamido)thiophene-2-carboxylic acid | Measured (M − H)$^-$ = 430.08<br>Calculated (M − H)$^-$ = 430.08 | C |
| 34 | 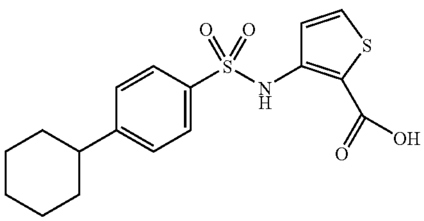 | 3-(4-cyclohexylphenylsulfonamido)thiophene-2-carboxylic acid | Measured (M − H)$^-$ = 364.07<br>Calculated (M − H)$^-$ = 364.07 | B |
| 62 | 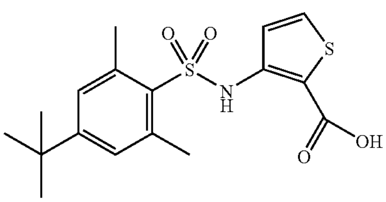 | 3-(4-tert-butyl-2,6-dimethylphenylsulfonamido)thiophene-2-carboxylic acid | Measured (M − H)$^-$ = 366.09<br>Calculated (M − H)$^-$ = 366.08 | C |
| 49 | 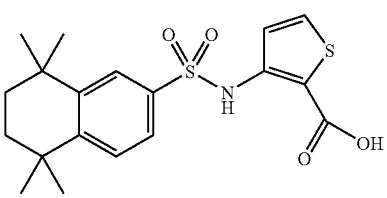 | 3-(5,5,8,8-tetramethyl-5,6,7,8-tetrahydronaphthalene-2-sulfonamido)thiophene-2-carboxylic acid | Measured (M + H)$^+$ = 394.12<br>Calculated (M + H)$^+$ = 394.11 | C |
| 31 | 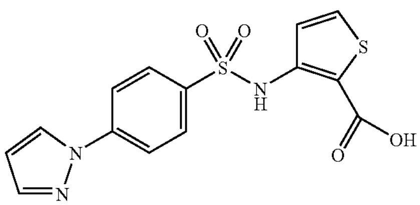 | 3-[4-(1H-pyrazol-1-yl)phenylsulfonamido]thiophene-2-carboxylic acid | Measured (M − H)$^-$ = 348.02<br>Calculated (M − H)$^-$ = 348.01 | C |
| 33 | 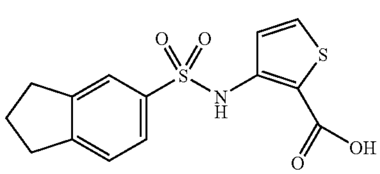 | 3-(2,3-dihydro-1H-indene-5-sulfonamido)thiophene-2-carboxylic acid | Measured (M − H)$^-$ = 322.03<br>Calculated (M − H)$^-$ = 322.02 | C |

TABLE 1-continued

| Ex# | Structure | Name | Mass Spec (m/z) | Binding IC$_{50}$ (nM) |
| --- | --- | --- | --- | --- |
| 35 | 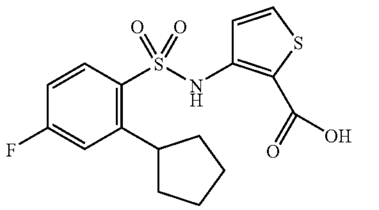 | 3-(2-cyclopentyl-4-fluorophenylsulfon-amido)thiophene-2-carboxylic acid | Measured (M − H)$^-$ = 368.04<br>Calculated (M − H)$^-$ = 368.04 | C |
| 36 | 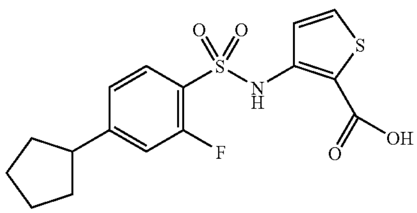 | 3-(4-cyclopentyl-2-fluorophenylsulfon-amido)thiophene-2-carboxylic acid | Measured (M − H)$^-$ = 368.05<br>Calculated (M − H)$^-$ = 368.04 | A |
| 50 | 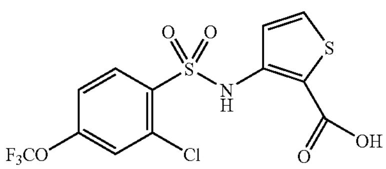 | 3-[2-chloro-4-(trifluoromethoxy)phenylsulfonamido]thiophene-2-carboxylic acid | Measured (M − H)$^-$ = 399.90<br>Calculated (M − H)$^-$ = 399.93 | A |
| 51 | 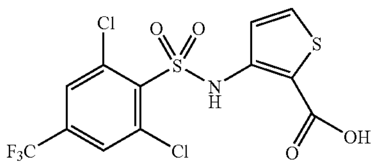 | 3-[2,6-dichloro-4-(trifluoromethyl)phenylsulfonamido]thiophene-2-carboxylic acid | Measured (M − H)$^-$ = 417.88<br>Calculated (M − H)$^-$ = 417.90 | C |
| 52 | 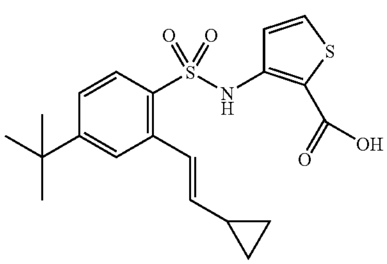 | 3-[4-tert-butyl-2-(2-cyclopropylvinyl)phenylsulfonamido]thiophene-2-carboxylic acid | Measured (M − H)$^-$ = 404.04<br>Calculated (M − H)$^-$ = 404.10 | A |
| 53 | 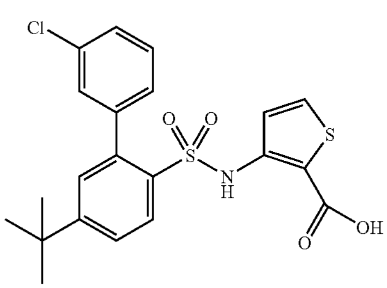 | 3-(5-tert-butyl-3'-chlorobiphenyl-2-ylsulfonamido)thiophene-2-carboxylic acid | Measured (M − H)$^-$ = 447.92<br>Calculated (M − H)$^-$ = 448.04 | C |

TABLE 1-continued

| Ex# | Structure | Name | Mass Spec (m/z) | Binding IC$_{50}$ (nM) |
|---|---|---|---|---|
| 54 | 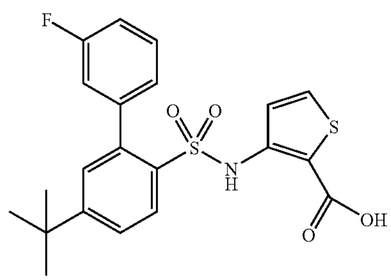 | 3-(5-tert-butyl-3'-fluorobiphenyl-2-ylsulfonamido)thiophene-2-carboxylic acid | Measured (M − H)⁻ = 431.97<br>Calculated (M − H)⁻ = 432.07 | B |
| 55 | 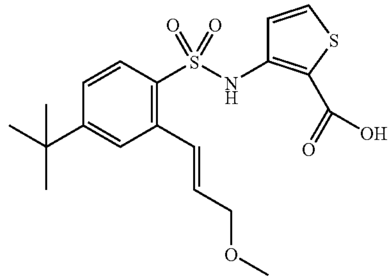 | 3-[4-tert-butyl-2-(3-methoxyprop-1-enyl)phenylsulfonamido]thiophene-2-carboxylic acid | Measured (M − H)⁻ = 408.09<br>Calculated (M − H)⁻ = 408.09 | B |
| 56 | 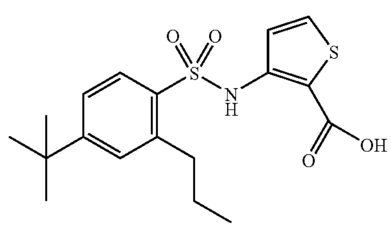 | 3-(4-tert-butyl-2-propylphenylsulfonamido)thiophene-2-carboxylic acid | Measured (M − H)⁻ = 380.11<br>Calculated (M − H)⁻ = 380.10 | A |
| 57 | 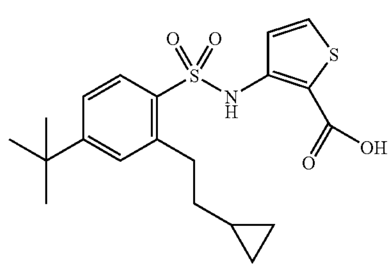 | 3-[4-tert-butyl-2-(2-cyclopropylethyl)phenylsulfonamido]thiophene-2-carboxylic acid | Measured (M − H)⁻ = 406.12<br>Calculated (M − H)⁻ = 406.14 | A |
| 58 | 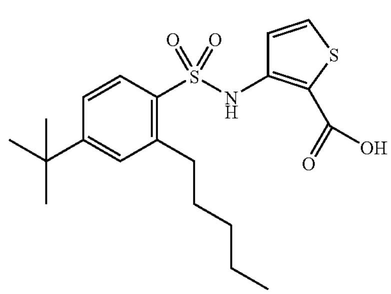 | 3-(4-tert-butyl-2-pentylphenylsulfonamido)thiophene-2-carboxylic acid | Measured (M − H)⁻ = 408.14<br>Calculated (M − H)⁻ = 408.13 | B |

TABLE 1-continued

| Ex# | Structure | Name | Mass Spec (m/z) | Binding IC$_{50}$ (nM) |
|---|---|---|---|---|
| 59 | 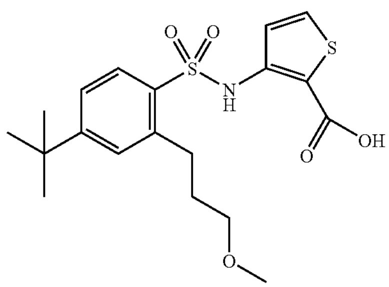 | 3-[4-tert-butyl-2-(3-methoxypropyl)phenylsulfonamido]thiophene-2-carboxylic acid | Measured (M − H)⁻ = 410.12<br>Calculated (M − H)⁻ = 410.11 | B |
| 29 | 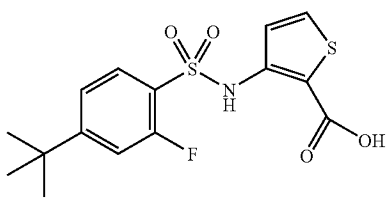 | 3-(4-tert-butyl-2-fluorophenylsulfonamido)thiophene-2-carboxylic acid | Measured (M − H)⁻ = 356.05<br>Calculated (M − H)⁻ = 356.04 | A |
| 60 | 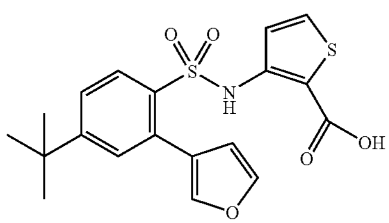 | 3-[4-tert-butyl-2-(furan-3-yl)phenylsulfonamido]thiophene-2-carboxylic acid | Measured (M − H)⁻ = 404.00<br>Calculated (M − H)⁻ = 404.06 | B |
| 63 | 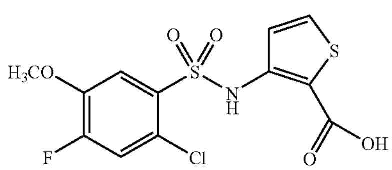 | 3-(2-chloro-4-fluoro-5-methoxyphenylsulfonamido)thiophene-2-carboxylic acid | Measured (M − H)⁻ = 363.90<br>Calculated (M − H)⁻ = 363.95 | C |
| 61 | 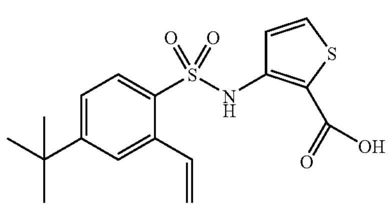 | 3-(4-tert-butyl-2-vinylphenylsulfonamido)thiophene-2-carboxylic acid | Measured (M − H)⁻ = 364.01<br>Calculated (M − H)⁻ = 364.07 | A |
| 19 | 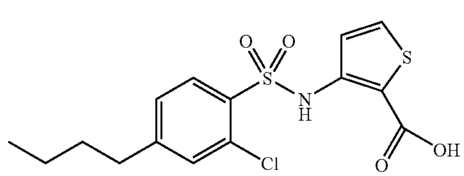 | 3-(4-butyl-2-chlorophenylsulfonamido)thiophene-2-carboxylic acid | Measured (M − H)⁻ = 372.02<br>Calculated (M − H)⁻ = 372.01 | A |

TABLE 1-continued

| Ex# | Structure | Name | Mass Spec (m/z) | Binding IC$_{50}$ (nM) |
|---|---|---|---|---|
| 30 | 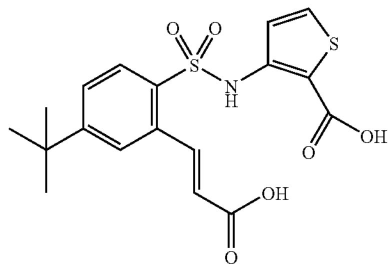 | 3-[4-tert-butyl-2-(2-carboxyvinyl)phenyl sulfonamido]thiophene-2-carboxylic acid | Measured (M − H)⁻ = 408.06<br>Calculated (M − H)⁻ = 408.06 | C |

The embodiments described above are intended to be merely exemplary, and those skilled in the art will recognize, or will be able to ascertain using no more than routine experimentation, numerous equivalents of specific compounds, materials, and procedures. All such equivalents are considered to be within the scope of the claimed subject matter and are encompassed by the appended claims.

What is claimed is:

1. 3-(4-tert-butylphenylsulfonamido)-5-fluorobenzo[b]thiophene-2-carboxylic acid or a pharmaceutically acceptable salt thereof.

2. The compound of claim 1 which has the following structure:

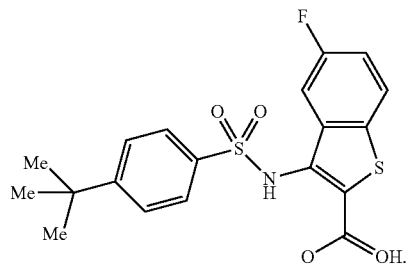

* * * * *